US011351291B2

(12) United States Patent
Kreymann et al.

(10) Patent No.: US 11,351,291 B2
(45) Date of Patent: Jun. 7, 2022

(54) SYSTEMS OR APPARATUSES AND METHODS FOR PERFORMING DIALYSIS

(71) Applicant: ADVITOS GMBH, Munich (DE)

(72) Inventors: Bernhard Kreymann, Munich (DE);
Christoph Huesstege, Munich (DE);
Catherine Elisabeth Schreiber,
Hohenbrunn-Riemerling (DE)

(73) Assignee: ADVITOS GMBH, Munich (DE)

( * ) Notice: Subject to any disclaimer, the term of this patent is extended or adjusted under 35 U.S.C. 154(b) by 0 days.

(21) Appl. No.: 16/084,477

(22) PCT Filed: Mar. 14, 2016

(86) PCT No.: PCT/IB2016/000287
§ 371 (c)(1),
(2) Date: Sep. 12, 2018

(87) PCT Pub. No.: WO2017/158392
PCT Pub. Date: Sep. 21, 2017

(65) Prior Publication Data
US 2019/0192757 A1 Jun. 27, 2019

(51) Int. Cl.
*A61M 1/16* (2006.01)
*A61M 1/34* (2006.01)

(52) U.S. Cl.
CPC ........ *A61M 1/1643* (2014.02); *A61M 1/1609* (2014.02); *A61M 1/1676* (2014.02);
(Continued)

(58) Field of Classification Search
CPC .............. A61M 1/1609; A61M 1/1643; A61M 1/1676; A61M 1/1696; A61M 1/3479;
(Continued)

(56) References Cited

U.S. PATENT DOCUMENTS 3,846,236 A 11/1974 Updike et al.
3,953,329 A 4/1976 Updike
(Continued)

FOREIGN PATENT DOCUMENTS

CN 1120439 A 4/1996
CN 101883594 A 11/2010
(Continued)

OTHER PUBLICATIONS

Japanese Notice of Reasons for Rejections in related Japanese Patent Application No. 2018-48367, dated Feb. 25, 2020, 13 pages with English Translation.
(Continued)

*Primary Examiner* — John Kim
(74) *Attorney, Agent, or Firm* — Medler Ferro Woodhouse & Mills PLLC

(57) ABSTRACT

The invention provides a method and an apparatus or system for dialysis. The method and apparatus or system are useful for removing an undesirable protein-binding substance such as a toxin from a biological fluid such as blood or blood plasma. As such, the method and apparatus or system are useful for treating a subject in need of dialysis such as a subject suffering from hepatic disease. The methods feature a) dialyzing a biological fluid against a dialysis fluid containing an adsorber for a protein-binding substance to be removed through a semipermeable membrane, b) adjusting the dialysis fluid so that the binding affinity of the adsorber for the protein-bound substance to be removed is lowered and the substance to be removed passes into solution, and c) balancing the volume or flow of one or more fluids in the apparatus or system suitable for dialyzing a biological fluid containing a protein-binding substance to be removed. The apparatus or system features a) a biological fluid circuit (3); b) a dialysis fluid circuit (2); c) a means (4; 6; 7; 8; 9) for
(Continued)

solubilizing the protein-binding substance to be removed; d) a dialysis, filtration or diafiltration device (5); e) a balancing system or apparatus suitable for balancing the volume or flow of one or more fluids in the apparatus or system suitable for dialyzing a biological fluid containing a protein-binding substance to be removed; and f) a dialysate regeneration unit.

19 Claims, 30 Drawing Sheets

(52) U.S. Cl.
CPC ........ *A61M 1/3479* (2014.02); *A61M 1/3482* (2014.02); *A61M 1/3486* (2014.02); *A61M 1/1696* (2013.01); *A61M 2205/3324* (2013.01); *A61M 2205/3368* (2013.01); *A61M 2205/3393* (2013.01)

(58) Field of Classification Search
CPC .............. A61M 1/3482; A61M 1/3486; A61M 2205/3324; A61M 2205/3368; A61M 2205/3393
See application file for complete search history.

(56) References Cited

U.S. PATENT DOCUMENTS

| | | | |
|---|---|---|---|
| 4,375,414 | A | 3/1983 | Strahilevitz |
| 4,663,049 | A | 5/1987 | Kolff et al. |
| 4,769,132 | A | 9/1988 | Patono |
| 5,561,115 | A | 10/1996 | Tenold |
| 5,744,042 | A | 4/1998 | Stange et al. |
| 6,264,680 | B1 | 7/2001 | Ash |
| 6,569,112 | B2 | 5/2003 | Strahilevitz |
| 6,602,502 | B1 | 8/2003 | Strahilevitz |
| 6,821,431 | B2 | 11/2004 | Collins et al. |
| 7,112,273 | B2 | 9/2006 | Weigel et al. |
| 7,435,342 | B2 | 10/2008 | Tsukamoto |
| 7,455,771 | B2 | 11/2008 | Kreymann |
| 7,670,491 | B2 | 3/2010 | Callan et al. |
| 8,377,308 | B2 | 2/2013 | Kreymann et al. |
| 8,480,899 | B2 | 7/2013 | Kreymann |
| 8,574,438 | B2 | 11/2013 | Kreymann et al. |
| 9,039,896 | B2 | 5/2015 | Kreymann |
| 9,248,112 | B2 | 2/2016 | Moddel et al. |
| 2002/0019603 | A1 | 2/2002 | Strahilevitz |
| 2002/0158019 | A1 | 10/2002 | Collins et al. |
| 2002/0187940 | A1 | 12/2002 | Masuda et al. |
| 2003/0105424 | A1 | 6/2003 | Karoor et al. |
| 2005/0006296 | A1* | 1/2005 | Sullivan ................ A61M 1/262 210/321.6 |
| 2005/0082225 | A1 | 4/2005 | Kreymann |
| 2010/0258503 | A1 | 10/2010 | Kreymann et al. |
| 2012/0080377 | A1 | 4/2012 | Jensen et al. |
| 2012/0190103 | A1 | 7/2012 | Maurer |
| 2013/0087210 | A1 | 4/2013 | Brandl et al. |
| 2013/0118979 | A1* | 5/2013 | Kreymann .......... A61M 1/1676 210/646 |
| 2015/0086969 | A1 | 3/2015 | Evans et al. |
| 2015/0012271 | A1 | 5/2015 | Brandl et al. |
| 2015/0335807 | A1 | 11/2015 | Kellum, Jr. et al. |

FOREIGN PATENT DOCUMENTS

| | | |
|---|---|---|
| CN | 102138932 A | 8/2011 |
| CN | 102421431 A | 4/2012 |
| CN | 102940886 A | 2/2013 |
| CN | 104394902 A | 3/2015 |
| EP | 0615780 | 9/1994 |
| EP | 0976759 A2 | 2/2000 |
| EP | 1649883 A1 | 4/2006 |
| EP | 1867354 | 12/2007 |
| EP | 2 019 296 | 1/2009 |
| EP | 2214752 | 8/2010 |
| FR | 2651438 A1 | 3/1991 |
| GB | 1484642 A | 9/1977 |
| JP | 2000-038348 A | 2/2000 |
| JP | 2000-72658 A | 7/2007 |
| JP | 2011-505209 A | 2/2011 |
| JP | 2012-228285 A | 11/2012 |
| WO | 8400689 A1 | 3/1984 |
| WO | 9421363 A1 | 9/1994 |
| WO | 01/51185 A1 | 7/2001 |
| WO | 2002/049693 A2 | 6/2002 |
| WO | 2003/094998 A1 | 11/2003 |
| WO | WO 2004/066121 | 8/2004 |
| WO | WO 2004/069311 | 8/2004 |
| WO | WO 2005/035023 | 4/2005 |
| WO | WO 2009/071103 | 6/2009 |
| WO | WO 2013/144793 | 10/2013 |
| WO | 2014/113740 A1 | 7/2014 |
| WO | WO 2014/160370 | 10/2014 |
| WO | WO 2015/074973 | 5/2015 |
| WO | 2017/084683 A1 | 5/2017 |
| WO | 2017/085291 A1 | 5/2017 |
| WO | 2018/215918 A1 | 11/2018 |

OTHER PUBLICATIONS

Armed Al-Chalabi et al.: "Evaluation of the Hepa Wash TM treatment in pigs with acute liver failure", BMC Gastroenterology, Biomed Central Ltd., London, GB, vol. 13, No. 1, May 13, 2013 (May 13, 2013), p. 83, XP021150648, ISSN: 1471-230X, DOI: 10.1186/1471-230X-13-83 the whole document figure 1.

Benjamin Struecker et al.: "Liver support strategies: cutting-edge technologies", Nature Reviews / Gastroenterology & Hepatology, vol. 11, No. 3, Oct. 29, 2013 (Oct. 29, 2013), pp. 166-176, XP055323390, US ISSN: 1759-5045, DOI: 10.1038/nrgastro.2013. 204 the whole document figure 1.

Karla C. L. Lee et al.: "Extracorporeal liver support devices for listed patients", Liver Transplantation, vol. 22, No. 6, May 26, 2016 (May 26, 2016), pp. 839-848, XP055323376, US ISSN: 1527-6465, DOI: 10.1002/lt.24396 the whole document.

Peters, T. "All About Albumin: Biochemistry, Genetics, and Medical Applications," Dec. 8, 1995; New York: Academic Press, Chapter 3.

Fasano et al., "The Extraordinary Ligand Binding Properties of Human Serum Albumin", Life Dec. 2005; 57(12): 787-796.

Vanholder et al., "A Bench to Bedside View of Uremic Toxins", A Soc Nephrol May 2008: 19:863-87.

A guide for the preparation and use of buffers in biological systems by Calbiochem, Date unknown.

Al-Chalabi, Ahmed et al., "Evaluation of the Hepa Wash Treatment in Pigs with Acute Liver Failure," BMC Gastroenterology, Biomed Central Ltd., London, GB, vol. 13, No. 1, May 13, 2013 (May 13, 2013), 10 pages.

Daugirdas, et al., Handbook of Dialysis, 4th Ed., pp. 59-79, (2007).

Huber et al., "First clinical experience in 14 patients treated with ADVOS: a study on feasibility, safety and efficacy of a new type of albumin dialysis", BMC Gastoenterology, vol. 17, No. 1, Feb. 16, 2017 (Feb. 16, 2017), pp. 1-11.

Jan Stange et al., Artificial Organs, 26 (2), International Society for Artificial Organs, "The Molecular Adsorbents Recycling System as a Liver Support System Based on Albumin Dialysis: A Summary of Preclinical Investigations, Prospective, Randomized, Controlled Clinical Trial, and Clinical Experience from 19 Centers" pp. 103-110, 2002.

J. G. O'Grady et al., Liver, Pancreas, and Biliary Tract, "Controlled Trials of Charcoal Hemoperfusion and Prognostic Factors in Fulminant Hepatic Failure", Gastroenterology 94: pp. 1186-1192, 1988.

Laleman et al., "Acute-on-chronic liver failure: current concepts on definition, pathogenesis, clinical manifestations and potential therapeutic interventions", Expert Review of Gastroenterology & Hepatology, vol. 5, No. 4, Aug. 2011 (Aug. 4, 2011), pp. 523-537.

Misra, "The Basics of Hemodialysis Equipment," Hemodialysis International 2005; 9: 30-36.

(56) References Cited

OTHER PUBLICATIONS

Nahas et al. (Guidelines for the Treatment of acidaemia with THAM, Drugs, pp. 191-224, Feb. 1998). (Year: 1998).
Nolte, Stephan H. et al., "Hemodialysis for Extracorporeal Bicarbonate/ $CO_2$ Removal (ECBic$CO_2$R) and Apneic Oxygenation for Respiratory Failure in the Newborn," ASAIO Transactions, vol. 35, No. 1, Jan. 1, 1989 (Jan. 1, 1989), 5 pages.
Polaschegg, et al., "Hemodialysis machines and monitors, in: Replacement of Renal Function by Dialysis", 5th Ed., eds. Horl, Koch, Lindsay, Ronco, Winchester, pp. 325-449, (2004).
Russ, Martin et al., "Experimental High-Volume Hemofiltration With Predilutional Tris-Hydroxymethylaminomethane for Correction of Low Tidal Volume Ventilation-Induced Acidosis," Artificial Organs, vol. 35, No. 6, May 30, 2011 (May 30, 2011), 11 pages.
Schwarzbeck, et al., Clin Nephrol, 1977 7(3): 125-7.
Sponholz et al., "Molecular adsorbent recirculating system and single-pass albumin dialysis in liver failure—a prospective, randomised crossover studfy", Critical Care (London, England), vol. 20, Jan. 4, 2016 (Jan. 4, 2016), pp. 1-13.
Table of Acids with Kas and pKas (1 page). (Year: 2002).
Worthley (Hydrogen Ion Metabolism, Anaeth. Intens. Care, 1977 5, pp. 347-360). (Year: 1977).

\* cited by examiner

SYSTEMS OR APPARATUSES AND METHODS FOR PERFORMING DIALYSIS

CROSS-REFERENCE TO RELATED PATENT APPLICATIONS

This application is a U.S. National Phase Application under 35 U.S.C. § 371 of International Patent Application No. PCT/IB2016/000287, filed Mar. 14, 2016, which is incorporated by reference as if expressly set forth in its entirety herein.

FIELD OF THE INVENTION

This invention relates to systems or apparatuses and methods for performing dialysis. Further, the invention relates to systems and methods for regenerating a dialysate and for measuring the total volume and balancing the total volume or flow of a fluid, such as a dialysate or an ultrafiltrate, within the systems.

BACKGROUND OF THE INVENTION

When the liver or kidney of a human being fail to perform their normal functions, inability to remove or metabolise certain substances results in their accumulation in the body. These substances may be differentiated according to their solubility in water: water-soluble and water-insoluble (or protein-bound). Different extracorporeal procedures are available to help replace the failing functions of one or more organs. Hemodialysis is the historically preferred means for treating patients with renal failure. For this purpose, a dialyzer is used which is divided into two compartments by a semipermeable membrane. Blood is passed through the blood compartment of the dialyzer separated by the semipermeable membrane from the dialysis fluid which passes through the dialysis compartment of the dialyzer. A physiological dialysis fluid should contain the desired electrolytes, nutrients and buffers in concentrations so that their levels in the patient's blood can be brought to normal.

Routine hemodialysis is of little help for patients with liver failure especially when they have no accompanying renal failure. This is primarily due to the fact that the primary toxins such as metabolites, e.g. bilirubin, bile acids, copper and other substances including gases, hormones or drugs accumulating in hepatic failure are protein-bound and therefore not effectively removed by hemodialysis.

Hepatic function can essentially be subdivided into two main functions: the synthesis of vital proteins and the removal of mainly protein-bound toxins. Basically only liver transplantation is currently available to replace the synthetic function. Although so-called bioreactors are known, with cells that at least partially take over the synthetic function of normal liver cells, these can only be used experimentally at the present time and their function is still insufficient. Liver transplantations are performed on approximately 20% of patients with acute liver failure because no adequate process for taking over the detoxication function exists, so the time taken for the hepatic function to recover cannot be bridged.

Protein-bound substances probably play an important role in the pathogenesis of hepatic encephalopathy, hepatic pruritus and hepatorenal syndrome. These pathogenic substances, which are bound predominantly to albumin, include especially aromatic compounds like phenol derivatives, indole derivatives, furan derivatives or aromatic amino acids, bilirubin, $C_4$-$C_7$ carboxylic acids, mercaptans, substances similar to digitoxin and benzodiazepine, and metal cations like copper cations, aluminium cations or iron cations. One of the most important diseases here is hepatic encephalopathy as it can be life-threatening and/or leave permanent damage. Since the 1970's, there have been a variety of attempts, based largely upon the dialysis technique, to replace the detoxication function of the liver.

In order to enhance the removal of these protein-bound substances, the dialysis fluid composition may be modified to contain albumin because albumin binds to unbound toxins travelling from the blood to the dialysate across a semipermeable membrane. This mode of treatment is often referred to as "albumin dialysis." The presence of albumin in the dialysate fluid facilitates the removal of protein-bound substances from the blood. The use of albumin is based upon the role of albumin as the main carrier protein for protein-bound toxins in the blood.

The molecular adsorbents recirculating system (MARS) described by Stange et al., EP 0,615,780 B1 uses a special albumin-coated dialysis membrane. The recirculating albumin-containing dialysate is passed over two adsorber columns (charcoal and resin) in order to eliminate the protein-bound toxins removed from the patient by dialysis and to prepare the binding sites of the albumin in the dialysate for toxins (Stange et al., *Artif. Organs* 2002; 26:103-110).

Albumin dialysis is a process similar to continuous haemodialysis. A feature of continuous renal replacement therapy is the use of slow dialysate flows (1-2 l/h compared to 30 l/h in normal dialysis). In albumin dialysis, in contrast to conventional continuous renal replacement therapy, albumin is added to the dialysate to give a 5% solution (Kreymann et al., *J. Hepatol.* 1999; 31:1080-1085). The use of albumin is based on its being the main carrier protein for protein-bound toxins in the blood.

Commercially available albumin is, however, very expensive. Therefore, albumin-based systems are very expensive forms of treatment. Furthermore, albumin-based dialysis systems provide unsatisfactory detoxification efficiency. On average they provide only up to 30% reduction in the bilirubin level, an accepted a marker for protein-bound substances. Although albumin-based dialysis provides an improvement in the symptoms of hepatic encephalopathy, a normalization of the values cannot be achieved as a consequence of the limited detoxification efficacy and high treatment costs.

Kreymann, U.S. Pat. Nos. 7,455,771; 8,480,899; and 9,039,896, and EP 1,867,354 B1, the disclosures of which are incorporated herein by reference in their entireties, describes a dialysis system and method, a dialysate regeneration unit, and a method for regenerating a dialysate. They further describe a means for dialyzing for removing protein-bound substances from a biological fluid, for instance, blood or blood plasma. The means contains at least one means for solubilizing protein-binding substances to be removed into the biological fluid and/or dialysis fluid, and a method for removing protein-bound substances from a biological fluid.

Kreymann et al., U.S. Pat. Nos. 8,377,308 and 8,574,438, and EP 2,214,752 B1, the disclosures of which are incorporated herein by reference in their entireties, describe an improved apparatus and method for regenerating a dialysate containing carrier substances. The dialysate regeneration units described therein are adapted for regenerating a dialysate containing one or more carrier substances. The dialysate regeneration units feature a first flow path and a second flow path. The first flow path features a first supply unit adapted for adding an acidic fluid to the dialysate flowing in the first flow path, and a detoxification unit located downstream of the first supply unit. The detoxification unit is adapted for removing toxins from the acidified dialysate flowing in the first flow path. The second flow path extends in parallel to the first flow path. The second flow path features a second supply unit adapted for adding an alkaline fluid to the dialysate flowing in the second flow path, and a further detoxification unit located downstream of the second supply unit. The further detoxification unit is adapted for removing toxins from the alkalized dialysate flowing in the second flow path.

A major issue with all extracorporeal blood treatment systems such as, for instance, hemodialysis systems, albumin-dialysis systems, hemodiafiltration systems, etc. is maintaining a fluid balance between fluids added to a patient and fluid withdrawn from the patient. A change in pressure and osmotic forces may result in water extraction from the patient during dialysis. IEC Norm No. 60601-2-16 3 (ed. 3.0) sub clause 201.12.4.4.103 requires that for chronic dialysis, the maximum deviation between fluid added to and fluid withdrawn from the dialysis system be ±400 ml in each 4 hour period. Therefore, fluid balancing devices attempt to ensure that the total volume of fluid pumped into and the total volume of fluid taken out of the non-blood side of a filter or dialysis system are equal. In some instances, extra fluid, especially water, may be withdrawn from a patient in excess of the amount of fluid added. This extra fluid removed may be referred to as an ultrafiltrate ("UF"). The ultrafiltrate may be added to the "waste" fluid withdrawn from the non-blood side of a dialysis system.

Weigel et al., U.S. Pat. No. 7,112,273, the disclosure of which is herein incorporated by reference, teach a balancing device for extracorporeal blood-circuits including a method and device for adjusting the volumetric flow for an extracorporeal blood treatment system. The device receives a pressure signal and calculates a compensation factor that is used to adjust the relative flow rates of the volumetrically balanced fluids. For example, in a hemofiltration system, the flow of waste and replacement fluid may be balanced volumetrically. Ultrafiltrate may be pumped in a bypass circuit in such a system. The rate of ultrafiltrate flow may be adjusted by the compensation signal. A disadvantage of this known device for balancing fluids is that a leakage in the extracorporeal fluid circuit of the extracorporeal blood treatment system may lead to incorrect balancing, which is not recognized by the system.

Peters et al., WO 2015/074973, the disclosure of which is herein incorporated by reference, teach a device and method for balancing fluids in an extracorporeal blood treatment device featuring a blood treatment unit. The device and method are based on monitoring an inner fluid system. The inner fluid system features a blood treatment unit, and an outer fluid system. The outer fluid system supplies the inner fluid system with fresh fluid and/or removes waste liquid from it. The balancing device includes a scale for balancing the fresh liquid as well as the filtrate. The balancing device features a monitoring device having a processing unit. The monitoring device is configured such that the volume, or a variable of the liquid correlated with the volume supplied to a balancing support is compared with the volume or with the volume-correlated variable of the liquid to be removed from the balancing support. On the basis of the ratio of the volume or of the volume-correlated variable of the fluid supplied to or removed from the balancing support, an incorrect balancing may be identified. A disadvantage of this device for balancing fluids is that a leakage in the extracorporeal fluid circuit of the extracorporeal blood treatment system may lead to incorrect balancing that may not be recognized by the system.

One prior art system for dialysis, the MARS system by Gambro features a liver dialysis system and method. The dialysis is performed using a recirculating system to recycle the dialysis liquid. However, the dialysis circuit and the recirculating system are not separated or decoupled. Accordingly, it is an object of the present invention to provide a dialysis apparatus or system featuring a balancing system or apparatus or component therein useful for balancing the volume or flow of fluids within the system that avoids the disadvantages of the prior art. It is a further object of the present invention to provide a diaysis method featuring improved methods for balancing the flow of or volume of fluids in a dialysis apparatus or system.

SUMMARY OF THE INVENTION

The present invention provides an apparatus or a dialysis apparatus or system including a regeneration unit adapted for regenerating a dialysate containing carrier substances and a system, means or unit for balancing the total volume of or flow of a fluid or multiple fluids within the dialysis system. The invention further provides a method for dialyzing a subject and a method for balancing the volume or flow of a fluid or multiple fluids within a dialysis apparatus or system, as well as methods of treating certain diseases.

In a first aspect, the invention provides a method for removing an unwanted substance from a biological fluid in an apparatus or a system suitable for dialyzing a biological fluid containing a protein-binding substance to be removed, comprising a) dialyzing a biological fluid against a dialysis fluid containing an adsorber for a protein-binding substance to be removed through a semipermeable membrane, b) adjusting the dialysis fluid so that the binding affinity of the adsorber for the protein-bound substance to be removed is lowered and the substance to be removed passes into solution, and c) balancing the volume or flow of one or more fluids in the apparatus or system suitable for dialyzing a biological fluid containing a protein-binding substance to be removed.

The adjusting the dialysis fluid in such a way that the binding affinity of the adsorber for the protein-bound substance may be performed by adding an acid, a base or a dialyzable substance, by dilution, by changing the salt content, by irradiation with waves or by heating, and the protein-binding substance to be removed may pass into solution. The biological fluid may be, for instance, blood or blood plasma, lymph fluid, cerebrospinal fluid or synovial fluid. The adsorber may be albumin such as human serum albumin, and the albumin may be present in the dialysis fluid in a concentration of, for instance, about 1-25 g per 100 ml, preferably of 1-10 g per 100 ml, and particularly preferably 1-3 g per 100 ml. In some instances, hydrochloric acid may be the acid, and sodium hydroxide may be the base. Also, in some instances, the method may further feature adding one or more dialyzable compound suitable for binding to the protein-binding substance to be removed to the dialysis fluid and/or the biological fluid. The one or more dialyzable compound may be, for instance, caffeine or a chelating agent for a metal cation such as, for instance, penicillamine, trientine, deferoxamine, preferiprone, HBED, vitamin C, BAL, DMPS or DMSA.

The balancing the volume or flow of one or more fluids in the apparatus or system suitable for dialyzing a biological fluid containing a protein-binding substance to be removed may be performed by measuring the weight of one or more fluids, or even all fluids, within the dialysis apparatus or system. The balancing the volume of or flow of one or more fluids may be effective to maintain a relatively constant volume of fluid within the apparatus or system. The relatively constant volume may be, for instance, within 10%, 5%, 4%, 3%, 2%, 1% or even 0.5% or 0.2% or 0.1% of the initial operating volume before the dialysis apparatus or system begins operating. The relatively constant volume may also be a deviation of less than 0.5, 0.25, 0.10, 0.05, 0.025 or 0.01 liter in a 24 or 48 hour dialysis period.

The balancing may feature adjusting or interrupting operation of the apparatus or system suitable for dialyzing a biological fluid containing a protein-binding substance when a deviation of the initial system weight in excess of a predefined threshold is detected. The adjusting or interrupting operation may be performed using one or more pumps provided within the apparatus or system to adjust the flow of one or more fluid. The one or more fluid may be any fluid that may be used within the apparatus or system, for instance, a dialysate, a filtrate, an ultrafiltrate, or a solution of an acid, a base, or a dialyzable compound.

The balancing may be performed using a balancing apparatus or system featuring a balancing support or container having at least a first reservoir for a first fluid that includes a usable fluid for the apparatus and system suitable for dialyzing a biological fluid containing a protein-binding substance to be removed, such as a dialysis fluid, and a second reservoir for a second fluid that may include a waste fluid from the apparatus and system suitable for dialyzing a biological fluid containing a protein-binding substance to be removed. The first reservoir may have at least one fluid outlet for fluid communication with the apparatus or system suitable for dialyzing a biological fluid containing a protein-binding substance to be removed. The second reservoir may contain at least one fluid in fluid communication with the dialysis apparatus or system. The balancing apparatus or system may further feature a weighing means for weighing the balancing support or container, and a controller configured to receive weighing data from the weighing means. The balancing support or container having at least the first and the second reservoir contained therein may be brought in weighing contact with load cells of a weighing means that is in data communication with the controller. The balancing apparatus or system may be suitable for balancing the total fluid volume within the apparatus or a system suitable for dialyzing a biological fluid containing a protein-binding substance to be removed. The total fluid volume may include the usable fluid such as a dialysis fluid and a waste fluid from the subject or patient undergoing the dialysis.

The balancing may include measuring the total weight of the balancing support or container including the at least first and second reservoirs, for instance using the weighing means, before the dialysis apparatus or system begins operating, to define an initial system weight ($sw_0$) of the container. The container may include at least one, for instance, a third or fourth, additional reservoir for a further fluid such as, for instance, a concentrate of an active substance for the dialysis circuit. The methods also include controlling pumping means for the first reservoir fluid and the second reservoir fluid such that the initial system weight is maintained, maintained with a predefined surplus, or maintained with a predefined loss.

The methods may further feature placing at least one further reservoir, for instance, a third or fourth or fifth, additional reservoir for a further fluid such as, for instance, a concentrate of an active substance for the dialysis circuit outside of the single container. A fluid outlet of the at least one further reservoir, for instance, a third or fourth, additional reservoir may be brought into fluid communication with the dialysis apparatus or system. As such, the methods may further feature measuring any fluid concentrate being provided from the further reservoir to the apparatus and system suitable for dialyzing a biological fluid containing a protein-binding substance to be removed volumetrically when the extracorporeal blood treatment circuit is in operation, calculating a weight of the fluid concentrate being provided to the apparatus and system suitable for dialyzing a biological fluid containing a protein-binding substance to be removed based on its density and provided volume any time when fluid concentrate is being provided to the apparatus and system suitable for dialyzing a biological fluid containing a protein-binding substance to be removed and recalculating the initial system weight of the container by adding the calculated weight of the fluid concentrate being provided to the apparatus and system suitable for dialyzing a biological fluid containing a protein-binding substance to be removed to obtain a redefined initial system weight.

While some reservoirs may be located outside of the fluid tight container that is being weighed by the weighing means, all amounts of fluids being provided into the dialysis apparatus or system are included in the balancing calculations. Hence, the present methods provide a substantially constantly corrected system weight that is substantially constantly compared to the weight of the container. Any waste or excess fluid obtained from a dialysis patient or subject is collected a (waste or filtrate) reservoir, for instance the second reservoir. Only fluid that is extracted from the patient (ultrafiltrate) or fluid that remains in the patient (bolus) is recognized by the balancing method. Such fluids are a surplus or a loss of the initial system weight. Thus, any possible measurement error is dramatically reduced.

In a second aspect, the invention provides an apparatus or a system suitable for dialyzing a biological fluid containing a protein-binding substance to be removed, featuring
 a) a biological fluid circuit (3);
 b) a dialysis fluid circuit (2);
 c) a means (4; 6; 7; 8; 9) for solubilizing the protein-binding substance to be removed;
 d) a dialysis, filtration or diafiltration device (5); and
 e) a balancing system or apparatus suitable for balancing the volume or flow of one or more fluids in the apparatus or system suitable for dialyzing a biological fluid containing a protein-binding substance to be removed.

The dialysis fluid in the apparatus or system may contain an adsorber, for instance, albumin such as human serum albumin, for the protein-binding substance to be removed from the biological fluid. The adsorber such as human serum albumin may be provided in a concentration of about 1-25 g per 100 ml, preferably of 1-10 g per 100 ml, and particularly preferably 1-3 g per 100 ml. The means (4; 6; 7; 8; 9) for solubilizing the protein-binding substance to be removed may feature one or two devices (4) for adjusting the pH of the dialysis fluid. The device (4) for adjusting the pH of dialysis fluid may be suitable for adding a base or for adding an acid. A first device (4) may adjust the pH of the dialysis fluid to pH=1-6.5, preferably pH=2.5-5. A second device (4) may adjust the pH of the dialysis fluid to pH=8-13. The first and second devices (4) for adjusting the pH may be arranged in the dialysis circuit in such a way that at least one device (5) for dialysis, filtration or diafiltration is provided downstream of the first device (4) and upstream of the second device (4). One, two, three or more other dialysis, filtration or diafiltration device (5) may be provided, for instance, in the biological fluid circuit (3).

The apparatus or a system suitable for dialyzing a biological fluid containing a protein-binding substance to be removed may further feature a second means (4; 6; 7; 8; 9) for solubilizing the protein-binding substance to be removed. The second means (4; 6; 7; 8; 9) for solubilizing a protein-binding substance to be removed may be a device (6) for adjusting the temperature of a fluid such as the biological fluid or the dialysis fluid, a device (7) for adding a substituate to dilute or change the salt content of the a fluid such as the dialysis fluid or biological fluid, a device (8) for adding a dialyzable compound binding to the protein-binding substance to be removed, or a device (9) for irradiating a fluid such as the dialysis fluid or biological fluid with waves. The device (6) for adjusting the temperature may be a heating or a cooling device, and the heating device (6) may feature a heating apparatus, a microwave apparatus or an infrared apparatus. The heating device (6) may be suitable for heating the biological fluid up to at least about 35° C., 40° C., or 45° C. Similarly, the cooling device (6) may feature a cooling unit. The device (6) for heating the fluid such as the dialysis fluid or the biological fluid and/or the device (6) for cooling the fluid such as the dialysis fluid or the biological fluid may be provided in the biological fluid circuit (3). The irradiating device (9) may be an ultrasonic apparatus, an electrical field or a magnetic field. Further, at least one means (4; 6; 7; 8; 9) for solubilizing the protein-binding substance to be removed may be provided in the biological fluid circuit (3). In some instances, the heating device (6) is provided downstream of a device (4) for adjusting the pH or a device (7) for adding substituate, and the heating device (6) may be provided upstream from the entrance to the dialysis fluid circuit (2) or the biological fluid circuit (3)

The balancing system or apparatus suitable for balancing the volume or flow of one or more fluids in the dialysis apparatus or system suitable for dialyzing a biological fluid containing a protein-binding substance to be removed may be adapted for and suitable for measuring the weight of one or more fluids, or even all fluids, within the dialysis apparatus or system. The system or device suitable for balancing the volume or flow of one or more fluids in the apparatus or system may be effective to maintain a relatively constant volume of fluid within the apparatus or system. The relatively constant volume may be, for instance, within 10%, 5%, 4%, 3%, 2%, 1% or even 0.5% or 0.2% or 0.1% of the initial operating volume before the dialysis apparatus or system begins operating. The relatively constant volume may also be a deviation of less than 0.5, 0.25, 0.10, 0.05, 0.025 or 0.01 liter in a 24 or 48 hour dialysis period.

The balancing apparatus or system suitable for balancing the volume or flow of one or more fluids in the apparatus or system may be suitable for adjusting or interrupting operation of the apparatus or system suitable for dialyzing a biological fluid containing a protein-binding substance when a deviation of the initial system weight in excess of a predefined threshold is detected. The adjusting or interrupting operation may be performed using one or more pumps provided within the apparatus or system to adjust the flow of one or more fluid. The one or more fluid may be any fluid that may be used within the apparatus or system, for instance, a dialysate, a filtrate, an ultrafiltrate, or a solution of an acid, a base, or a dialyzable compound.

The balancing apparatus or system may feature a balancing support or container having at least a first reservoir for a first fluid that includes a usable fluid for the apparatus and system suitable for dialyzing a biological fluid containing a protein-binding substance to be removed, such as a dialysis fluid, and a second reservoir for a second fluid that may include a waste fluid from the apparatus and system suitable for dialyzing a biological fluid containing a protein-binding substance to be removed. The first reservoir may have at least one fluid outlet for fluid communication with the dialysis apparatus or system. The second reservoir may contain at least one fluid in fluid communication with the dialysis apparatus or system. The balancing apparatus or system may further feature a weighing means for weighing the balancing support or container, and a controller configured to receive weighing data from the weighing means. The balancing support or container having at least the first and the second reservoir contained therein may be brought in weighing contact with load cells of a weighing means that is in data communication with the controller. The balancing apparatus or system may be suitable for balancing the total fluid volume within the apparatus or a system suitable for dialyzing a biological fluid containing a protein-binding substance to be removed. The total fluid volume may include the usable fluid such as a dialysis fluid and a waste fluid from the subject or patient undergoing the dialysis.

The balancing apparatus or system suitable for balancing the volume or flow of one or more fluids in the dialysis apparatus or system may be suitable for measuring the total weight of the balancing support or container including the at least first and second reservoirs, for instance using the weighing means, before the dialysis apparatus or system begins operating, to define an initial system weight ($sw_0$) of the container. The container may include at least one, for instance, a third or fourth, additional reservoir for a further fluid such as, for instance, a concentrate of an active substance for the dialysis circuit. The balancing apparatus or system suitable for balancing the volume or flow of one or more fluids in the dialysis apparatus or system may also include pumping means for the first reservoir fluid and the second reservoir fluid such that the initial system weight is maintained, maintained with a predefined surplus, or maintained with a predefined loss.

The balancing apparatus or system suitable for balancing the volume or flow of one or more fluids in the apparatus or system may further feature at least one further reservoir, for instance, a third or fourth, additional reservoir for a further fluid such as, for instance, a concentrate of an active substance for the dialysis circuit outside of the single container. A fluid outlet of the at least one further reservoir, for instance, a third or fourth, additional reservoir may be brought into fluid communication with the dialysis apparatus or system. As such, the balancing apparatus or system suitable for balancing the volume or flow of one or more fluids in the apparatus or system may be suitable for measuring any fluid concentrate being provided from the further reservoir to the dialysis apparatus and system volumetrically when the extracorporeal blood treatment circuit is in operation, calculating a weight of the fluid concentrate being provided to the dialysis apparatus and system based on its density and provided volume any time when fluid concentrate is being provided to the dialysis apparatus and system and recalculating the initial system weight of the container by adding the calculated weight of the fluid concentrate being provided to the dialysis apparatus and system to obtain a redefined initial system weight.

While some reservoirs may be located outside of the fluid tight container that is being weighed by the weighing means, all amounts of fluids being provided into the dialysis apparatus or system are included in the balancing calculations. Hence, the present balancing apparatus or system suitable for balancing the volume or flow of one or more fluids in the dialysis apparatus or system is effective in providing a substantially constantly corrected system weight that is substantially constantly compared to the weight of the container or balancing support. Any waste or excess fluid obtained from a dialysis patient or subject is collected in a reservoir such as the second (waste or filtrate) reservoir. Only fluid that is extracted from the patient (ultrafiltrate) or fluid that remains in the patient (bolus) is recognized by the device suitable for balancing the volume or flow of one or more fluids in the apparatus or system. Such fluids are a surplus or a loss of the initial system weight. Thus, any possible measurement error is dramatically reduced.

In a third aspect, the invention provides a dialysis apparatus or system featuring
(a) a biological fluid circuit (3, 76);
(b) a dialysate circuit (2);
(c) a dialyzer (22A, 22B, 64A, 64B);
(d) a dialysate regeneration unit (29, 74); and
(e) a balancing apparatus or system suitable for balancing the volume or flow of one or more fluids in the dialysis apparatus or system.

The biological fluid may be, for instance, blood or blood plasma, lymph fluid, cerebrospinal fluid or synovial fluid. The dialysis apparatus or system may further feature a dialysate reservoir that may be part of the dialysate circuit. The dialysate regeneration unit may be adapted for withdrawing dialysate from the dialysate reservoir, for regenerating the dialysate, and for resupplying the regenerated dialysate to the dialysate reservoir. Similarly, the dialysate regeneration unit may be part of a separate dialysate regeneration circuit. Likewise, the dialysate regeneration unit may be adapted for regenerating the dialysate in a continuous operation or in an intermittent operation. Also, the dialysate regeneration unit may be integrated into the dialysate circuit.

The dialyzer may feature a biological fluid compartment that is part of the biological fluid circuit, a dialysate fluid compartment that is part of the dialysate circuit, and a semipermeable membrane separating the biological fluid compartment and the dialysate fluid compartment.

The dialysis apparatus or system may further feature a substitution unit adapted for supplying substitution fluid to the biological fluid or to the dialysate fluid. The substitution fluid may contain one or more of an electrolyte, a nutrient, or a buffer.

The dialysate regeneration unit (29, 74) for regenerating a dialysate containing carrier substances, may feature (a) a first flow path (37) featuring (i) a first supply unit adapted for adding an acidic fluid (39) to the dialysate flowing in the first flow path (37), (ii) a detoxification unit adapted for removing toxins from the acidified dialysate flowing in the first flow path (37), located downstream of the first supply unit; and (b) a second flow path (38) featuring (i) a second supply unit adapted for adding an alkaline fluid (41) to the dialysate flowing in the second flow path (38), and (ii) a further detoxification unit adapted for removing toxins from the alkalized dialysate flowing in the second flow path (38), located downstream of the second supply unit. The second flow path (38) may extend in parallel to the first flow path (37).

The acidic fluid added by the first supply unit may be at least one of hydrochloric acid, sulfuric acid, and acetic acid; and the alkaline fluid added by the second supply unit may be at least one of sodium hydroxide solution and potassium hydroxide solution. The first supply unit may be adapted for adjusting the pH of the dialysate in the first flow path to a pH between 1 and 7, preferably between 2.5 and 5.5. The second supply unit may be adapted for adjusting the pH of the dialysate in the second flow path to a pH between 7 and 13, preferably between 8 and 13. In some instances, by decreasing the pH of the dialysate in the first flow path, a concentration ratio of a toxin-carrier-complex to a free toxin and a free carrier substance is shifted in favor of the free toxin for at least one toxin present in the dialysate thereby increasing a concentration of the free toxins in the dialysate. Similarly, by increasing the pH of the dialysate in the second flow path, a concentration ratio of a toxin-carrier-complex to a free toxin and a free carrier substance may be shifted in favor of the free toxin for at least one toxin present in the dialysate, thereby increasing the concentration of the free toxin in the dialysate. The further detoxification unit may be adapted for at least partially removing a free toxin.

At least one of the first and the second flow path may further feature a temperature regulation unit located upstream of the detoxification unit. The temperature regulation unit may be adapted for increasing or decreasing the temperature of the dialysate. By changing, for instance increasing, the temperature of the dialysate, the concentration ratio of a toxin-carrier-complex to a free toxin and a free carrier substance may be shifted in favor of the free toxin for at least one toxin in the dialysate, thereby increasing a concentration of the free toxin in the dialysate.

The toxin may be one of a metabolic product, bilirubin, bile acid, a drug, an electrolyte, a hormone, a lipid, a vitamin, a phenol, a sulfate, a trace element, a mineral, or a gas. The carrier substance may be a protein such as, for instance, albumin, human serum albumin, animal albumin, genetically engineered albumin, a globulin, or a lipoprotein; a carbon particle; a glycoside; a nucleic acid (or a derivative thereof); a fatty acid; a fat; a carbon molecule; a nanoparticle; a memory plastic; a memory metal; a resin; a secondary plant substance or another complex compound derived from a natural source; a carbon hydrate or a synthetic compound, e.g. a polymer.

The detoxification unit and the further detoxification unit may be implemented as regeneration dialyzers, or as ultrafiltration devices, or as diafiltration devices. The detoxification unit and the further detoxification unit may each feature a filtration pump and a discharge conduit adapted for withdrawing a discharge fluid from the respective detoxification unit. The first flow path may feature a first pump adapted for pumping the dialysate through the first flow path. Likewise, the second flow path may comprise a second pump adapted for pumping the dialysate through the second flow path. The first and the second pump may operate independently of one another. In some instances, the acidified dialysate supplied by the first flow path may be merged with the alkalized dialysate supplied by the second flow path. Similarly, in some instances, when the acidified dialysate supplied by the first flow path is merged with the alkalized dialysate supplied by the second flow path, the acidified dialysate and the alkalized dialysate neutralize each other at least partially, some instances, by merging the acidified dialysate supplied by the first flow path with the alkalized dialysate supplied by the second flow path, a flow of regenerated dialysate is provided. The regenerated dialysate may have a pH value between 6 and 11, preferably between 6.9 and 9.4. The dialysate regeneration unit may further feature at least one sensor unit adapted for determining the pH value of the flow of regenerated dialysate.

The dialysate regeneration unit may further feature a plurality of switching valves. The switching valves may be set during a first phase of operation such that a first detoxification unit is included in the first flow path and a second detoxification unit is included in the second flow path. In some instances, during a second phase of operation, the switching valves may be set such that the second detoxification unit is included in the first flow path and the first detoxification unit is included in the second flow path. In some instances, the switching valves are operated such that the acidified dialysate is alternatingly supplied to a first detoxification unit and to a second detoxification unit, and the alkalized dialysate is alternatingly supplied to the second detoxification unit and to the first detoxification unit. Similarly, the switching valves may be switched periodically.

The balancing apparatus or system suitable for balancing the volume or flow of one or more fluids in the dialysis apparatus or system may be adapted for and suitable for measuring the weight of one or more fluids, or even all fluids, within the dialysis apparatus or system. The balancing apparatus or system suitable for balancing the volume or flow of one or more fluids in the dialysis apparatus or system may be effective to maintain a relatively constant volume of fluid within the dialysis apparatus or system. The relatively constant volume may be, for instance, within 10%, 5%, 4%, 3%, 2%, 1% or even 0.5% or 0.2% or 0.1% of the initial operating volume before the dialysis apparatus or system begins operating. The relatively constant volume may also be a deviation of less than 0.5, 0.25, 0.10, 0.05, 0.025 or 0.01 liter in a 24 or 48 hour dialysis period.

The balancing apparatus or system suitable for balancing the volume or flow of one or more fluids in the dialysis apparatus or system may be suitable for adjusting, modifying or interrupting operation of the dialysis apparatus or system when a deviation of the initial system weight in excess of a predefined threshold is detected. The adjusting, modifying or interrupting operation may be performed using one or more pumps provided within the balancing apparatus or system to adjust the flow of one or more fluid. The one or more fluid may be any fluid that may be used within the dialysis apparatus or system, for instance, a dialysate, a filtrate, an ultrafiltrate, or a solution of an acid, a base, or a dialyzable compound.

The balancing apparatus or system may feature a balancing support or container having at least a first reservoir for a first fluid that includes a usable fluid for the dialysis apparatus or system, such as a dialysis fluid, and a second reservoir for a second fluid that may include a waste fluid from the dialysis apparatus or system. The first reservoir may have at least one fluid outlet for fluid communication with the dialysis apparatus or system. The second reservoir may contain at least one fluid in fluid communication with the dialysis apparatus or system. The balancing apparatus or system may further feature a weighing means for weighing the balancing support or container, and a controller configured to receive weighing data from the weighing means. The balancing support or container having at least the first and the second reservoir contained therein may be brought in weighing contact with load cells of the weighing means that is in data communication with the controller. The balancing apparatus or system may be suitable for balancing the total fluid volume within the dialysis apparatus or system. The total fluid volume may include the usable fluid such as a dialysis fluid and a waste fluid from the subject or patient undergoing the dialysis.

The balancing system or apparatus suitable for balancing the volume or flow of one or more fluids in the dialysis apparatus or system may be suitable for measuring the total weight of the balancing support or container including the at least first and second reservoirs, for instance using the weighing means, before the dialysis apparatus or system begins operating, to define an initial system weight ($sw_0$) of the container. The container may include at least one, for instance, a third or fourth, additional reservoir for a further fluid such as, for instance, a concentrate of an active substance for the dialysis circuit. The balancing apparatus or system suitable for balancing the volume or flow of one or more fluids in the dialysis apparatus or system may also include pumping means for the first reservoir fluid and the second reservoir fluid such that the initial system weight is maintained, maintained with a predefined surplus, or maintained with a predefined loss.

The balancing apparatus or system suitable for balancing the volume or flow of one or more fluids in the dialysis apparatus or system may further feature at least one further reservoir, for instance, a third or fourth, additional reservoir for a further fluid such as, for instance, a concentrate of an active substance for the dialysis circuit outside of the single container. A fluid outlet of the at least one further reservoir, for instance, a third or fourth additional reservoir, may be brought into fluid communication with the dialysis apparatus or system. As such, the balancing apparatus or system suitable for balancing the volume or flow of one or more fluids in the dialysis apparatus or system may be suitable for measuring any fluid concentrate being provided from the further reservoir to the dialysis apparatus and system volumetrically when the dialysis apparatus or system is in operation, calculating a weight of the fluid concentrate being provided to the dialysis apparatus or system based on its density and volume provided any time when fluid concentrate is being provided to the dialysis apparatus or system and recalculating the initial system weight of the container by adding the calculated weight of the fluid concentrate being provided to the dialysis apparatus or system to obtain a redefined initial system weight.

While some reservoirs may be located outside of the fluid tight container that is being weighed by the weighing means, all amounts of fluids being provided into the dialysis apparatus or system are included in the balancing calculations. Hence, the present balancing apparatus or system suitable for balancing the volume or flow of one or more fluids in the dialysis apparatus or system is effective in providing a substantially constantly corrected system weight that is substantially constantly compared to the weight of the container or balancing support. Any waste or excess fluid obtained from a dialysis patient or subject is collected in a reservoir such as the second (waste or filtrate) reservoir. Only fluid that is extracted from the patient (ultrafiltrate) or fluid that remains in the patient (bolus) is recognized by the device suitable for balancing the volume or flow of one or more fluids in the dialysis apparatus or system. Such fluids are a surplus or a loss of the initial system weight. Thus, any possible measurement error is dramatically reduced.

In a fourth aspect, the invention provides an apparatus or system (90) for balancing the flow of fluids in a dialysis apparatus or system (160) featuring a container (100) having a receiving space for receiving (109) at least a first reservoir (101) for a first fluid usable in the dialysis apparatus or system (160) and a second reservoir (102) for a second fluid from the dialysis apparatus or system (160), wherein the first reservoir (101) has at least one fluid outlet (103) in fluid communication with the dialysis apparatus or system (160) and wherein the second reservoir has at least one fluid inlet (105) in fluid communication with the dialysis apparatus or system, a weighing means (130), and a controller (140) configured to receive data from the weighing means (130) for balancing the flow or volume of one or more fluid within the dialysis apparatus or system: The container (100) may have a receiving space. The receiving space may be, at least at its base and side walls substantially fluid tight. The container (100) may be formed of a substantially stiff structure, and it may be provided with a fluid tight lining formed of, formed of, for instance one or more material such as a fluid tight film, a foil, or a laminate. Further, the container (100) may be provided with a fluid tight coating (110) or with both a fluid tight coating (110) and a fluid tight lining (111). The maximum loading capacity of the receiving space of the container (100) normally exceeds the maximum load of the first reservoir (101) and the second reservoir (102) jointly, and the receiving space (109) of the container (100) may have a loading capacity of at least 80 liters, at least 100 liters or even at least 120 liters. The container (100) may be mobile and comprise at least 3 or 4 rollers (112) arranged at a base part (108) of the container (100), and at least one of these rollers (112) may be equipped with a break-member (114) for arresting movement of one or more rollers (112). The container (100) may be collapsible, and it may be thermally insulated.

The weighing means (130) may feature one or more load cells (132). The one or more load cells (132) may be associated with one of the rollers (112), and one or more load cells (132) is arranged between a roller (112) and a rigid point of application at the base part (108) of the container. The load cells (131) may also be located on a plunger-member (153).

In some instances, the container (100) may contain an interface (115) of the weighing means (130) for connecting the load cells (132) to the controller (140). The container (100) may contain one or more supporting elements (116) for locking and guiding fluid lines (104, 106) within the container (100), that connect the first and second reservoirs (101, 102) with the dialysis apparatus or system (160). Further, at least one of the first and second reservoirs (101, 102) or a further reservoir may be equipped with a gas separator. The fluid outlets (103) and the fluid inlets (105) of the reservoirs (101, 102) may be substantially resistant to bending and kinking. Also, a support housing (150) may be provided for the container (100, 100.1). The support housing (150) may have two sidewalls (152.1, 152.2) arranged on two opposite sides of an entrance opening (151) of the support housing (150). At least one load cell (131) may be associated with each of said sidewalls (152.1, 152.2) for weighing contact with at least one rigid point of application (81) of the container (100, 100.1). Some or all of the load cells (131) may be located on a plunger-member (153). The plunger-members (153) may in turn be connected to the respective sidewall (152.1, 152.2) and may be linearly movable between a first and a second position (154.1, 154.2). Likewise, the plunger-members (153) may be arrested in one or more directions perpendicular to the direction of linear movement by means of one or more locking members (155.1, 155.2), at least in a second position (154.2). The weighing means (130) may feature a weighing plate (133) arranged in the support housing (150), and the weighing plate (133) may form a floor of the support housing (150) on which the container (100, 100.1) may be located.

The apparatus or system for balancing may feature a third reservoir, a fourth reservoir, a fifth reservoir or even other additional reservoirs (93, 94, 95, 96), and such third, fourth, fifth or other additional reservoirs may be provided in the receiving space (109) of the container (100) or outside the container. One or more of the third, fourth, fifth or other additional reservoirs (93, 94, 95) may be suitable for containing a solution useful for adjusting the pH of a fluid, a solution useful as a component of a dialysate, an ultrafiltrate, a solution useful as a stabilizer for a component of a dialysate such as, for instance, albumin or glucose. The dialysate may be recirculated into the apparatus or dialysis apparatus or system. Outflows from one or more of the first, second, third, fourth, fifth or other additional reservoirs (e.g. 103, 105) may be positioned at substantially the lowest points of the respective reservoirs. One or more reservoir may further feature one or more port. The one or more port may be adapted to contain an instrument useful for measuring the pH, concentration, density or the temperature of a fluid contained therein or for suctioning air or fluid from the reservoir. Similarly, an instrument useful for measuring the pH, concentration, density or the temperature of a fluid or for suctioning air or fluid may be provided within one or more tubes or connections within the apparatus or system for balancing. The reservoirs may be readily exchangeable, and they may be sized and adapted to being changed after, for instance, 4-8 hours, 10 hours, 12 hours, 24 hours or 48 hours.

The controller (140) may be adapted to interrupt, modify or adjust operation of the dialysis apparatus or system upon deviation of a measured balanced weight in excess of a predefined threshold. Deviation of a measured balanced weight in excess of a predefined threshold may be repeatedly, substantially continuously or even continuously measured. Thus, the controller may be operable to facilitate various or different flow rates of one or more fluids such as a dialysis fluid, dialysate, concentrate or substituate within the dialysis apparatus or system.

The balancing apparatus or system may feature one or more pumps (e.g. 101.1, 102.1), and one or more of these pumps may be substantially closed pumps. One or more pumps may be operable to pump dialysate from the first reservoir to the dialysis apparatus or system. Likewise, one or more of the pumps may be operable to pump ultrafiltrate from the dialysis apparatus or system to the second reservoir.

In a fifth aspect, the invention provides a container (100, 100.1) suitable for use in a system for balancing the volume or flow of fluids in a dialysis apparatus or system. The container may be substantially fluid tight at its base part (108) and side walls (118, 119.1, 119.2) and adapted for being weighed by a weighing means (130). The container may have a receiving space (109) for receiving at least a first and a second reservoir (101, 102). The maximum loading capacity of the receiving space (109) may exceed the maximum load of the first reservoir (101) and the second reservoir (101) jointly. The container (100, 100.1) may have a stiff structure, it may be collapsible, and it may be thermally insulated. The stiff structure may be provided with a fluid tight lining (111) formed from one or more materials from among a fluid tight film, a foil and a laminate. The stiff structure may also be provided with a fluid tight coating (110), and in some instances, the stiff structure is provided with both a fluid tight coating (110) and a fluid tight lining (111). The receiving space (109) may have a loading capacity of at least 80 liters, at least 100 liters or at least 120 liters.

The container (100, 100.1) may be mobile, and may have at least 2 or 3 or 4 rollers (112) arranged at a base part (108) of the container (100, 100.1). One or more of the rollers (112) may be equipped with a break-member (114) for arresting the at least one roller (112). The container (100, 100.1) may further contain one or more load cells (132) useful in the weighing means (130), and one or more of the load cells (132) may be associated with one of the rollers (112). The respective load cell (132) may be arranged in between a roller (112) and a rigid point of application (81) at the base part (108) of the container (100, 100.1). In fact, each of the load cells (132) may be associated with one of the rollers (112), and each of the load cells (132) may be arranged in between a roller (112) and a rigid point of application (81) at the base part (108) of the container (100, 100.1). Likewise, each of the load cells (132) may be integrated in the rollers (112).

The container (100, 100.1) may feature an interface (115) of the weighing means (130) for connecting load cells (132, 133) of the container (100, 100.1) to a controller (140). The container (100, 100.1) may also feature one or more supporting elements (116) for locking and guiding one or more fluid lines (e.g. 104, 106) disposed within the container (100, 100.1). The fluid lines (104, 106) may be adapted to connect the first and second reservoirs (101, 102) with the dialysis apparatus or system (160).

The container (100, 100.1) may feature a door-member (117, 117.1, 117.2) arranged in a side wall (118, 119.1, 119.2) rising from the base part (108), and the door-member (117, 117.1, 117.2) may occupy at least 10% or 15% or 20% or 25% of the area of the side wall (118, 119.1, 119.2). The container (100, 100.1) may further feature a stiff cover element (120) that may be pivotally mounted at an end of the container (100, 100.1) opposite the base part (108), and a locking means (121.1, 121.2) disposed at the container (100, 100.1) to arrest the cover element (120) in non-pivotal position. The stiff cover element (120) may be furnished with at least one aperture (123). The container (100, 100.1) may further feature at least one partition (124.1) arranged inside the container (100, 100.1) to vertically or horizontally partition the receiving space of the container (100, 100.1) into separate compartments (125.1, 125.2). The partition (124.1) may have an inclination (a) with respect to at least one of the walls (118, 119.1, 119.2) of the container (100, 100.1). Also, the container (100, 100.1) may be positioned in a support housing (150).

In a sixth aspect, the invention provides a method for balancing the flow or volume of a fluid in a dialysis apparatus or system featuring
  (a) Measuring the total weight of fluids present in the dialysis apparatus or system before the dialysis apparatus or system is operating;
  (b) Measuring the total weight of one or more fluids added to the dialysis apparatus or system during operation; and
  (c) Adjusting the flow of one or more fluids within the dialysis apparatus or system.

The measuring the total weight of one or more fluids added to a dialysis apparatus or system during operation may be performed by directly measuring the weight of such one or more fluids or may be performed volumetrically by directly measuring the volume of such one or more fluids added and converting the volume measurement to a weight measurement by well known calculations.

The method may feature placing at least a first reservoir (101) for a first fluid usable in the dialysis apparatus or system (160) and a second reservoir (102) for a second fluid from the dialysis apparatus or system in a container (100). A fluid outlet of the first reservoir (101) and a fluid inlet of the second reservoir (102) may be brought into fluid communication with the dialysis apparatus or system (170). The container may be positioned in weighing contact with a weighing means (130), and the weighing means (130) may be arranged in data communication with a controller (140). The method further features measuring the total weight of the container (100) including the at least first (101) and second reservoirs (102) before the dialysis apparatus or system is operating thereby defining an initial system weight ($sw_0$) of the container (100). The method further features controlling pumping means (102.1, 102.2) for the first fluid and the second fluid to maintain the initial system weight ($sw_0$, $sw_r$), maintain the initial system weight ($sw_0$, $sw_r$) with a predefined surplus (UF), or maintain the initial system weight ($sw_0$, $sw_r$) with a predefined loss (L). Operation of the biological fluid circuit (170) may be adjusted or interrupted when a deviation of the initial system weight ($sw_0$, $sw_r$) in excess of a predefined threshold (T) is detected by the controller.

The method may further feature placing at least one additional reservoir (93, 94, 95) for an additional fluid, for instance a concentrate of an active substance usable in the dialysis apparatus or system outside the single container (100). In such instances, a fluid outlet of the further reservoir (93, 94, 95) is normally brought into fluid communication with the dialysis apparatus or system. The method may in such instances further feature measuring any fluid from the further reservoir (93, 94, 95) to the dialysis apparatus or system volumetrically when the dialysis apparatus or system is operating. As such, the method may feature calculating a weight of a fluid, such as a fluid usable in the dialysis apparatus or system, for instance an acid or base fluid concentrate based on its density and volume supplied. Likewise, the method may feature recalculating the initial system weight of the container including adding the calculated weight of the fluid, such as a fluid usable in the dialysis apparatus or system, for instance an acid or base fluid concentrate, added to the dialysis apparatus or system thereby providing a redefined initial system weight ($sw_r$).

In a seventh aspect, the invention provides a method for dialyzing a subject in need thereof comprising
  a) passing a biological fluid from the subject through a biological fluid circuit;
  b) dialyzing the biological fluid against a dialysis fluid containing an adsorber for a protein-binding substance to be removed through a semipermeable membrane,
  c) adjusting the dialysis fluid so that the binding affinity of the adsorber for the protein-bound substance to be removed is lowered and the substance to be removed passes into solution, and
  d) balancing the volume or flow of one or more fluids in the apparatus or system suitable for dialyzing a biological fluid containing a protein-binding substance to be removed wherein the fluid volume of the subject remains substantially constant.

The adjusting the dialysis fluid in such a way that the binding affinity of the adsorber for the protein-bound substance may be performed by adding an acid, a base or a dialyzable substance, by dilution, by changing the salt content, by irradiation with waves or by heating, and the protein-binding substance to be removed may pass into solution. The biological fluid may be, for instance, blood or blood plasma, lymph fluid, cerebrospinal fluid or synovial fluid. The adsorber may be albumin such as, human serum albumin, and the albumin may be present in the dialysis fluid in a concentration of, for instance, about 1-25 g per 100 ml, preferably of 1-10 g per 100 ml, and particularly preferably 1-3 g per 100 ml. In some instances, hydrochloric acid may be the acid, and sodium hydroxide may be the base. Also, in some instances, the method may further feature adding one or more dialyzable compound suitable for binding to the protein-binding substance to be removed to the dialysis fluid and/or the biological fluid. The one or more dialyzable compound may be, for instance, caffeine or a chelating agent for a metal cation such as, for instance, penicillamine, trientine, deferoxamine, preferiprone, HBED, vitamin C, BAL, DMPS or DMSA.

The balancing the volume or flow of one or more fluids in the apparatus or system suitable for dialyzing a biological fluid containing a protein-binding substance to be removed may be performed by measuring the weight of one or more fluids, or even all fluids, within the dialysis apparatus or system. The balancing the volume of or flow of one or more fluids may be effective to maintain a relatively constant volume of fluid within the apparatus or system. The relatively constant volume may be, for instance, within 10%, 5%, 4%, 3%, 2%, 1% or even 0.5% or 0.2% or 0.1% of the initial operating volume before the dialysis apparatus or system begins operating. The relatively constant volume may also be a deviation of less than 0.5, 0.25, 0.10, 0.05, 0.025 or 0.01 liter in a 24 or 48 hour dialysis period.

The balancing may feature adjusting or interrupting operation of the apparatus or system suitable for dialyzing a biological fluid containing a protein-binding substance when a deviation of the initial system weight in excess of a predefined threshold is detected. The adjusting or interrupting operation may be performed using one or more pumps provided within the apparatus or system to adjust the flow of one or more fluid. The one or more fluid may be any fluid that may be used within the apparatus or system, for instance, a dialysate, a filtrate, an ultrafiltrate, or a solution of an acid, a base, or a dialyzable compound.

The balancing may be performed using a balancing apparatus or system featuring a balancing support or container having at least a first reservoir for a first fluid that includes a usable fluid for the apparatus and system suitable for dialyzing a biological fluid containing a protein-binding substance to be removed, such as a dialysis fluid, and a second reservoir for a second fluid that may include a waste fluid from the apparatus and system suitable for dialyzing a biological fluid containing a protein-binding substance to be removed. The first reservoir may have at least one fluid outlet for fluid communication with the apparatus or system suitable for dialyzing a biological fluid containing a protein-binding substance to be removed. The second reservoir may contain at least one fluid inlet in fluid communication with the dialysis apparatus or system. The balancing apparatus or system may further feature a weighing means for weighing the balancing support or container, and a controller configured to receive weighing data from the weighing means. The balancing support or container having at least the first and the second reservoir contained therein may be brought in weighing contact with load cells of a weighing means that is in data communication with the controller. The balancing apparatus or system may be suitable for balancing the total fluid volume within the apparatus or a system suitable for dialyzing a biological fluid containing a protein-binding substance to be removed. The total fluid volume may include the usable fluid such as a dialysis fluid and a waste fluid from the subject or patient undergoing the dialysis.

The balancing may include measuring the total weight of the balancing support or container including the at least first and second reservoirs, for instance using the weighing means, before the dialysis apparatus or system begins operating, to define an initial system weight ($sw_0$) of the container. The container may include at least one, for instance, a third or fourth, additional reservoir for a further fluid such as, for instance, a concentrate of an active substance for the dialysis circuit. The methods also include controlling pumping means for the first reservoir fluid and the second reservoir fluid such that the initial system weight is maintained, maintained with a predefined surplus, or maintained with a predefined loss.

The methods may further feature placing at least one further reservoir, for instance, a third or fourth, additional reservoir for a further fluid such as, for instance, a concentrate of an active substance for the dialysis circuit outside of the single container. A fluid outlet of the at least one further reservoir, for instance, a third or fourth, additional reservoir may be brought into fluid communication with the dialysis apparatus or system. As such, the methods may further feature measuring any fluid concentrate being provided from the further reservoir to the apparatus and system suitable for dialyzing a biological fluid containing a protein-binding substance to be removed volumetrically when the extracorporeal blood treatment circuit is in operation, calculating a weight of the fluid concentrate being provided to the apparatus and system suitable for dialyzing a biological fluid containing a protein-binding substance to be removed based on its density and provided volume any time when fluid concentrate is being provided to the apparatus and system suitable for dialyzing a biological fluid containing a protein-binding substance to be removed and recalculating the initial system weight of the container by adding the calculated weight of the fluid concentrate being provided to the apparatus and system suitable for dialyzing a biological fluid containing a protein-binding substance to be removed to obtain a redefined initial system weight.

While some reservoirs may be located outside of the fluid tight container that is being weighed by the weighing means, all amounts of fluids being provided into the dialysis apparatus or system are included in the balancing calculations. Hence, the present methods provide a substantially constantly corrected system weight that is substantially constantly compared to the weight of the container. Any waste or excess fluid obtained from a dialysis patient or subject is collected a (waste or filtrate) reservoir, for instance the second reservoir. Only fluid that is extracted from the patient (ultrafiltrate) or fluid that remains in the patient (bolus) is recognized by the balancing method. Such fluids are a surplus or a loss of the initial system weight. Thus, any possible measurement error is dramatically reduced.

In an eighth aspect, the invention provides a method for treating a disease characterized by unwanted accumulation of a protein-binding substance in a biological fluid comprising a) passing a biological fluid from the subject through a biological fluid circuit;

b) dialyzing the biological fluid against a dialysis fluid containing an adsorber for the protein-binding substance to be removed through a semipermeable membrane, c) adjusting the dialysis fluid so that the binding affinity of the adsorber for the protein-bound substance to be removed is lowered and the substance to be removed passes into solution, and d) balancing the volume or flow of one or more fluids in the apparatus or system suitable for dialyzing a biological fluid containing a protein-binding substance to be removed wherein the fluid volume of the subject remains substantially constant.

The disease characterized by unwanted accumulation of a protein-binding substance in a biological fluid may be a hepatic or kidney disease, such as, for instance, hepatoencephalopathy, cirrhosis or liver failure. The adjusting the dialysis fluid in such a way that the binding affinity of the adsorber for the protein-bound substance may be performed by adding an acid, a base or a dialyzable substance, by dilution, by changing the salt content, by irradiation with waves or by heating, and the protein-binding substance to be removed may pass into solution. The biological fluid may be, for instance, blood or blood plasma, lymph fluid, cerebrospinal fluid or synovial fluid. The adsorber may be albumin such as human serum albumin, and the albumin may be present in the dialysis fluid in a concentration of, for instance, about 1-25 g per 100 ml, preferably of 1-10 g per 100 ml, and particularly preferably 1-3 g per 100 ml. In some instances, hydrochloric acid may be the acid, and sodium hydroxide may be the base. Also, in some instances, the method may further feature adding one or more dialyzable compound suitable for binding to the protein-binding substance to be removed to the dialysis fluid and/or the biological fluid. The one or more dialyzable compound may be, for instance, caffeine or a chelating agent for a metal cation such as, for instance, penicillamine, trientine, deferoxamine, preferiprone, HBED, vitamin C, BAL, DMPS or DMSA.

The balancing the volume or flow of one or more fluids in the apparatus or system suitable for dialyzing a biological fluid containing a protein-binding substance to be removed may be performed by measuring the weight of one or more fluids, or even all fluids, within the dialysis apparatus or system. The balancing the volume of or flow of one or more fluids may be effective to maintain a relatively constant volume of fluid within the apparatus or system. The relatively constant volume may be, for instance, within 10%, 5%, 4%, 3%, 2%, 1% or even 0.5% or 0.2% or 0.1% of the initial operating volume before the dialysis apparatus or system begins operating. The relatively constant volume may also be a deviation of less than 0.5, 0.25, 0.10, 0.05, 0.025 or 0.01 liter in a 24 or 48 hour dialysis period.

The balancing may feature adjusting or interrupting operation of the apparatus or system suitable for dialyzing a biological fluid containing a protein-binding substance when a deviation of the initial system weight in excess of a predefined threshold is detected. The adjusting or interrupting operation may be performed using one or more pumps provided within the apparatus or system to adjust the flow of one or more fluid. The one or more fluid may be any fluid that may be used within the apparatus or system, for instance, a dialysate, a filtrate, an ultrafiltrate, or a solution of an acid, a base, or a dialyzable compound.

The balancing may be performed using a balancing apparatus or system featuring a balancing support or container having at least a first reservoir for a first fluid that includes a usable fluid for the apparatus and system suitable for dialyzing a biological fluid containing a protein-binding substance to be removed, such as a dialysis fluid, and a second reservoir for a second fluid that may include a waste fluid from the apparatus and system suitable for dialyzing a biological fluid containing a protein-binding substance to be removed. The first reservoir may have at least one fluid outlet for fluid communication with the apparatus or system suitable for dialyzing a biological fluid containing a protein-binding substance to be removed. The second reservoir may contain at least one fluid in fluid communication with the dialysis apparatus or system. The balancing apparatus or system may further feature a weighing means for weighing the balancing support or container, and a controller configured to receive weighing data from the weighing means. The balancing support or container having at least the first and the second reservoir contained therein may be brought in weighing contact with load cells of a weighing means that is in data communication with the controller. The balancing apparatus or system may be suitable for balancing the total fluid volume within the apparatus or a system suitable for dialyzing a biological fluid containing a protein-binding substance to be removed. The total fluid volume may include the usable fluid such as a dialysis fluid and a waste fluid from the subject or patient undergoing the dialysis.

The balancing may include measuring the total weight of the balancing support or container including the at least first and second reservoirs, for instance using the weighing means, before the dialysis apparatus or system begins operating, to define an initial system weight ($sw_0$) of the container. The container may include at least one, for instance, a third or fourth, additional reservoir for a further fluid such as, for instance, a concentrate of an active substance for the dialysis circuit. The methods also include controlling pumping means for the first reservoir fluid and the second reservoir fluid such that the initial system weight is maintained, maintained with a predefined surplus, or maintained with a predefined loss.

The methods may further feature placing at least one further reservoir, for instance, a third or fourth, additional reservoir for a further fluid such as, for instance, a concentrate of an active substance for the dialysis circuit outside of the single container. A fluid outlet of the at least one further reservoir, for instance, a third or fourth, additional reservoir may be brought into fluid communication with the dialysis apparatus or system. As such, the methods may further feature measuring any fluid concentrate being provided from the further reservoir to the apparatus and system suitable for dialyzing a biological fluid containing a protein-binding substance to be removed volumetrically when the extracorporeal blood treatment circuit is in operation, calculating a weight of the fluid concentrate being provided to the apparatus and system suitable for dialyzing a biological fluid containing a protein-binding substance to be removed based on its density and provided volume any time when fluid concentrate is being provided to the apparatus and system suitable for dialyzing a biological fluid containing a protein-binding substance to be removed and recalculating the initial system weight of the container by adding the calculated weight of the fluid concentrate being provided to the apparatus and system suitable for dialyzing a biological fluid containing a protein-binding substance to be removed to obtain a redefined initial system weight.

While some reservoirs may be located outside of the fluid tight container that is being weighed by the weighing means, all amounts of fluids being provided into the dialysis apparatus or system are included in the balancing calculations. Hence, the present methods provide a substantially constantly corrected system weight that is substantially constantly compared to the weight of the container. Any waste or excess fluid obtained from a dialysis patient or subject is collected a (waste or filtrate) reservoir, for instance the second reservoir. Only fluid that is extracted from the patient (ultrafiltrate) or fluid that remains in the patient (bolus) is recognized by the balancing method. Such fluids are a surplus or a loss of the initial system weight. Thus, any possible measurement error is dramatically reduced.

BRIEF DESCRIPTION OF THE FIGURES

FIG. 6 provides a more detailed view of dialysis apparatus or system.

DETAILED DESCRIPTION OF THE PREFERRED EMBODIMENTS

Figure 1:
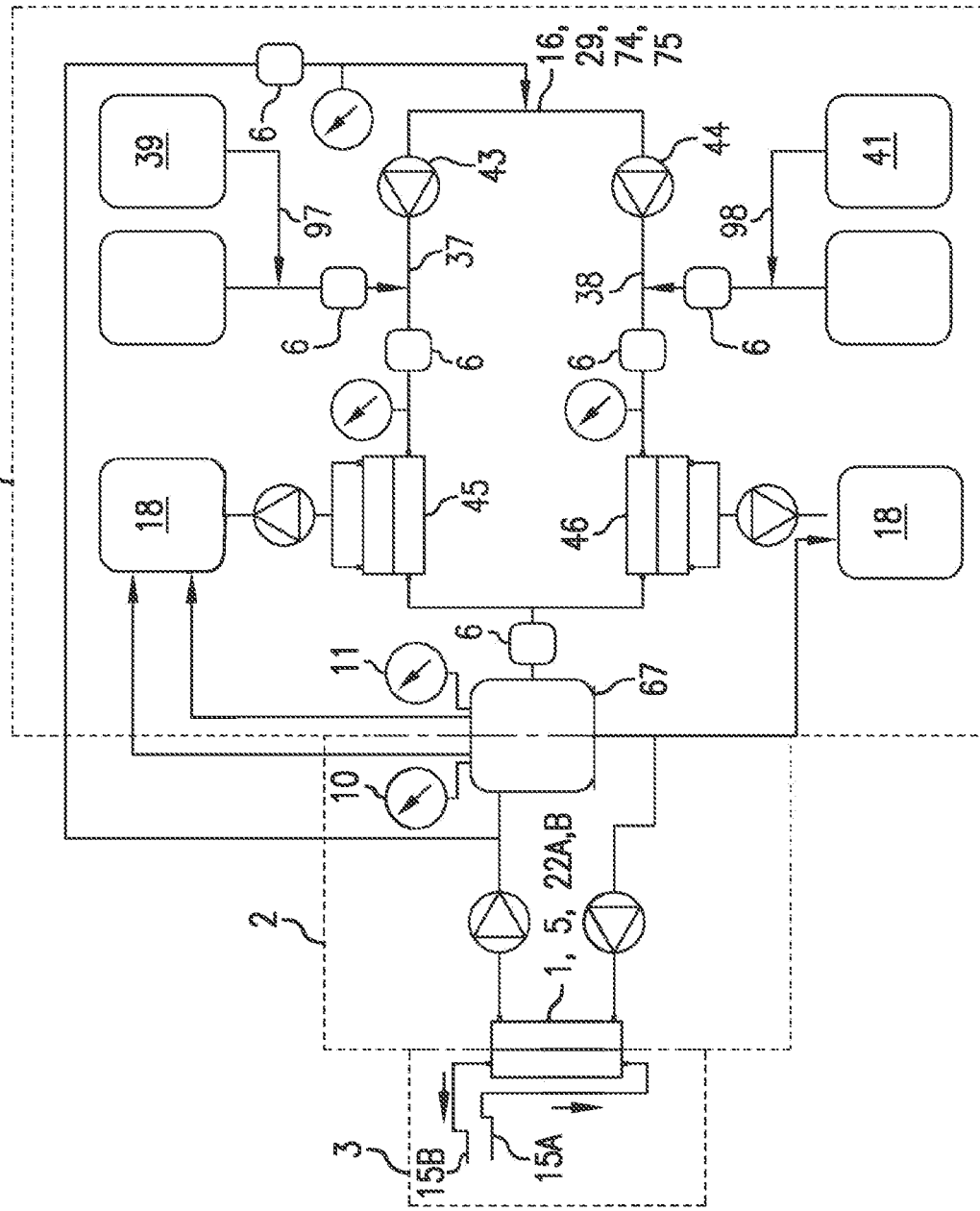
FIG. 1 is a diagrammatic representation of a dialysis apparatus or system as described herein featuring a bilogical fluid circuit, a dialysis circuit having a dialyzer, a dialysate regeneration unit and a balancing apparatus or system. Further, means are provided for adjusting the pH and temperature of a fluid within the dialysis apparatus or system.

The present methods and systems feature the following elements and steps. Further features of the invention, its nature and various advantages become more apparent from the accompanying drawings and the following detailed description of the preferred embodiments.

A Protein-Binding Substance to be Removed

By "a protein-binding substance" or "a protein-binding substance to be removed" is meant any molecule or component thereof, large or small, that binds to a protein, such as, for instance, albumin. The binding may be specific or non-specific, and it may be with great, significant or weak affinity. The protein may be, for instance, albumin, such as human serum albumin. Hence, the terms "a protein-binding substance" or "a protein-binding substance to be removed" include any molecule or component thereof, large or small, that binds to albumin such as human serum albumin with any measurable or observable affinity. A detailed description of such substances that bind to albumin is provided by Peters, T. "All About Albumin: Biochemistry, Genetics, and Medical Applications," 1995; New York: Academic Press, Chapter 3. Exemplary protein-binding substance to be removed also include protons (H+), hydroxide ions (OH—), and gases, such as, for instance, $O_2$, $CO_2$, $N_2$, Ar, CO, He, $N_2$, Ne and $CH_4$.

Fasano, *Life* 2005; 57(12): 787-796 teaches the ligand binding properties of human serum albumin. Human serum albumin is the most prominent protein in plasma, binds different classes of ligands at multiple sites. Human serum albumin provides a depot for many compounds, affects pharmacokinetics of many drugs, holds some ligands in a strained orientation providing their metabolic modification, renders potential toxins harmless transporting them to disposal sites, accounts for most of the antioxidant capacity of human serum. The globular domain structural organization of monomeric human serum albumin is at the root of its allosteric properties which are reminiscent of those of multimeric proteins.

Table 1 provides a list of some exemplary molecules or components thereof within the scope of the terms "a protein-binding substance" or "a protein-binding substance to be removed," together with some reported association constants.

TABLE 1

| Compound | Association constant, $K_A$ ($M^{-1}$) |
|---|---|
| Long-chain fatty acids° | (1-69) × $10^7$ |
| Eicosanoids ($PGE_1$) | 7 × $10^4$ |
| Bile acids Steroids | (3-200) × $10^3$ |
| Cortisol | 5 × $10^3$ |
| Progesterone | 3.6 × $10^5$ |
| Testosterone | 2.4 × $10^4$ |
| Aldosterone | 3.2 × $10^3$ |
| Bilirubin | 9.5 × $10^7$ |
| Hematin | 1.1 × $10^8$ |
| L-Thyroxine | 1.6 × $10^6$ |

TABLE 1-continued

| Compound | Association constant, $K_A$ ($M^{-1}$) |
|---|---|
| L-tryptophan | $1.0 \times 10^4$ |
| 25,OH—VitaminD3 | $6 \times 10^5$ |
| t-25-(OH)$_2$—Vitamin D3 | $5 \times 10^4$ |
| Aquocobalamin | $2 \times 10^7$ |
| Folate | $9 \times 10^2$ |
| Ascorbate | $3.5 \times 10^4$ |
| Copper(II) | $1.5 \times 10^{16}$ |
| Zinc(II) | $3.4 \times 10^7$ |
| Calcium | $15.1 \times 10^2$ |
| Magnesium | $1 \times 10^2$ |
| Chloride | $7.2 \times 10^2$ |

Some examples of endogenous ligands of albumin include, for instance, aliphatic fatty acids (Bhattacharya et al., (2000) *J. Mol. Biol.* 303:721-732; Petitpas, et al., (2001) *J. Mol. Biol.* 314:955-960; Kragh-Hansen, et al., (2006) *J. Mol. Biol.* 363:702-712); Hamilton, *Biochim. Biophys. Acta* (2013) 1830:5418-5426; Fujiwara et al., (2013) *Biochim. Biophys. Acta* 1830:5427-5434), bilirubin and hemin (Zunszain et al., (2008) *J. Mol. Biol.* 381:394-406; Wardell et al., (2002) *Biochem. Biophys. Res. Commun.* 291:813-819; Zunszain et al., (2003) *BMC Struct. Biol.* 3,6; Tsuchida et al., (2009) *Bioconjug. Chem.* 20:1419-1440), thyroid hormones (Petitpas et al., (2003) *Proc. Natl. Acad. Sci. USA* 100:6440-6445), retinol and retinoic acid (N'soukpoé-Kossi et al., (2007) *Int. J. Biol. Macromol.* 40:484-490), uremic toxins (Sakai et al., (1995) *Biol. Pharm. Bull.* 18:1755-1761; Ghuman et al., (2005) *J. Mol. Biol.* 353:38-52), Cys$^{34}$ (Kragh-Hansen, et al., (2002) *J. Biol. Pharm. Bull.* 24:695-704), homocysteine thiolactone (formed from methionyl-tRNA, and S-nitrosohomocysteine, formed in endothelial cells (Glowacki, et al., (2004) *J. Biol. Chem.* 279:10864-10871), nitric oxide (NO) (Ishima et al., (2013) *BioMed Res. Int. Article ID* 353892), Cu$^{2+}$ and Ni$^{2+}$ (Rózga et al., (2007) *J. Biol. Inorg. Chem.* 12:913-918), transition metal ions (Bal et al., (2013) *Biochim. Biophys. Acta* 1830:5444-5455; Barnett et al., (2013) *Biochim. Biophys. Acta* 1830:5456-5464).

Some examples of exogenous ligands of albumin include, for example, bacteria (Lejon et al., (2004) *J. Biol. Chem.* 279:42924-42928), resveratrol (Xiao et al., (2008) *J. Fluoresc.* 18:671-678; Bourassa et al., (2010) *J. Phys. Chem. B* 114:3348-3354), noble gases (Seto et al., (2008) *Anesth. Analg.* 107:1223-1228).

Further, human serum albumin is able to stereoselectively bind a great number of various endogenous and exogenous compounds (Chuang et al., (2006) *Chirality* 18:159-166). Still further, albumin binds a multitude of drugs (Ghuman et al., (2005) *J. Mol. Biol.* 353:38-52; Wang et al., (2013) *Biochim. Biophys. Acta* 1830:5356-5374; Kragh-Hansen et al., (2002) *Biol. Pharm. Bull* 25:695-704; Otagiri, (2005) *Drug Metab. Pharmacokinet.* 20:309-323; Fanali et al., (2012) *Mol. Aspects Med.* 33:209-290). For instance, the Worldwide Protein Data Bank (www.wwpdb.org) provides the structure of at least 106 different ligand-human serum albumin complexes (Aug. 21, 2014).

A large number of endogenous and exogenous toxins, including drug-overdoses, can be removed from the body by albumin-facilitated extracorporeal dialysis, which also passively can remove water-soluble, non-binding toxins (Mitzner (2011) *Ann. Hepatol.* 10(1):521-28; Taguchi et al., "Albumin dialysis" in Otagiri et al., (eds.) (2013) *Human serum albumin. New insights on its structural dynamics, functional impacts and pharmaceutical applications.* Sojo University Publishing Center, Kumamoto, Japan, pp. 401-415). Albumin may also bind to carbon monoxide, carbon dioxide, hydrogen ion, and hydrogen carbonate. A high-throughput, solution-based method for drug library screening with albumin has been developed (Flarakos et al., (2005) *Anal. Chem.* 77:1345-1353).

Vanholder et al., *J. Am Soc Nephrol* 2008: 19: 863-87 teach that focusing on cardiovascular damage as a model of uremic effects resulting in substantial morbidity and mortality, most molecules with potential to affect the function of a variety of cell types within the vascular system are difficult to remove by dialysis. Examples are the larger middle molecular weight molecules and protein-bound molecules. Recent clinical studies suggest that enhancing the removal of these compounds is beneficial for survival. Examples of such uremic toxins are provided in the Uremic Toxin Database (http://www.uremic-toxins.org/DataBase.html).

Malhotra et al., *Pharmacogenet Genomics* 2014; 24(12): 582-587 teach siRNA gene therapy using albumin as a carrier. RNA interference or post-transcriptional gene silencing is one of the most innovative, highly specific, and efficient technologies for gene therapy in molecular oncology. It is already a well-established research tool for analyses of molecular mechanisms for various diseases including cancer as it efficiently silences the expression of genes of interest. However, for its proper therapeutic use, an efficient tumor-specific in vivo delivery mechanism is essential. Albumin may be used as a delivery module for small interfering RNA as it is an endogenous natural nanoparticle.

An Apparatus or a System Suitable for Dialyzing a Biological Fluid Containing a Protein-Binding Substance to be Removed and a Method of Dialysis Using the Same The present invention provides a process whereby, with a suitable means, the concentration ratio of a toxin-protein complex to free toxin and free protein in a dialysis fluid circuit, in a biological fluid circuit or in both circuits is shifted in favor of the free substance, and the toxin is then removed. Analogously it is also possible to consider the concentration ratio of adsorbed toxin to free toxin and adsorbent. This process provides the advantage that, once in solution, a toxin can be removed easily and efficiently from a biological fluid. This process not only affords a rapid dialysis, coupled with an appreciable cost advantage, but also makes it possible to achieve a particularly thorough purification of a biological fluid. In the case of blood or blood plasma purification, this process further provides a more patient-friendly method of treatment which, in the area of emergency medicine for acutely life-threatening conditions, can be crucial to successful treatment.

The terms "dissolved substance" and "free toxin" are understood as meaning not only individual molecules solvated by a solvent, but also those bound to a dialyzable substance. A toxin bound to a dialyzable substance can also be dialyzable as a complex.

Apparatus or System

The means for changing the concentration ratio of a toxin-protein complex to a free toxin and a free protein may feature a device for adjusting the pH of the usable fluids, a device for adjusting the temperature of the usable fluids, a device for adding substituate to dilute or change the composition (for instance the salt content) of the usable fluids, a device for adding dialyzable compounds binding to the substances to be removed, or a device for irradiating the usable fluids with waves, electrical, electromagnetic or magnetic fields. The different devices can be combined with one another in any desired manner. It is preferable to use at least one device for adjusting the pH and at least one device for adjusting the temperature in a circulation system.

One advantage of the present invention is that, with simple means, i.e. conventional devices for adding solutions of acids, bases, substituate or dialyzable substances, or conventional heating, cooling or ultrasonic apparatuses or other generators of light, infrared, ultraviolet or electromagnetic waves, the substances to be removed can be solubilized in a simple and cost-effective manner by weakening the bond between protein-binding substances and carrier proteins or adsorbers. The dissolved substances (toxins) are dialyzable and hence easy to remove. The binding affinity of carrier proteins like albumin or adsorbers for toxins can be selectively lowered by a number of measures, thereby increasing the concentration of the free toxins in the solution. The protein-bound substances in the biological fluid or dialysis fluid are actually in equilibrium with a small amount of non-bound substances. Lowering the binding affinity makes it possible to increase the concentration of the non-bound, dialyzable substances, the free substances passing into solution.

If the dialysis fluid circuit contains at least one means for changing the concentration ratio of toxin-protein complex to free toxin and free protein, the dialysis fluid should contain an adsorber for the substances to be removed from the biological fluid. A small proportion of the protein-binding toxins in the biological fluid is in the free form in solution, and this proportion can diffuse through the semipermeable membrane in the dialyzer and bind to the free binding sites of the adsorber in the dialysis fluid. Then, via a means for changing the concentration ratio of toxin-protein complex to free toxin and free protein, for example, a device for adding an acid, the binding affinity between adsorber and toxin is at least temporarily lowered allowing the substances to be removed to pass into solution. The substances to be removed can be removed from the dialysis circuit via dialysis (diffusion) or filtration (convection) or a combination of both processes, hereinafter referred to as diafiltration. Also, the adsorber and free toxin may be separated by centrifugation, as used e.g. in plasma separation for carrying out plasmapheresis.

At least one means for changing the concentration ratio of the toxin-protein complex to the free toxin and free protein may also be provided in the biological fluid circuit containing substances to be removed, bound to a earner protein. In some instances, both the biological fluid circuit and the dialysis fluid circuit contain at least one means for changing the concentration ratio of toxin-protein complex to free toxin and free protein. Substances with different binding behaviors may be removed by the various means available, especially if different measures are combined.

Adjusting the pH of the fluids to the acidic and/or basic range makes it possible to selectively influence the binding of different substances to the respective carrier proteins or adsorbers. Thus, adding an acid makes it possible to lower the pH of the fluid, thereby reducing the binding of certain toxins to proteins in the acidic range and hence increasing the concentration of free toxins in the fluid. For example, the binding of copper ions to albumin can be weakened in this way so that free, dissolved copper ions in the following filter can be removed by dialysis, filtration, diafiltration, centrifugation, a field, or sorting by weight difference. Analogously, the pH of the fluid can be adjusted to the basic range so that the toxins liberated in the alkaline range can then be eliminated from the fluid by dialysis, filtration or diafiltration. Therefore, by adding a base, it is possible to weaken the binding of certain toxins to proteins and hence increase the concentration of free toxin in the fluid. A pH range of 8-13 is often preferred.

After removal of the toxins from the fluid by means of dialysis, filtration, diafiltration or centrifugation, the pH is optionally adjusted to a different advantageous value. This may be desirable particularly when working with an adsorber, e.g. albumin. A different advantageous pH may then be chosen so that the affinity of the adsorber for the toxin is increased again. This allows recycling of the adsorber.

A circulation system (for dialysis fluid or biological fluid to be purified) contains preferably two and more preferably three devices for adjusting the pH, so that the pH can be adjusted to the acidic or basic range with the first device, to the basic or acidic range, respectively, with the second device and back to the original range (usually neutral) with the third device. The circulation system (for dialysis fluid or biological fluid to be purified) may contain two devices for adjusting the temperature so that the usable fluid can for example be heated and then brought back to the previous temperature, or to another desired temperature, by cooling. In some instances, the circulation system contains three devices for adjusting the pH and two devices for adjusting the temperature.

By means of dialysis, filtration or diafiltration devices provided in the dialysis fluid circuit and/or the biological fluid circuit, the dissolved, dialyzable substances can be removed from the fluids (dialysis fluid or biological fluid to be purified) easily and efficiently after separation from the carrier proteins or adsorbers. This can be accomplished using conventional dialysis apparatuses such as the ones known to those skilled in the art. In addition, it is preferable to use devices for changing the pH/temperature values and devices for appropriate monitoring of these changes. Advantageously, a dialysis, filtration, diafiltration or centrifugation device is inserted downstream from a device for adjusting the pH or temperature of the fluid to be used, in order to remove the free, dissolved substances directly from the fluid. In some instances, a device for adding acid or base, a dialysis, diafiltration, filtration or centrifugation device, a device for adding base or acid, a dialysis, filtration, diafiltration or centrifugation device and a device for adding acid or base are provided, in that order, in the dialysis fluid circuit and/or biological fluid circuit. This makes it possible to remove different protein-binding substances from the dialysis fluid and biological fluid very efficiently and the purified dialysis fluid can in turn be recycled to the dialyzer to recharge the adsorber with protein-binding substances.

An advantage of one embodiment, where a means for changing the concentration ratio of toxin-protein complex to free toxin and free protein, for example a device for adjusting the pH, is arranged only in the biological fluid circuit, is that, to remove unwanted protein-bound toxins, the dialysis fluid does not necessarily have to contain an adsorber, for example the acceptor protein albumin, which drastically reduces the dialysis costs.

Devices for adjusting the pH include especially devices for adding acid or base, for example metering pumps. Appropriate acids or bases arc aqueous solutions of biologically compatible acids or bases. It is generally preferable to use acids or bases whose conjugate bases or acids are ions that occur naturally in the human organism. Examples of acids which can be used are hydrochloric acid, sulfuric acid or acetic acid, hydrochloric acid being preferred. Examples of bases which can be used are sodium hydroxide solution or potassium hydroxide solution, sodium hydroxide solution being preferred. The biological or dialysis fluid can be adjusted e.g. to a pH of between 1 and 7, advantageously of between 2.5 and 5, by adding acid, and to a pH of between 7 and 13, advantageously of between 8 and 13, by adding base. In each particular case the desired pH depends substantially on the nature of the fluid used, the nature of the protein and the properties of the substances to be removed. For example, the binding affinity of copper for albumin is significantly lowered in the pH range around 2. Conversely, this means that copper has a particularly high binding affinity for albumin at a pH above about 3. It has also been observed, for example, that the binding affinity of bilirubin for albumin is significantly lowered at a pH of about 12.

Devices for adjusting the temperature include especially heating devices such as conventional heating apparatuses, microwave apparatuses or infrared apparatuses, or cooling devices such as conventional cooling units. One or more heating/cooling devices can be arranged in the dialysis fluid circuit and/or biological fluid circuit. In particular, the substances to be removed can be solubilized by heating or cooling the usable fluids, while the biological fluid or dialysis fluid can be brought back to the desired temperature by cooling or heating. The nature and extent of the temperature gradient used depends on the nature of the fluid, the adsorber and the toxin to be removed. For example, it is possible to heat first and then cool again. The reverse process may also be advantageous. It may also be advantageous to carry out the heating/cooling step-wise.

Another advantage of the invention is that the binding affinity of the adsorber can be selectively increased by a device for cooling or heating the usable dialysis fluid, whereby free, dissolved substances that have diffused into the dialysis fluid can be bound by recycled adsorbers.

The desired temperature of the fluids to be used is substantially dependent on their nature. If the biological fluid used is blood or partial blood products like blood plasma or fractions thereof, it is possible to heat to a temperature of up to approximately 150° C. (coupled with a corresponding pressure increase, e.g. as used in the heat sterilization of milk), preferably of up to 45° C. Thus heating beyond the physiological range is also possible. When using the means of dialysis according to the invention in an extracorporeal circuit on a patient, the temperature can be lowered again to an optimum value for the patient in the range from 35 to 37° C., or approximately 35° C. in the case of patients with hepatic encephalopathy. If the device for adjusting the temperature is used in the dialysis fluid circuit, the temperature can also be increased to over 150° C. by providing steam, or a pressure increase, or other stabilizers (known from the pasteurization treatment of albumin).

The heating of the fluid to be used in the circulation system can be performed via direct heating of the fluid-filled tubing system by means of a heating apparatus or by means of irradiation with microwaves or infrared. It may be sufficient to have heating devices only in the dialysis fluid circuit, the biological fluid nevertheless being heated as well because of the heat exchange between the fluid to be purified and the dialysis fluid in the dialyzer. In some instances, upstream from the entrance to the dialysis fluid circuit or biological fluid circuit, a heating device can also be inserted downstream from a device for adjusting the pH or a device for adding substituate. In this case the dialysis fluid and/or the fluid to be purified are heated by adding warm solutions.

An ultrasonic apparatus can be used as the device for irradiating with waves. Other appropriate devices are those suitable for generating light waves, ultraviolet waves, infrared waves, radio waves, microwaves and constant or changing electrical or magnetic fields.

Another possible means for changing the concentration ratio of toxin-protein complex to free toxin and free protein is a device for adding dialyzable compounds binding to the substances to be removed. The means can be conventional metering pumps which introduce aqueous solutions of the dialyzable compounds. The dialyzable substances, some of which are bound to toxins, can easily be removed via the conventional dialysis or diafiltration devices. Binding compounds which can be used are dialyzable compounds of low/intermediate molecular weight that are distinguished by a strong affinity for the substances to be removed. These compounds include caffeine, which binds to bilirubin, and common chelating agents like penicillamine, trientine, deferoxamine, preferiprone, HBED, vitamin C, BAL, DMPS or DMSA, which bind to metal cations such as copper ions or iron ions. The dialyzable compounds can be added both to the biological fluid and to the dialysis fluid, but preferably to the dialysis fluid in order to avoid complications due to possible contamination of the biological fluid in the event of incomplete removal by dialysis. Synergistic effects can also occur when using two means for changing the concentration ratio of toxin-protein complex to free toxin and free protein, for example an increase in pH and the addition of a binding compound (e.g. caffeine).

Devices for adding substituate to dilute or change the salt content of the usable fluids include conventional metering pumps with which a substituate solution can be added. Such a device is preferably used in combination with a heating device, inserted downstream therefrom, so that warm substituate is added to the circuit of the fluids used. Suitable substituate solutions are aqueous solutions which can contain various salts as well as urea. These solutions can be commercial dialysis fluids which, as required, can be adjusted to the desired concentration by adding salts. However, it is also possible to use stabilizers, agents for thinning the blood, such as heparin or citrate, or substances for changing the osmotic equilibrium, such as salts, or for changing the electrophysiological equilibrium (Donnan effect), such as negatively or positively charged substances. The substituate serves not only to solubilize the substances to be removed by changing the salt concentration in the fluid. The salt concentration of the biological fluid, e.g. blood, can also be precisely adjusted according to the patient's condition by adding substituate. Moreover, it can also be used to restore the binding capacity of recycled adsorber for toxins in the dialysis circuit. Also, the addition of urea may be necessary to improve the binding capacity of the adsorber.

The dialyzers used can be conventional dialyzers currently used e.g. for haemodialysis. It is also possible to use membranes with larger pores than those presently used for dialysis. The dialyzer is equipped with a conventional semipermeable dialysis membrane; the diffusion through the membrane can optionally be supported by convective transport by means of filtration. The dialyzer essentially comprises two chambers separated by a dialysis membrane, to each of which is connected a circulation system (tubing system) for the fluids to be used. The biological fluid to be purified and the dialysis fluid are conventionally conveyed in counter-current, but they can also be conveyed in cocurrent. Conventional components of a dialyzer, such as manometers, air detectors, pumping devices like heparin pumps, blood pumps, etc., form part of the means. The means according to the invention can achieve both slow dialysate flows (1-2 l/h) and normal dialysate flows (25-150 l/h) as well as intermediate rates, as required.

The biological fluids which can be used in the means according to the invention or in the process according to the invention include all human or animal body fluids, especially blood or blood plasma, particularly preferably of human origin. The removal of protein-bound substances from the biological fluids used is simultaneously accompanied by the elimination of water-soluble substances, for example urea or various ions that can normally be removed in conventional dialysis. The protein-binding substances to be removed are preferably bound to the carrier protein albumin. The means according to the invention is particularly suitable for purifying blood and plasma in the medical sector and can be used both in the field of blood bank processing and for extracorporeal dialysis on patients.

The dialysis fluids used can be conventional dialysis fluids such as the ones known to those skilled in the art. The ion concentration can be adapted to the individual patient's needs. Customary ion-containing aqueous solutions or pure water can be used, as required. The conventional dialysis fluids are optionally provided with an adsorber for the protein-binding substances to be removed. Examples of possible adsorbers are resinate and acceptor proteins as well as albumin, which can be human serum albumin, animal albumin or genetically engineered albumin. Human serum albumin is especially suitable. The serum albumin solutions can optionally be diluted with water, conventional dialysis fluids or other fluids. The dialysis fluid used can contain human serum albumin in a concentration of 0.1 to 25 g per 100 ml, preferably of 1 to 10 g per 100 ml and particularly preferably of 1 to 3 g per 100 ml.

Other dialysis fluids which can be used are blood, blood serum or fresh frozen plasma. The dialysis fluid can also be a dialysate from the bioreactor. Enormous quantities of blood are currently needed for bioreactors (systems working with living liver cells for hepatic replacement therapy). Thus, up to one liter of blood has to be withdrawn from the patient's circulation during the circulation of the bioreactor. To stimulate the synthetic function of the liver cells in the bioreactor, however, it may also be sufficient to employ a system which uses a dialysate containing toxic substances that are normally removed in the liver. Accordingly, a dialysate as described can first be passed through the bioreactor in the extracorporeal circuit. This dialysate is then purified and the dialysate returned to the patient. To do this it may be necessary to add albumin continuously to the dialysate or to use a capillary or a membrane that is more permeable to albumin than dialysis filters used at the present time. The means described herein can be equipped with one or more conventional pH meters and/or thermometers for monitoring the corresponding properties of the fluids used.

Method of Dialysis

The apparatus or system may be used in a process for removing unwanted substances from a biological fluid. The biological fluid is dialysed against a dialysis fluid through a semipermeable membrane. The dialysis fluid contains an adsorber for protein-binding substances to be removed, and the dialysis fluid is adjusted by adding acid, base or dialyzable substances, by dilution, by changing the salt content, by irradiation with waves or by heating, in such a way that the binding affinity of the adsorber for the bound substances is at least temporarily lowered, thereby increasing the concentration of the free unwanted substances in the dialysis fluid. Also, the biological fluid may be adjusted, by adding acid, base or dialyzable substances, by dilution, by changing the salt content, by irradiation with waves or by heating, in such a way that the binding affinity of the carrier protein for the bound substances to be removed is lowered, thereby increasing the concentration of the free unwanted substances in the biological fluid. The process may use a circulation system featuring an at least two-fold addition of acid, base or dialyzable substances, dilution, changing of the salt content, irradiation with waves or heating/cooling of the dialysis fluid or biological fluid.

The processes according to the invention can be used in general for purifying biological fluids. Biological fluids include all human or animal body fluids, especially blood or blood plasma, particularly preferably of human origin. It is possible here to return the withdrawn fluids, especially blood or blood plasma, to the body or make them available for other purposes. Thus, for example, blood bottles can be purified or the purified biological fluids are made available for other commercial purposes or research purposes.

Figure 2:
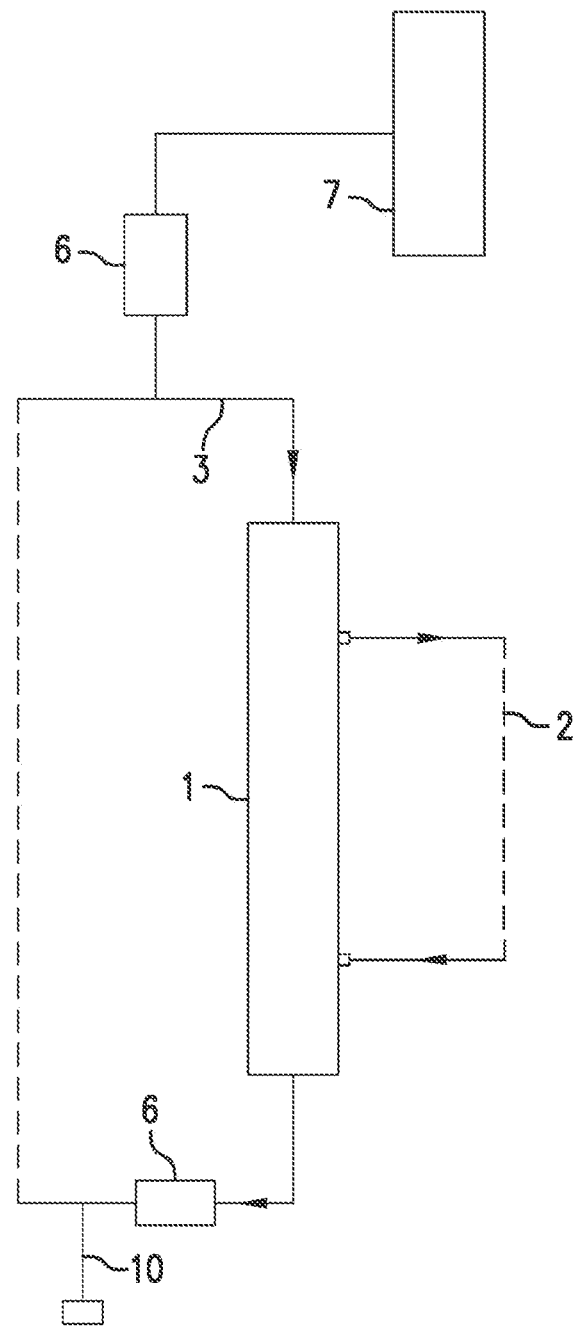
FIG. 2 is a simplified diagrammatic representation of a dialysis apparatus or system with heating and cooling devices and a device for adding substituate in the apparatus or system.
Figure 3:
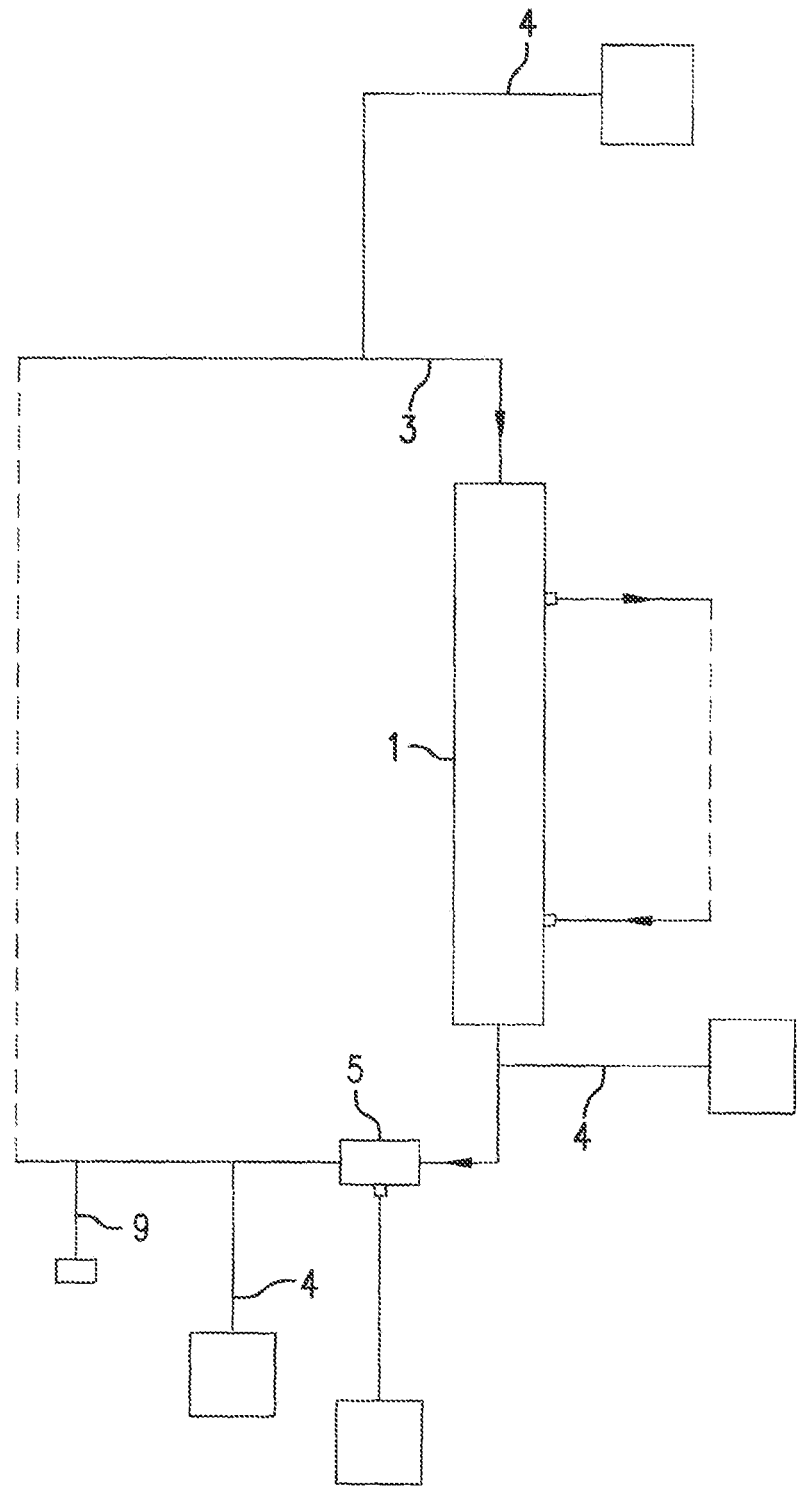
FIG. 3 is a simplified diagrammatic representation of a dialysis apparatus or system with devices for adjusting the pH in the apparatus or system.
Figure 4:
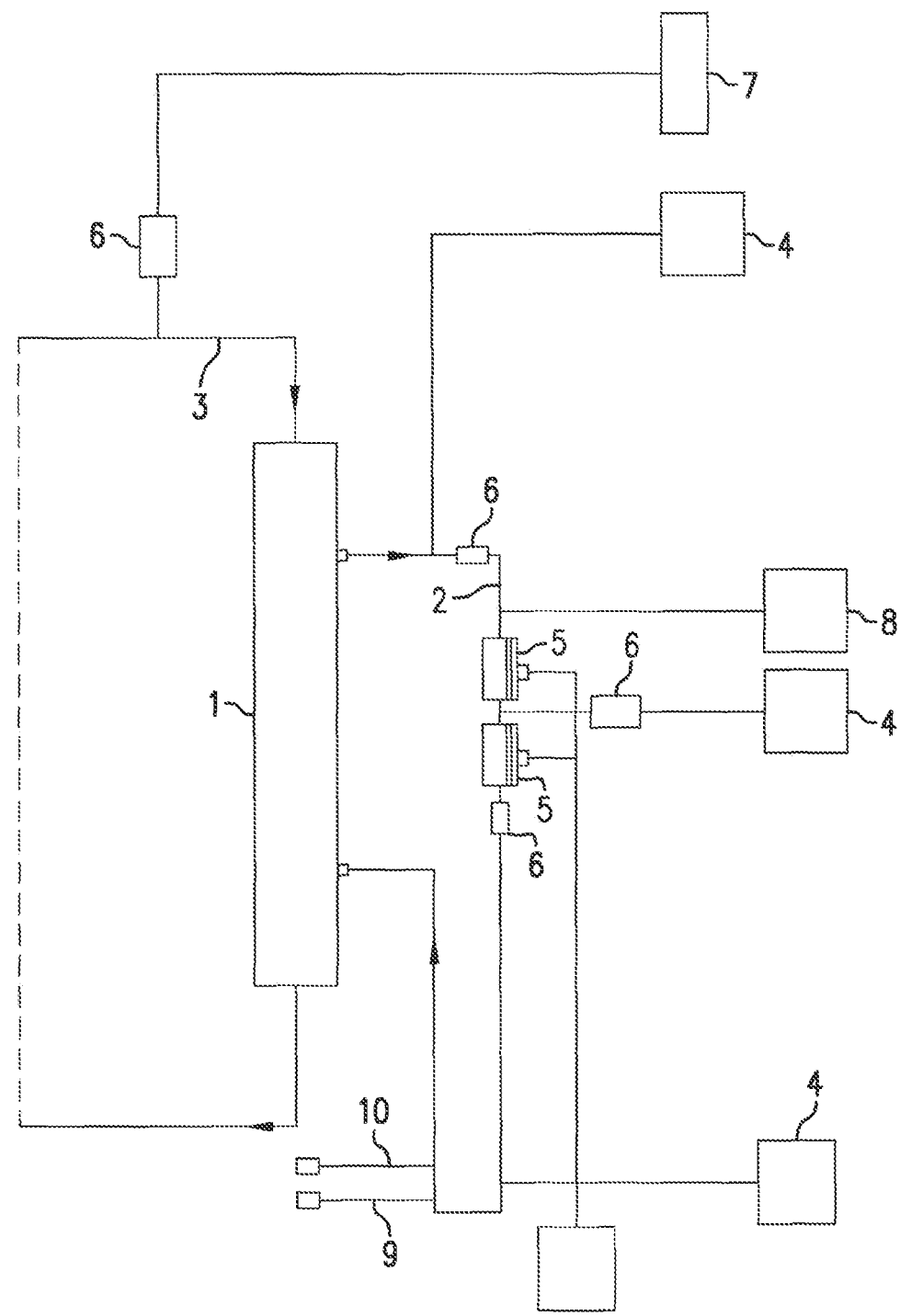
FIG. 4 is a simplified diagrammatic representation of a dialysis apparatus or system with heating and cooling devices, devices for adjusting the pH and a device for adding substituate in the dialysis fluid circuit.

FIG. 2 is a simplified diagrammatic representation of dialysis apparatus or system with heating and cooling devices and a device for adding substituate in the extracorporeal circuit. FIG. 3 is a simplified diagrammatic representation of dialysis apparatus or system with devices for adjusting the pH in the extracorporeal circuit. FIG. 4 is a simplified diagrammatic representation of dialysis apparatus or system with heating and cooling devices, devices for adjusting the pH and a device for adding substituate in the dialysis fluid circuit.

FIG. 2 shows a means of hemodialysis consisting essentially of a dialyzer 1, a dialysis fluid circuit 2 (only suggested in the Figure: used dialysate does not have to be recycled in this embodiment), a biological fluid circuit 3 (only suggested in the Figure), heating and cooling apparatuses 6, a device 7 for adding substituate and a thermometer 10. Via the device 7, substituate, e.g. from a conventional hemofiltration solution, heated in the heating apparatus 6, is added to the biological fluid such as blood in the biological fluid circuit 3 before it enters the dialyzer 1. The warm biological fluid then enters the biological fluid chamber of the dialyzer 1. Because the temperature of the biological fluid such as blood has been raised, there is an increased liberation of protein-bound substances from the carrier proteins, thus producing an increased pool of dissolved, dialyzable toxins which diffuse through the dialysis membrane into the dialysis chamber of the dialyzer 1. When the biological fluid such as blood, purified of protein-bound substances, has left the dialyzer 1, it is cooled again by the cooling unit 6 to a physiologically acceptable temperature, which is checked by the thermometer 10. Alternatively, the biological fluid such as blood temperature and hence the patient's temperature can also be adjusted by controlling the dialysate temperature. The biological fluid such as blood is then returned to the biological fluid circuit 3. Similarly, the biological fluid such as blood may be first cooled down 6, pass through the dialyzer 1 and then be heated up 6.

FIG. 3 shows a means of hemodialysis consisting essentially of a dialyzer 1, a dialysis fluid circuit 2 (only suggested in the Figure: used dialysate does not have to be recycled in this embodiment), a biological fluid circuit 3 (only suggested in the Figure), metering pumps 4 for adding acid or base, a dialyzer 5 and a pH meter 11. By means of the metering pump 4, an acid such as an HCl solution is added to the biological fluid in the biological fluid circuit 3 before it enters the dialyzer 1. This lowers the pH of the biological fluid and some of the toxins pass into solution. The acidified biological fluid then enters the biological fluid chamber of the dialyzer 1. The dissolved, dialyzable substances can diffuse through the dialysis membrane into the dialysis chamber of the dialyzer 1. When the biological fluid, partially freed of protein-bound substances, has left the dialyzer 1, an alkaline solution such as a NaOH solution is added by means of the metering pump 4, whereby the pH is adjusted to the basic range and further protein-binding toxins pass into solution. Downstream the blood enters another dialyzer 5, where another dialysis, filtration or diafiltration is carried out in order to eliminate otherwise protein-bound substances dissolved in the alkaline range. The pH is then adjusted to approximately 7.4 in the neutral range with HCl solution via a metering pump 4, this being checked by the pH meter. The biological fluid is then returned to the biological fluid circuit 3.

FIG. 4 shows a means of hemodialysis consisting essentially of a dialyzer 1, a dialysis fluid circuit 2, a biological fluid circuit 3 (only suggested in the Figure), metering pumps 4 for adding acid or base, dialyzers 5, heating and cooling apparatuses 6, a device 7 for adding substituate, a device 8 for adding caffeine, a pH meter and a thermometer 10.

Via the device 7, substituate, for example, from the hemofiltration solution, heated in the heating apparatus 6, is added to the biological fluid in the biological fluid circuit 3 before it enters the dialyzer 1. The warm biological fluid then enters the biological fluid chamber of the dialyzer 1. Because the temperature of the biological fluid has been raised, there is an increased pool of free, dialyzable toxins which diffuse through the dialysis membrane into the dialysis chamber of the dialyzer 1. The dialysis fluid also contains albumin, which binds to the toxins, so the pool of free substances in the dialysis fluid is kept low, thereby enhancing the diffusion of the toxins into the dialysis fluid. When the biological fluid, purified of protein-bound substances, has left the dialyzer 1, it is returned to the biological fluid circuit 3.

The dialysis fluid from the dialyzer 1, containing albumin-bound toxins, enters the dialysis fluid circuit 2. HCl solution is added to the dialysis fluid via the metering pump 4. This lowers the pH of the dialysis fluid and the pool of dissolved, free toxins in the fluid increases. Arranged downstream in the dialysis fluid circuit 2 is a heating apparatus 6 which heats the dialysis fluid to 41-45° C. whereby the pool of free toxins is increased further and the proportion of protein-bound toxins falls. The next component in the circulation system 2 is a caffeine metering pump 8. The addition of caffeine binds bilirubin in particular, thereby reducing the proportion of protein-bound bilirubin in the dialysis fluid. Downstream the dialysis fluid enters a dialyzer 5, where some of the dialysis fluid is withdrawn from the system in order to keep the concentration of the adsorber in the desired range. In addition, the dialysate is purified by dialysis, filtration or diafiltration, especially to remove free, protein-binding substances and caffeine-bound bilirubin. The albumin cannot pass through the filter due to its high molecular weight. Arranged downstream from the exit from the dialyzer 5 in the dialysis fluid circuit 2 is a metering pump 4 for adding NaOH solution, a heating apparatus 6 being arranged upstream from the entrance to the circuit. Downstream there follows another dialyzer 5 that withdraws the added fluid from the system and eliminates substances dissolved in the alkaline range by dialysis, filtration or diafiltration. The next component in the circulation system 2 is a cooling device 6 by means of which the temperature of the dialysis fluid can be adapted according to the desired temperature of the patient. The following metering pump 4 is used to add HCl solution to the dialysis fluid in order to adjust its pH to the neutral range, so the binding capacity of albumin is increased again and the pH of the blood does not have an adverse influence in the dialyzer. The next components in the circulation system 2 are a pH meter and a thermometer 10 for checking the pH and temperature of the purified dialysis fluid before it reenters the dialyzer 1.

Dialysate Regeneration Circuit

Figure 5:
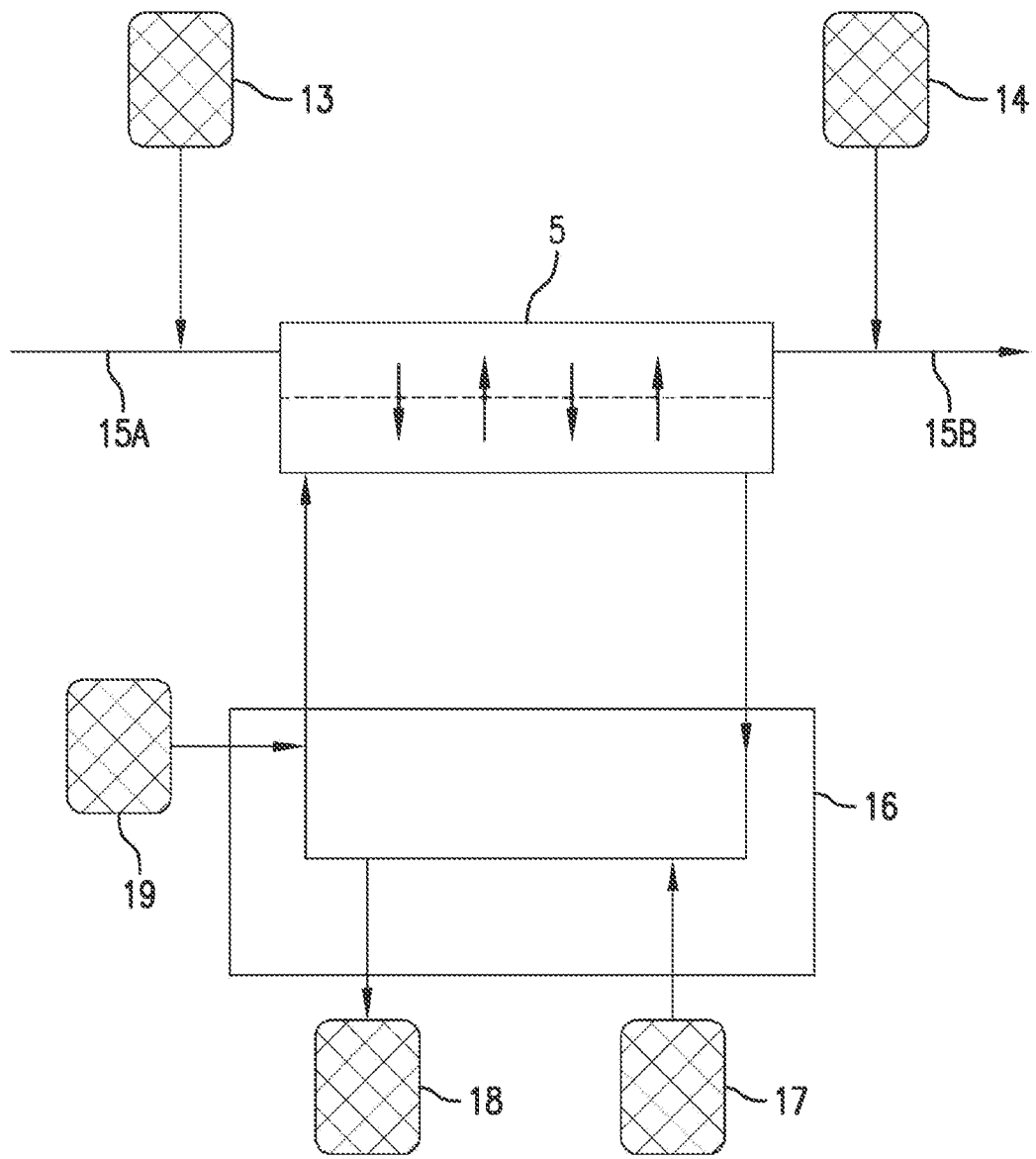
FIG. 5 provides a schematic block diagram of a dialysis system.

FIG. 5 shows a schematic block diagram of a dialysis apparatus or system. Via an arterial blood line 15A, blood from a patient is supplied to a dialyzer 5. Before the blood is supplied to the dialyzer 5, a predilution fluid 13 is added to the blood. In the dialyzer 5, the respective flows of blood and dialysate may be conducted in concurrent flow. Alternatively, the respective flows of blood and dialysate may be conducted in counterflow. At the dialyzer 5, diffusion, convection and/or ultrafiltration processes take place, and the patient's blood is cleaned. After the blood has passed the dialyzer 5, a postdilution fluid 14 is added to the cleaned blood. The cleaned blood is resupplied to the patient via a venous blood line 15B.

The dialysis system features a dialysate regeneration circuit 16 adapted for regenerating dialysate that has passed through the dialyzer 5. A dialysate that contains carrier substances like e.g. albumin is used. In particular, the dialysate regeneration circuit 16 is adapted for removing protein-binding toxins like, for instance, bilirubin, bile acid, etc. from the dialysate. First, one or more fluids 17 are added to the dialysate. Then, fluids 18 are removed from the dialysate, for example, by filtration, diafiltration, precipitation or dialysis under certain pH and temperature conditions. Furthermore, one or more substitution fluids 19 may be added to correct the concentration of the electrolytes and other important substances in the dialysate. From the dialysate regeneration circuit 16, a flow of regenerated dialysate is supplied to the dialyzer 5.

Figure 6A:
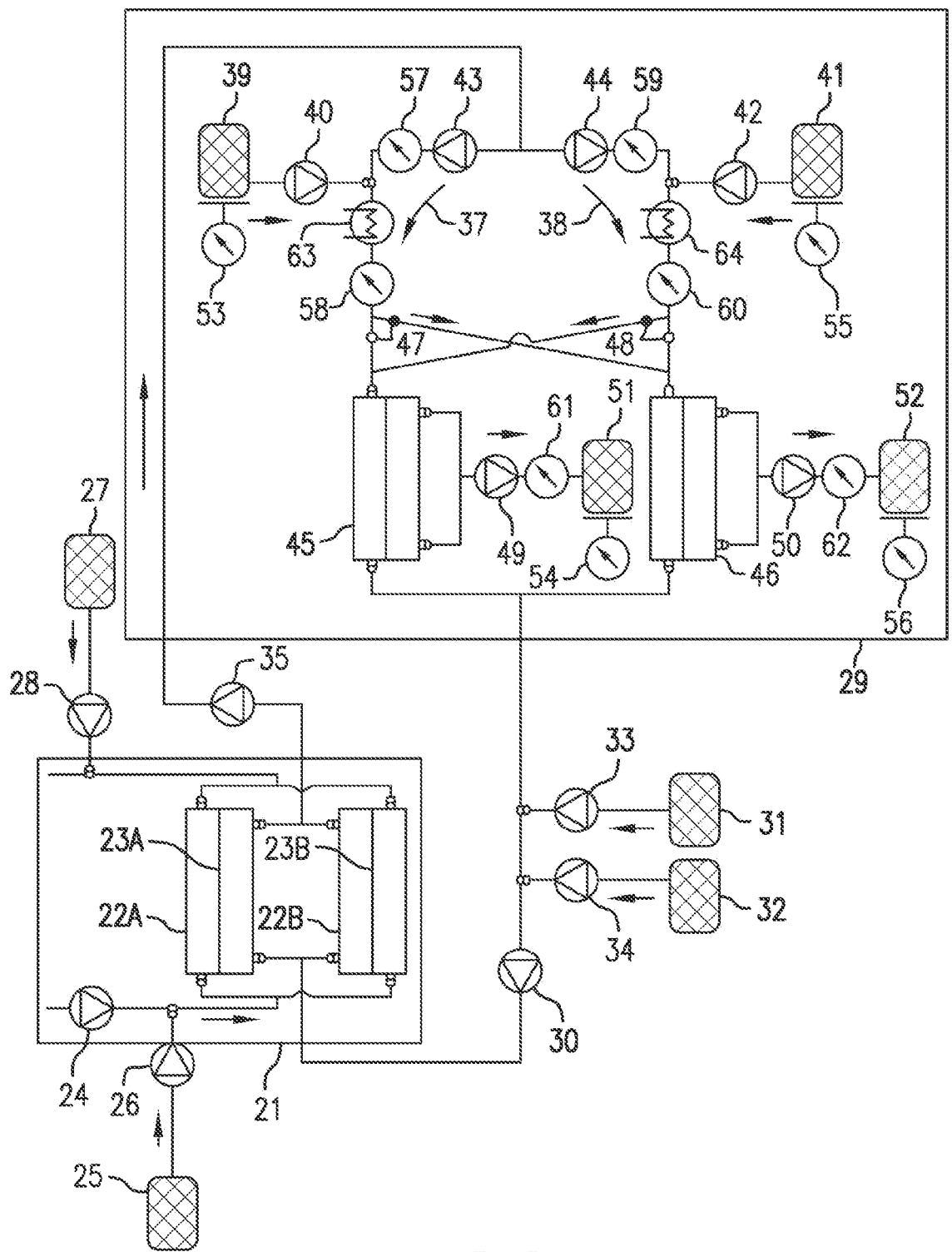
FIG. 6A shows one embodiment.

FIG. 6A provides a more detailed view of a dialysis apparatus or system. The dialysis system features a biological fluid circuit 21 with two dialyzers 22A and 22B. Each of the dialyzers 22A and 22B comprises a biological fluid compartment, a dialysate compartment, and a semipermeable membrane 23A, 23B that separates the compartments. The dialyzers 22A, 22B are fluidically connected in parallel. A biological fluid such as blood from the patient is passed through the tubings via a pump 24. Before the biological fluid is supplied to the dialyzers 22A, 22B, a predilution fluid 25 is added to the biological fluid via a predilution pump 26. Then, the biological fluid is passed through the biological fluid compartments of the dialyzers 22A, 22B. Before the cleaned biological fluid is returned to the patient, a postdilution fluid 27 is added to the biological fluid via a postdilution pump 28. Biological fluid flow rates can be between 50-3000 ml/min but are preferably between 150-1000 ml/min, more preferably between 150-600 ml/min. Predilution flow rates can be between 1-20 liters/hour but are preferably between 4-7 liters/hour. Postdilution flow rates can be between 5-30% of the chosen blood flow rates, but are preferably between 10-20%.

Referring to FIG. 6A, the dialysate circuit comprises a dialysate regeneration unit 29. Dialyzing fluid that has been passed through the dialysate regeneration unit 29 is pumped into the dialysate compartments of the dialyzers 22A, 22B with a first dialysate pump 30 at a flow rate between 100-4000 ml/min but preferably between 500-1100 ml/min. In order to bring the electrolytes and other important substances to desired concentrations, substitution fluids 31, 32 may be supplied to the dialysate via respective pumps 33, 34. After passing through the dialysate compartments of the dialyzers 22A, 22B, the dialyzing fluid with the added fluids taken from the patient to reduce his volume overload are transported to the dialysate regeneration unit 29 via a second dialysate pump 35.

The dialysate regeneration unit 29 comprises two flow paths 37, 38 that are fluidically connected in parallel. In flow path 37, the "acidic flow path," an acidic solution 39 comprising a strong acid is added to the dialysis fluid via an acid pump 40. In flow path 38, the "alkaline flow path," an alkaline solution 41 comprising a strong base is added to the dialysis fluid via a base pump 42.

The dialysate regeneration unit 29 comprises two regeneration pumps 43, 44 for transporting the dialysate through the two flow paths 37, 38. Preferably, two separate pumps are used for the transport of the dialysis fluid, because the resistance of the fluid can be different in the acidic flow path 37 and in the alkaline flow path 38. For example, a carrier substance like albumin may have a different shape in acidic or alkaline conditions and therefore different flow characteristics for different pH values. Alternatively to a system with pumps, a system with clamps and fluid measurements may be provided to achieve constant flow rates in the two flow paths 37 and 38.

Each of the two flow paths 37, 38 contains a detoxification unit 45, 46 adapted for filtering or dialyzing the dialysate, and for removing toxins from the dialysate. The detoxification units 45, 46 may be implemented as regeneration dialyzers, ultrafiltration units, diafiltration units, etc. The regeneration pump 43 of the acidic flow path 37 and the regeneration pump 44 of the alkaline flow path 38 transfer the dialysate downstream to one of two detoxification units 45, 46 of the dialysate regeneration unit 29. The dialysate is supplied to the detoxification units 45, 46 via a valve mechanism comprising switching valves 47, 48.

In the detoxification unit through which alkaline solution is flowing, alkaline soluble toxins such as bilirubin can be removed by filtration or dialysis. Under alkaline conditions, the concentration of alkaline soluble toxins in solution is increased. Due to this concentration increase of free toxins, removal of the free toxins is facilitated. In the other detoxification unit through which acidic solution is flowing, these alkaline soluble toxins may be precipitated and thereby removed from the dialysis fluid.

With regard to acidic soluble toxins such as magnesium, a similar effect is observed. In an acidic solution, the concentration of acidic soluble toxins in solution is increased, and hence, acidic soluble toxins may be removed at an increased rate. In contrast, in the detoxification unit through which alkaline solution is flowing, the acidic soluble toxins are precipitated, for example as magnesium hydroxide, and thereby removed from the dialysis fluid.

The switching valves 47, 48 are adapted for changing the direction of the acidified dialysis fluid transported by the regeneration pump 43 on the acidic side either towards the detoxification unit 45 or towards the detoxification unit 46 (switching valves 47) and changing the direction of the alkalized dialysis fluid transported by the regeneration pump 44 on the alkaline side either towards the detoxification unit 46 or towards the detoxification unit 45 (switching valves 48). The switching valves 47, 48 change the direction of flow e.g. every 5-60 minutes so that each detoxification unit 45, 46 receives fluid from one of the regeneration pumps 43 and 44 at a time. However, change of direction of flow may occur every 1 to 60 minutes depending on the acid used and the mechanism applied. Switching may be performed automatically or individually by the user. Change of direction every 1 to 10, preferably every 1 to 5 minutes may be preferred for certain applications.

Depending on the filtration type, the precipitated substances can cause an occlusion of the detoxification units 45, 46 by blocking the pores of the detoxification unit 45, 46. To avoid this, the detoxification units 45, 46 may be alternated. The detoxification unit that is in one time period (e.g., for 30 minutes) the acidic detoxification unit is in the following time period (e.g., 30 minutes) used in the alkaline flow path. This means that then precipitated substances are solved and removed with high concentration by filtration or dialysis. This also enables continuous use of the detoxification units over a long time period.

The switching of the detoxification units 45, 46 may be performed manually, or by a valve mechanism that is electronically controlled. The switching may be performed at different locations in the fluid circuit, the most preferable location being directly upstream of the detoxification units 45, 46. However, the temperature regulation unit 63, 64 may be located in the circuit and/or controlled in a way that allows them to be included into the switching mechanism acting on the detoxification units. The change of direction of the acidified dialysis fluid may be established together with the change of direction of the acidified fluid in the detoxification units 45, 46. However, an independent change of direction of the acidified dialysis fluid in the temperature regulation units 63, 64 and the detoxification units 45, 46 may also be realized. By including the temperature regulation units in the switching mechanism, it is insured that the both units do not accumulate precipitated carrier substances, such as albumin, which may be caused by exclusively contacting the temperature regulation units 63, 64 with either alkalized or acidified dialysis fluid, in particular due to temperature effects at this unit.

For removing fluids and toxins from the detoxification units 45, 46, the system provides two filtrate pumps 49, 50 operative to remove discharge fluids 51, 52 from the detoxification units 45, 46. For balancing the volumes of the different fluids, the system may provide a plurality of scales 53-56 adapted for constantly measuring the fluid volume of the added acid 39, of the added base 41 and of the discharge fluids 51, 52.

Downstream of the detoxification units 45, 46, the flow of regenerated acidified dialysate obtained at the outflow of one of the detoxification units is merged with the flow of regenerated alkalized dialysate obtained at the outflow of the other detoxification unit. By merging the acidified flow with the alkalized flow, the acid and the base neutralize each other, and a flow of regenerated dialysate with a pH in the range between 6 and 11 is generated. The regenerated dialysate may be supplied to the dialyzers 22A, 22B. A temperature regulation unit may be located in the dialysis fluid circuit before the dialysate passes to the dialyzers 22A, 22B. This allows the recycled dialysis fluid to be adjusted to the temperature needed for contacting the blood at the membrane of the dialyzers 22A, 22B.

Preferably, in the acidic flow path 37 and in the alkaline flow path 38, acids or bases are added whose conjugate bases or acids are ions that occur naturally in the human organism. Thus, the regenerated dialysate obtained by merging the acidified flow of dialysate and the alkalized flow of dialysate does not contain any non-physiological substances.

Various system parameters such as pH value, temperature, turbidity, speed (sound speed), concentration, density and conductivity of the dialysate are monitored via sensors 57-60 located on the base and the acid side upstream of the detoxification units 45, 46. In the acidic flow path 37, sensors 57 monitor the system parameters before adding the acid and sensors 58 measure the system parameters after adding the acid. Accordingly, in the alkaline flow path 38, sensors 59 monitor the system parameters before adding the base and sensors 60 measure the system parameters after adding the base.

The system may contain further sensor units 61, 62 located in the discharge flow paths of the detoxification units 45, 46 or in the merge flow portion of the system. The sensor units 61, 62 are adapted for monitoring system parameters like e.g. pH value, temperature, turbidity, speed (sound speed), concentration, density and conductivity.

In each of the flow paths 37, 38, further process steps for at least temporarily increasing the concentration of free toxins in the dialysate may be realized in order to enhance the removal of toxins. These process steps may include one or more of heating or cooling the dialysate, irradiating the dialysate with waves, changing the salt content of the dialysate, adding a dialyzable substance binding to the toxins to be removed.

Referring to FIG. 6A, each of the flow paths 37, 38 contains a respective temperature regulation unit 63, 64. For example, heating of the dialysate may be helpful for weakening the bond between the protein-binding toxins and the carrier substances. The heating may be performed via direct heating of the fluid-filled tubing system, or by irradiation with microwaves or infrared. Alternatively, the temperature regulation units may be adapted for cooling the dialysate. By changing the temperature of the dialysis fluid, the concentration of free toxins in solution is increased and accordingly, removal of toxins is enhanced.

Another possible process step for changing the concentration ratio of toxin-carrier-complex to free toxin and free carrier substance is to irradiate the dialysate with waves. For example, an ultrasonic apparatus may be used as the device for irradiating with waves. Other appropriate devices may e.g. be those suitable for generating light waves, ultraviolet waves, infrared waves, radio waves, microwaves, and electrical or magnetic fields. All different waves and fields can be constant or changed periodically with different frequencies.

Another possible process step for changing the concentration ratio of toxin-carrier-complex to free toxin and free carrier substance is to change the salt content of the dialysate. Changing the salt concentration may help solubilize the toxins to be removed. Moreover, changing the salt concentration may also be used to restore the binding capacity of recycled carrier substances for toxins. The addition of urea may be necessary to improve the binding capacity of the carrier substances.

Another possible process step for changing the concentration ratio of toxin-carrier-complex to free toxin and free carrier substance is to add dialyzable compounds to the dialysate. The dialyzable compounds may be adapted to bind to the toxins to be removed. Binding compounds that may be used are dialyzable compounds of low/intermediate molecular weight that are distinguished by a strong affinity for the substances to be removed. Some such compounds include caffeine, which binds to bilirubin, and common chelating agents like penicillamine, trientine, deferoxamine, preferiprone, HBED, vitamins such as vitamin C, BAL, DMPS or DMSA, which bind to metal cations such as copper ions or iron ions.

Figure 6B:
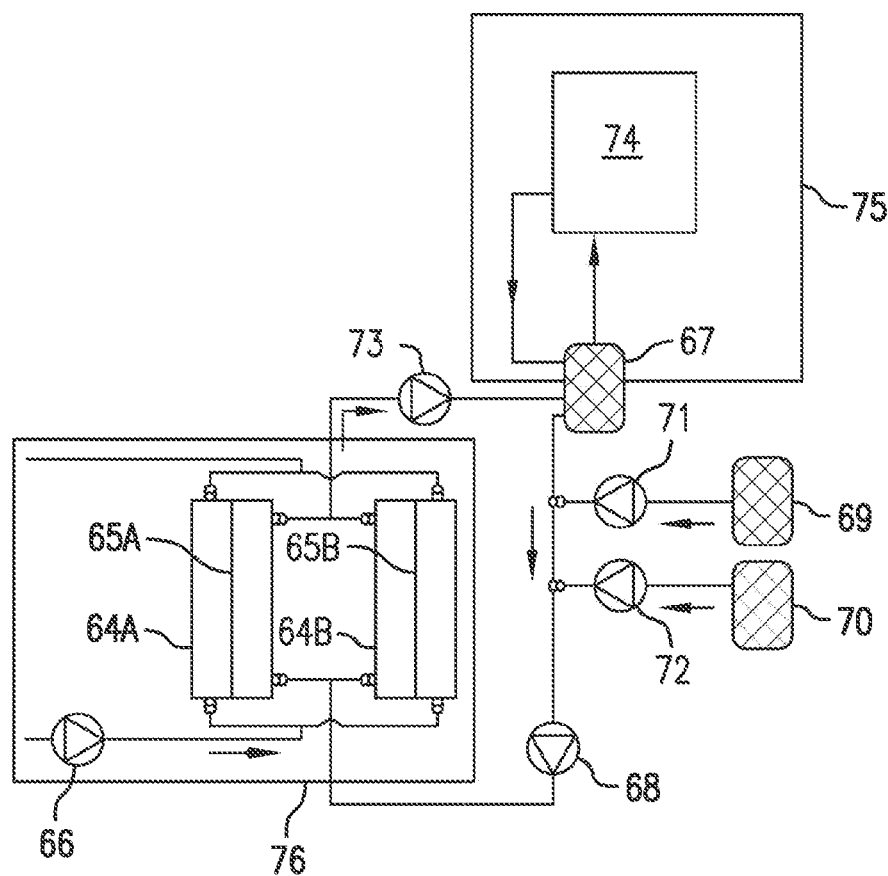
FIG. 6B shows another embodiment where the dialysis apparatus or system features a dialysate reservoir.
Figure 7:
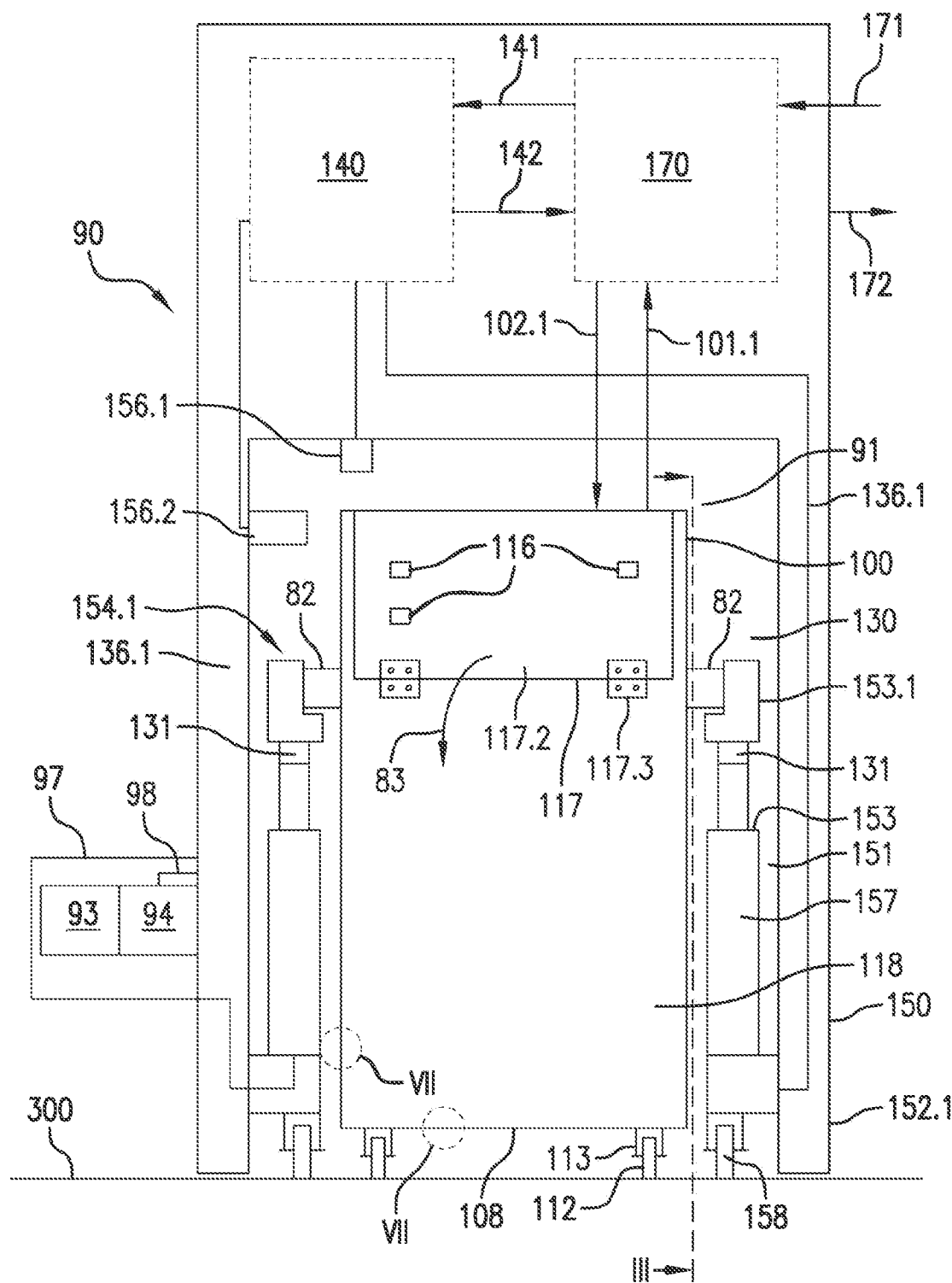
FIG. 7 shows a view of a balancing apparatus or system and a dialysis apparatus or system with a container located within the support housing, in a first position of the container.
Figure 8:
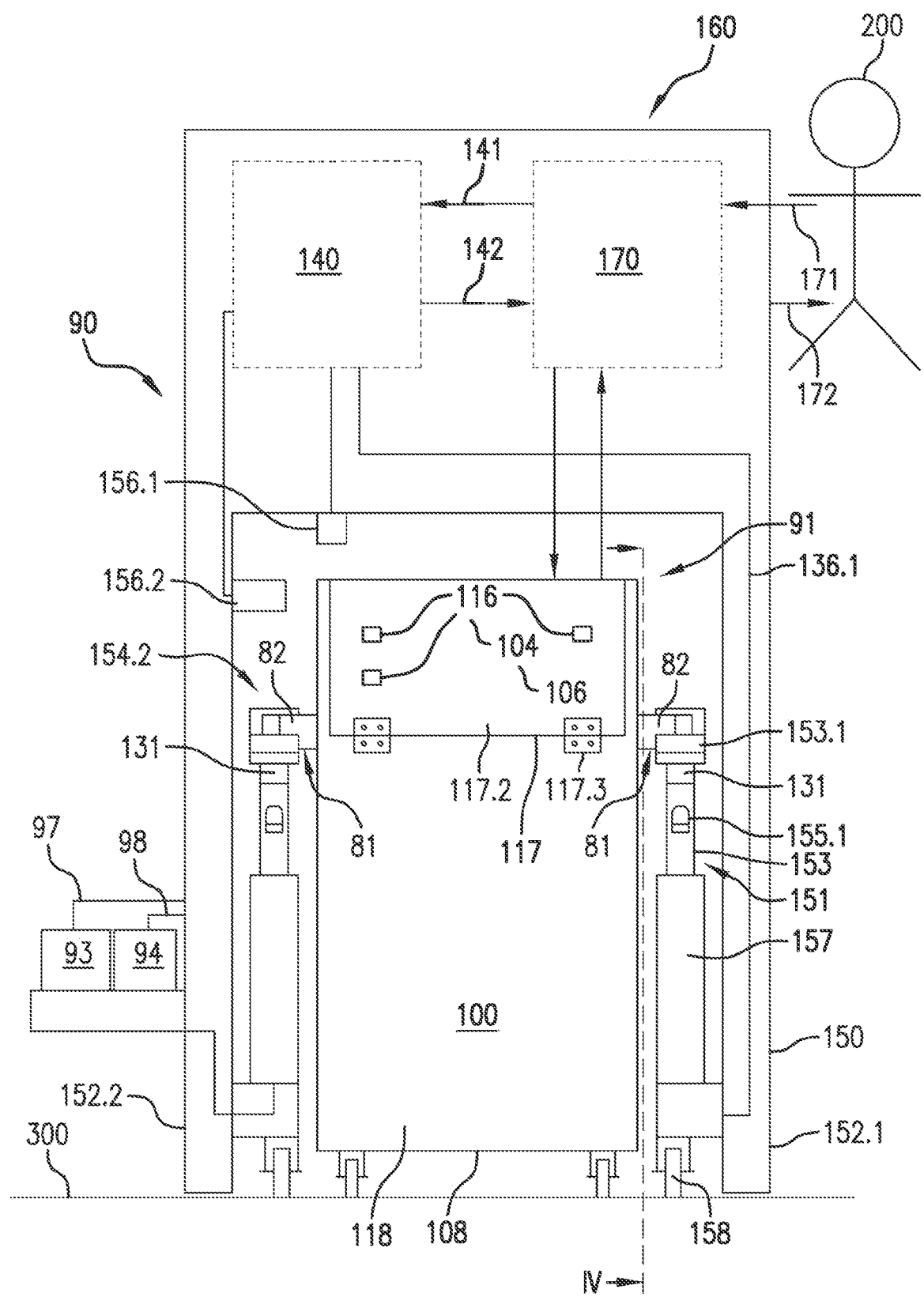
FIG. 8 is a schematic view of the balancing apparatus or system and the dialysis apparatus or system with the container in a second position.
Figure 9:
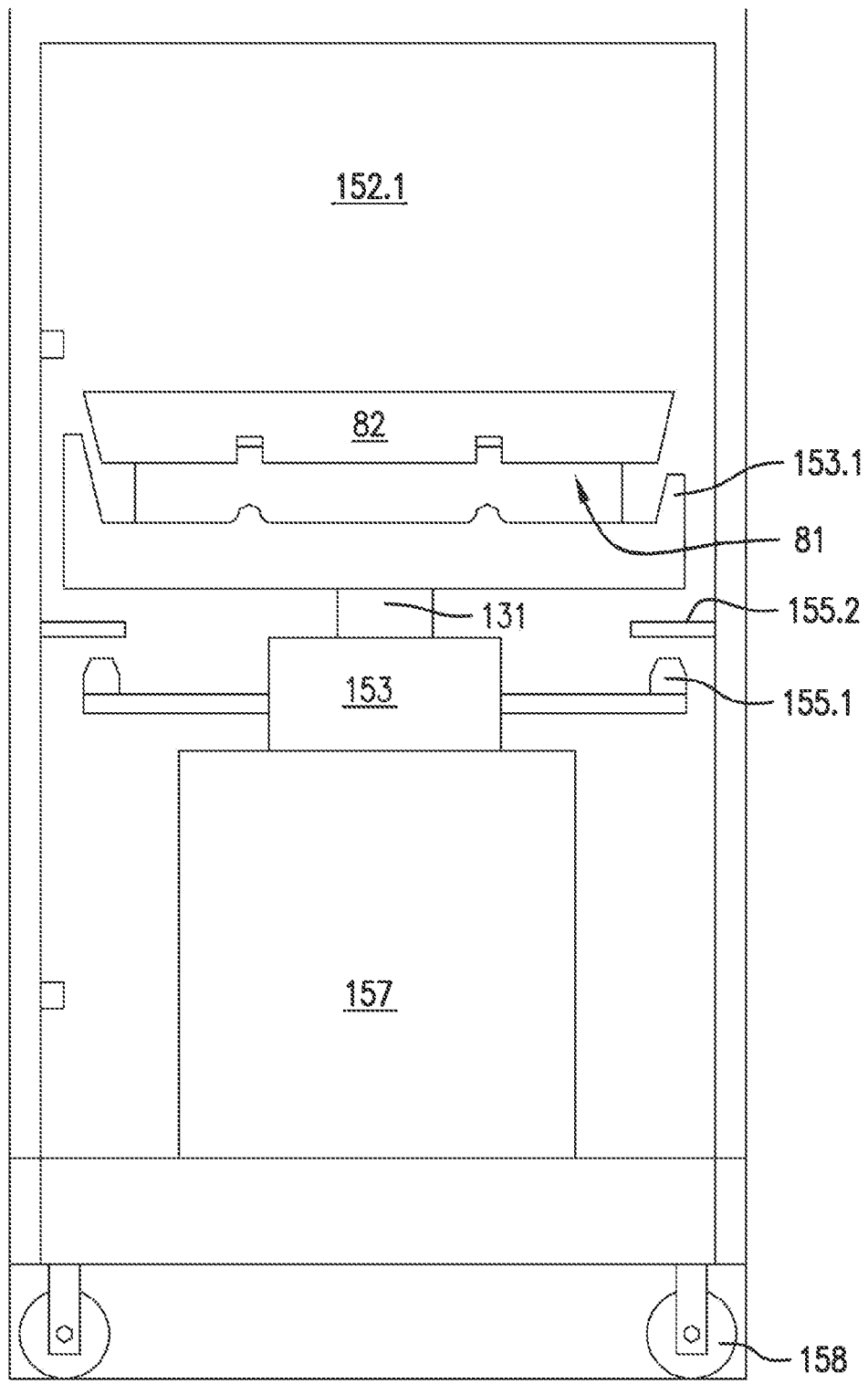
FIG. 9 is a cut view along the line in FIG. 7.
Figure 10:
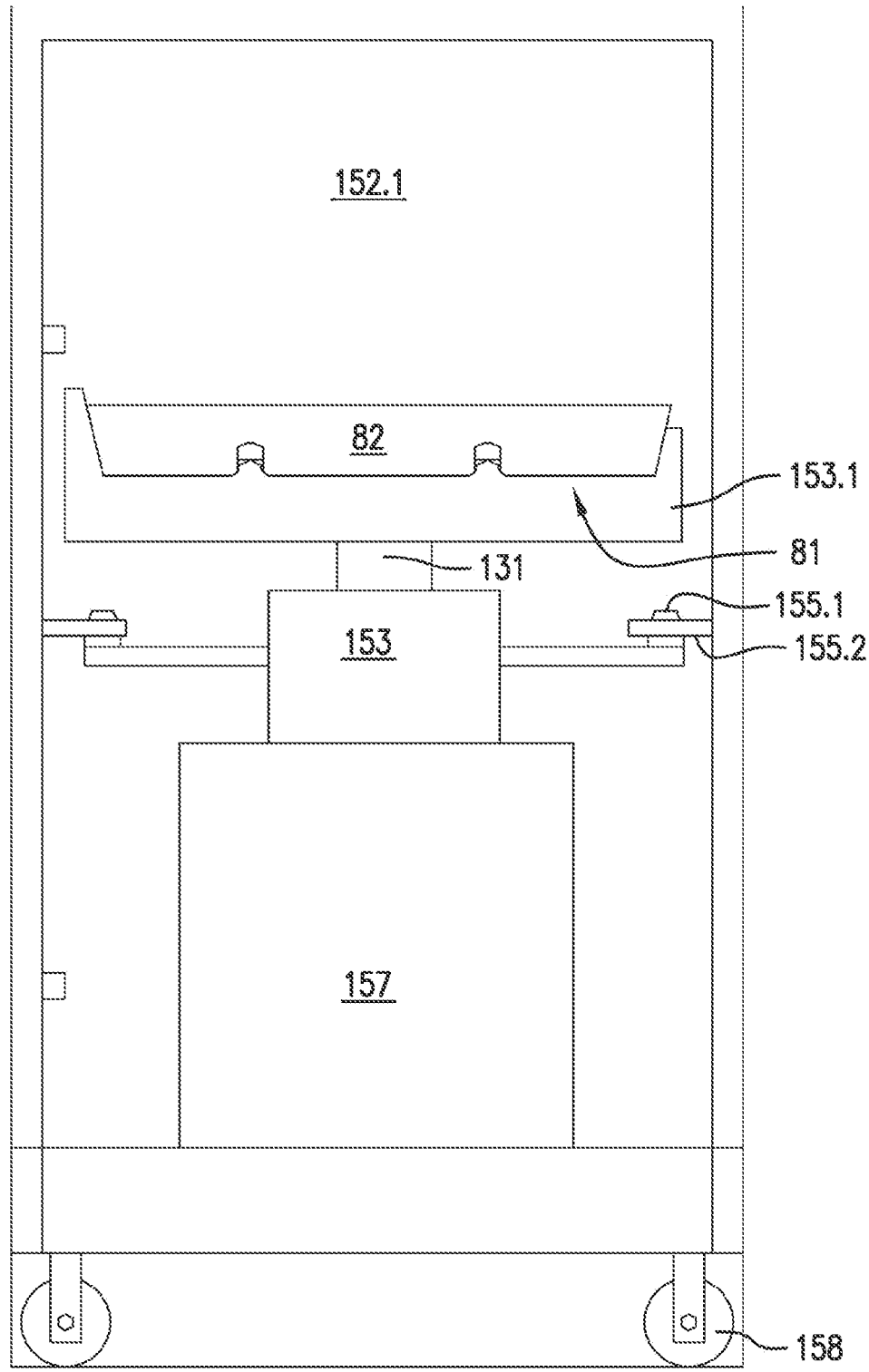
FIG. 10 is a cut view of the balancing apparatus or system and the dialysis apparatus or system according to the line IV-IV of FIG. 8.
Figure 11:
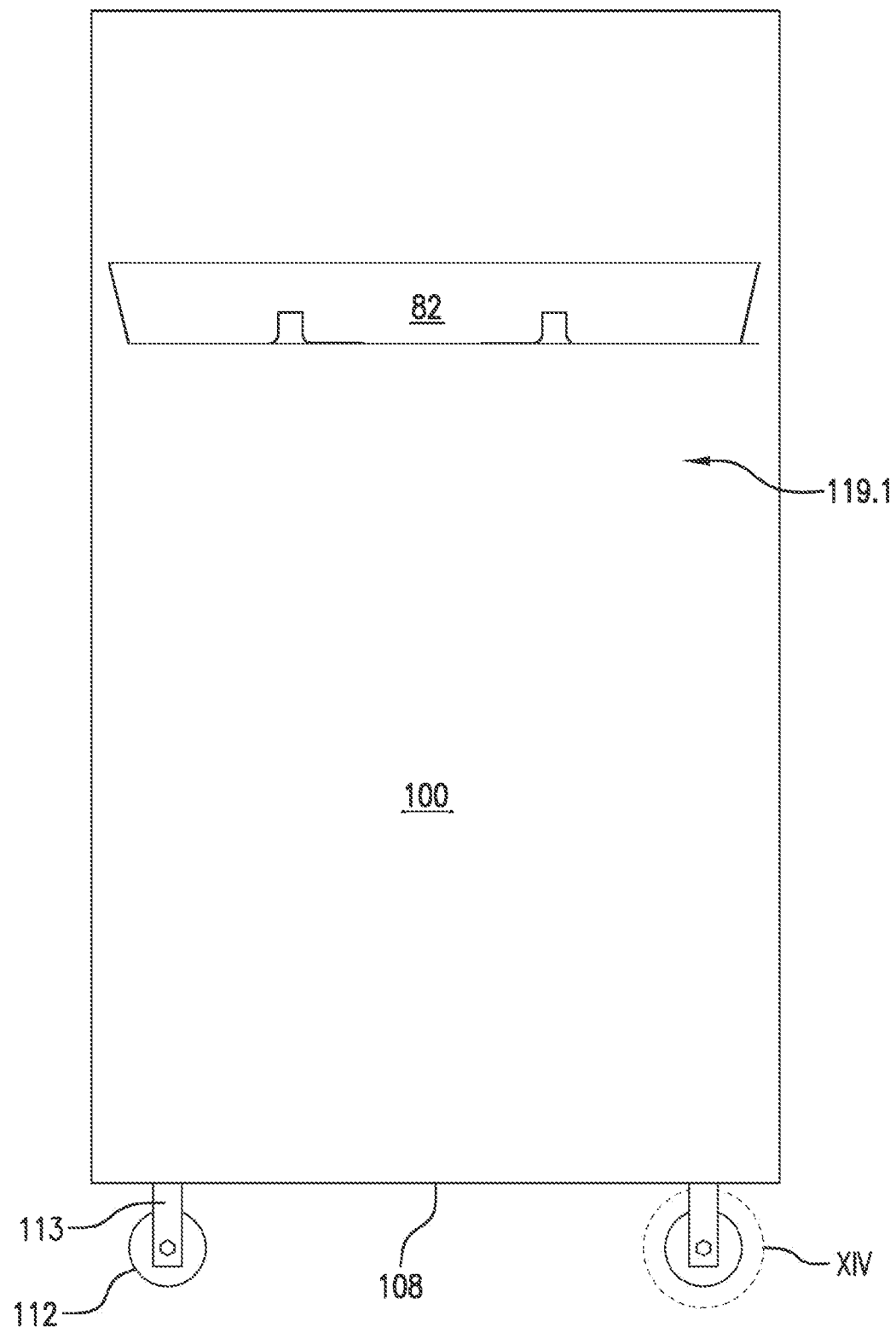
FIG. 11 is a schematic side view of the container of FIGS. 7-10.
Figure 12:
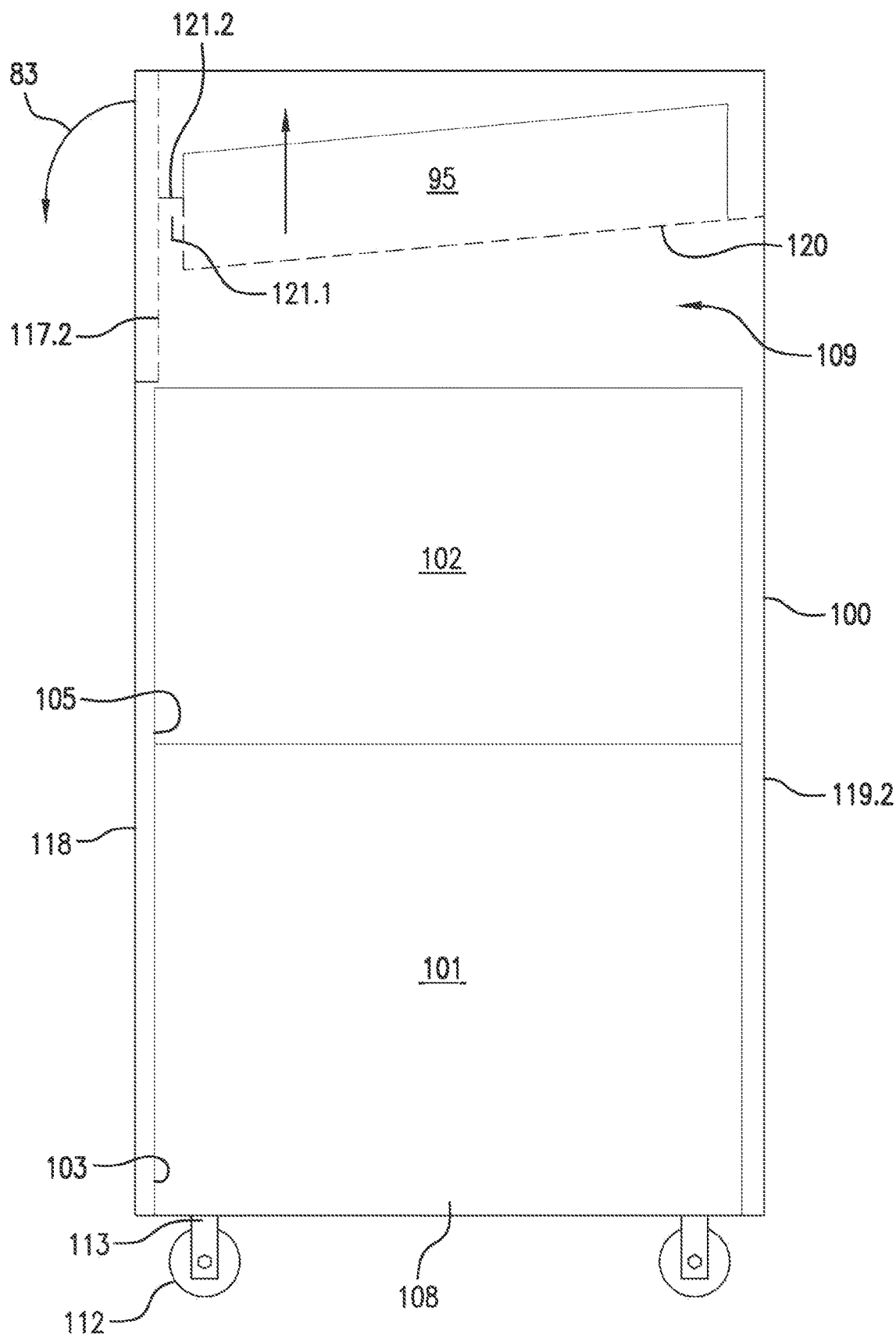
FIG. 12 is a side view of the container of FIG. 11 shown with a transparent side wall to see the inner structure.
Figure 13A:
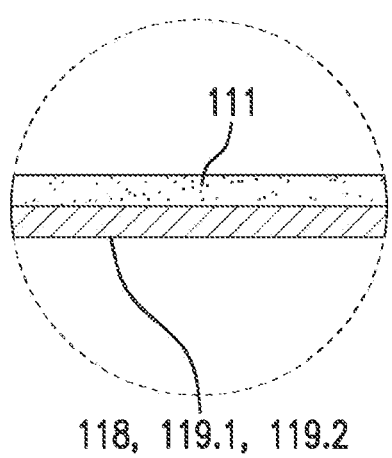
FIG. 13a is an enlarged cut of a wall part of the container according to the marking VII of FIG. 7.
Figure 13B:
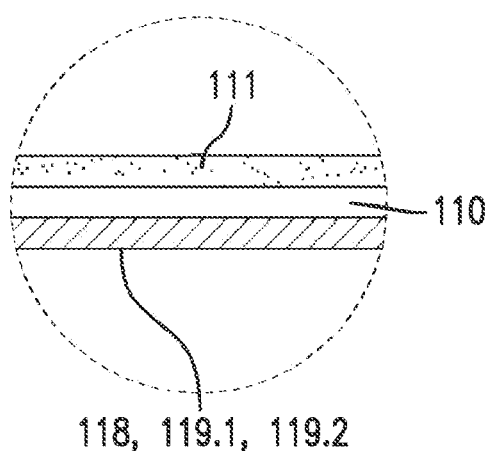
FIG. 13b is an enlarged cut of a wall part of the container according to the marking VII of FIG. 7.
Figure 13C:
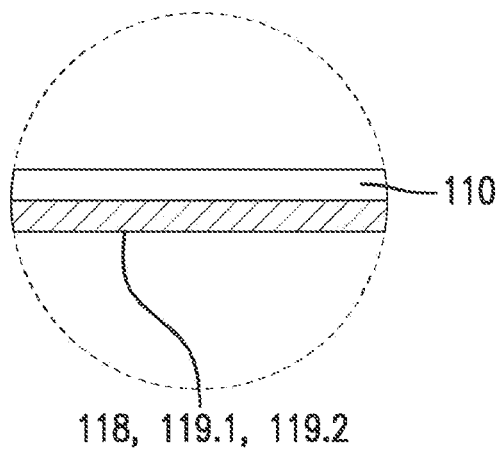
FIG. 13c is an enlarged cut of a wall part of the container according to the marking VII of FIG. 7.
Figure 14:
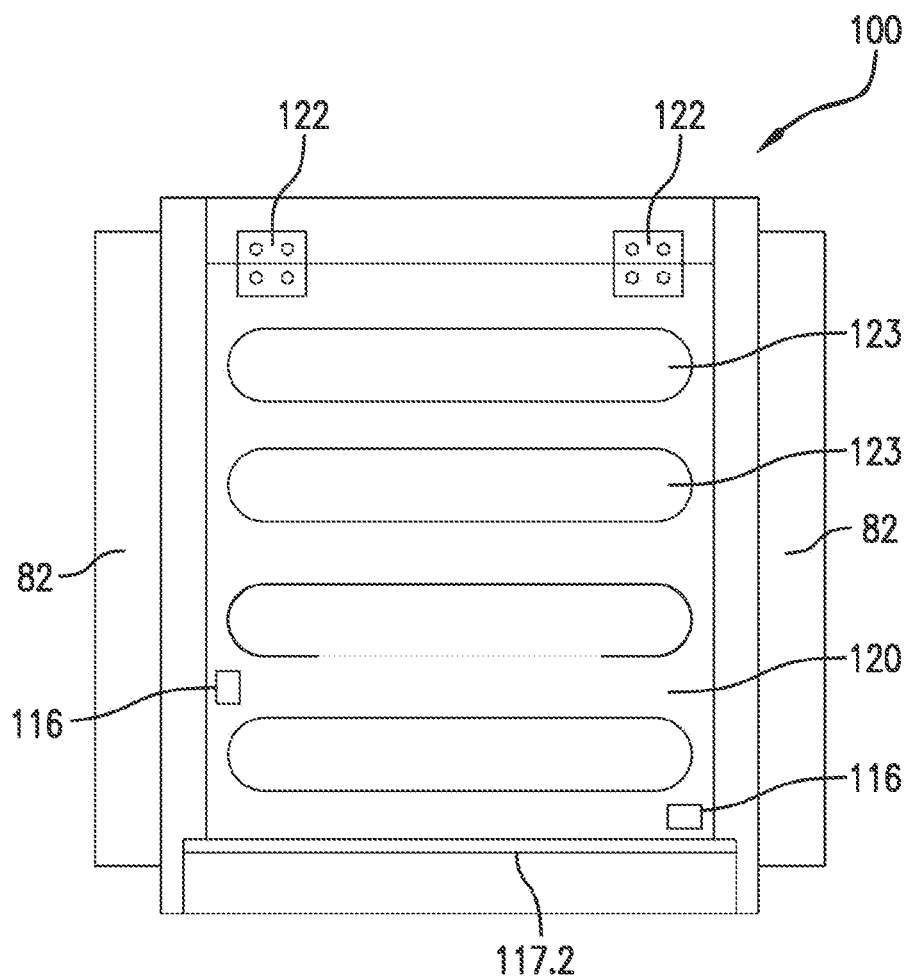
FIG. 14 is a top view of the container of FIGS. 7-13.
Figure 15:
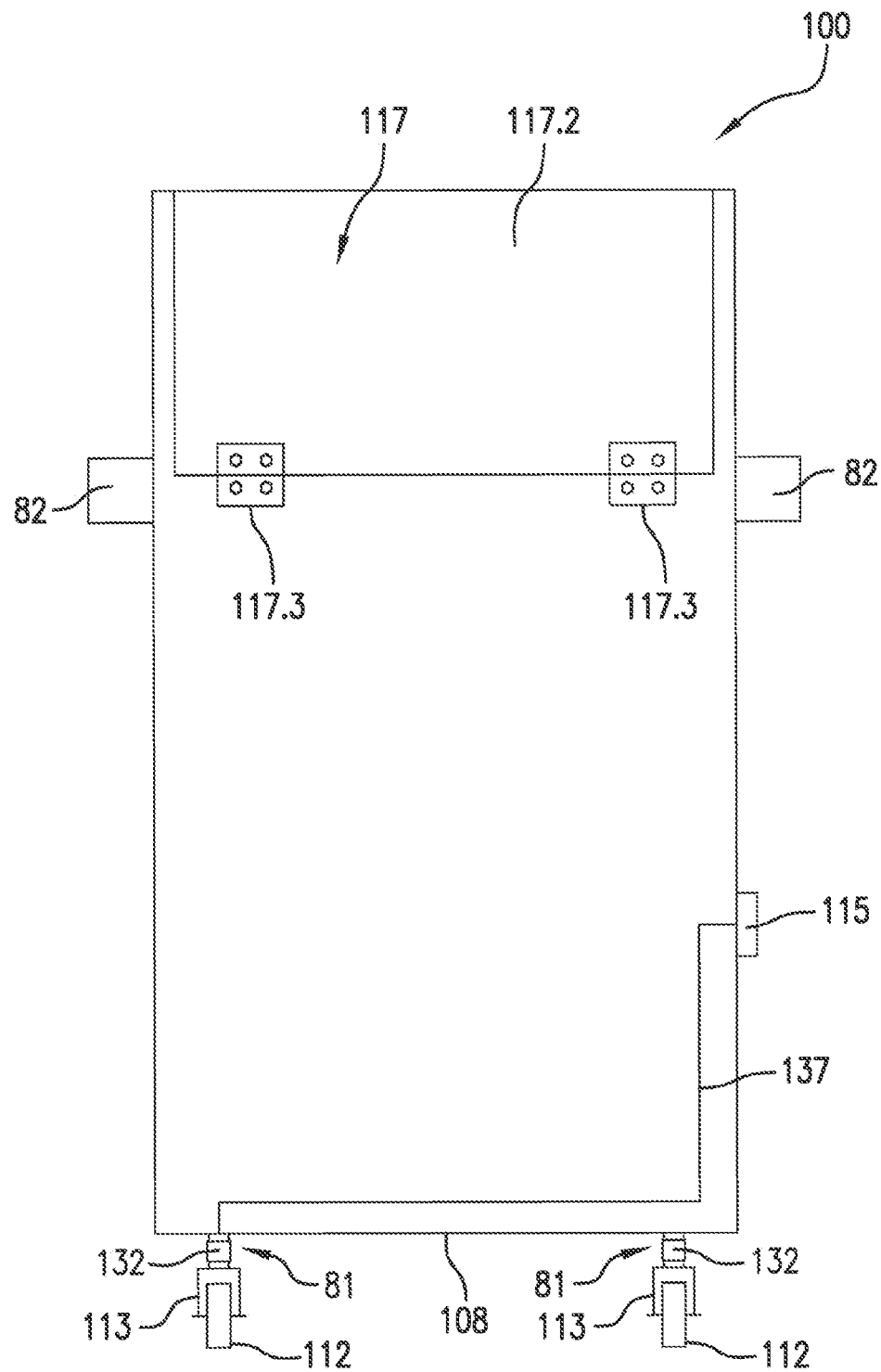
FIG. 15 is a schematic front view of another container for the balancing apparatus or system.
Figure 16:
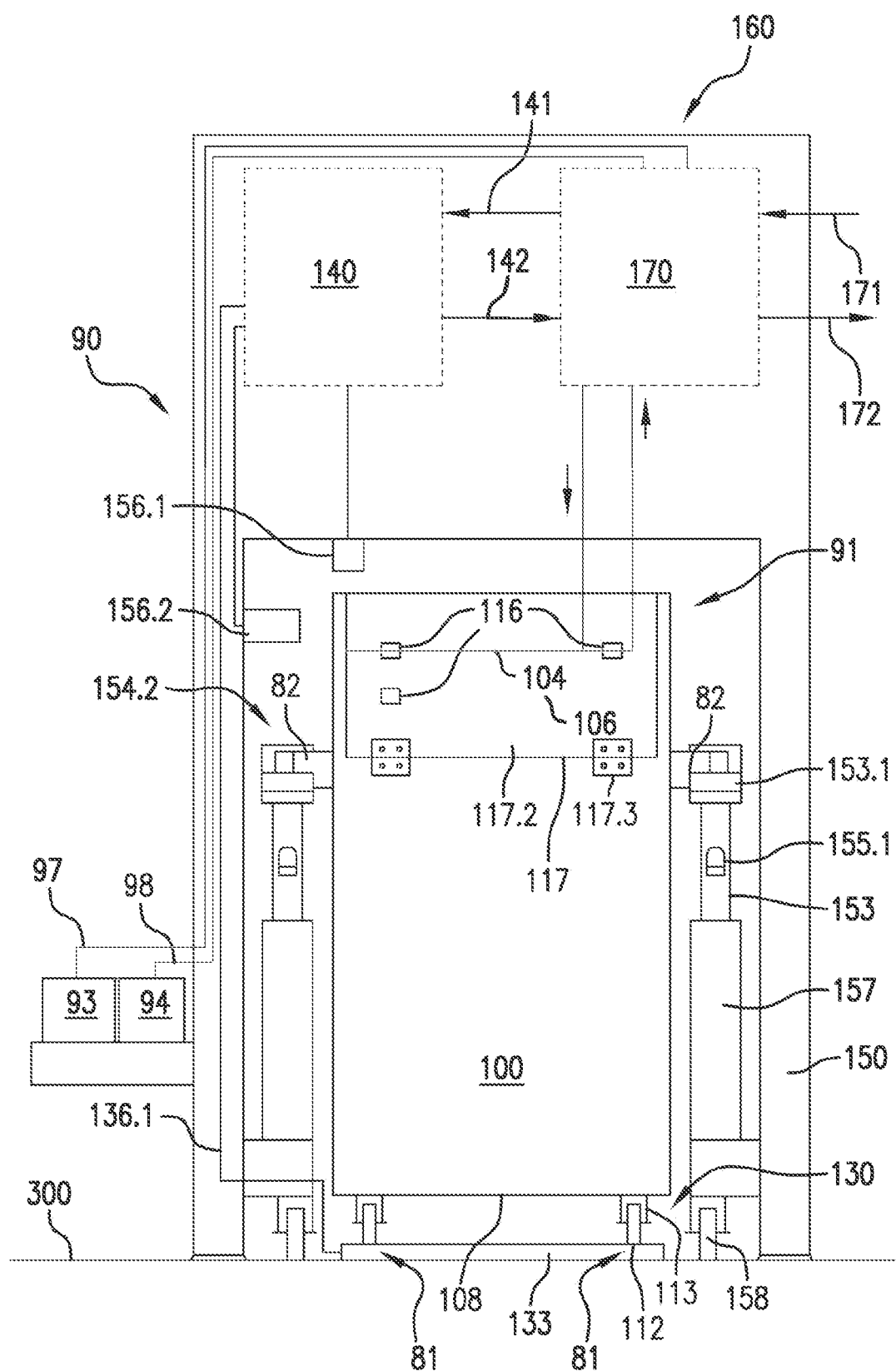
FIG. 16 is a schematic front view of a dialysis apparatus or system with a container located inside the support housing.
Figure 17:
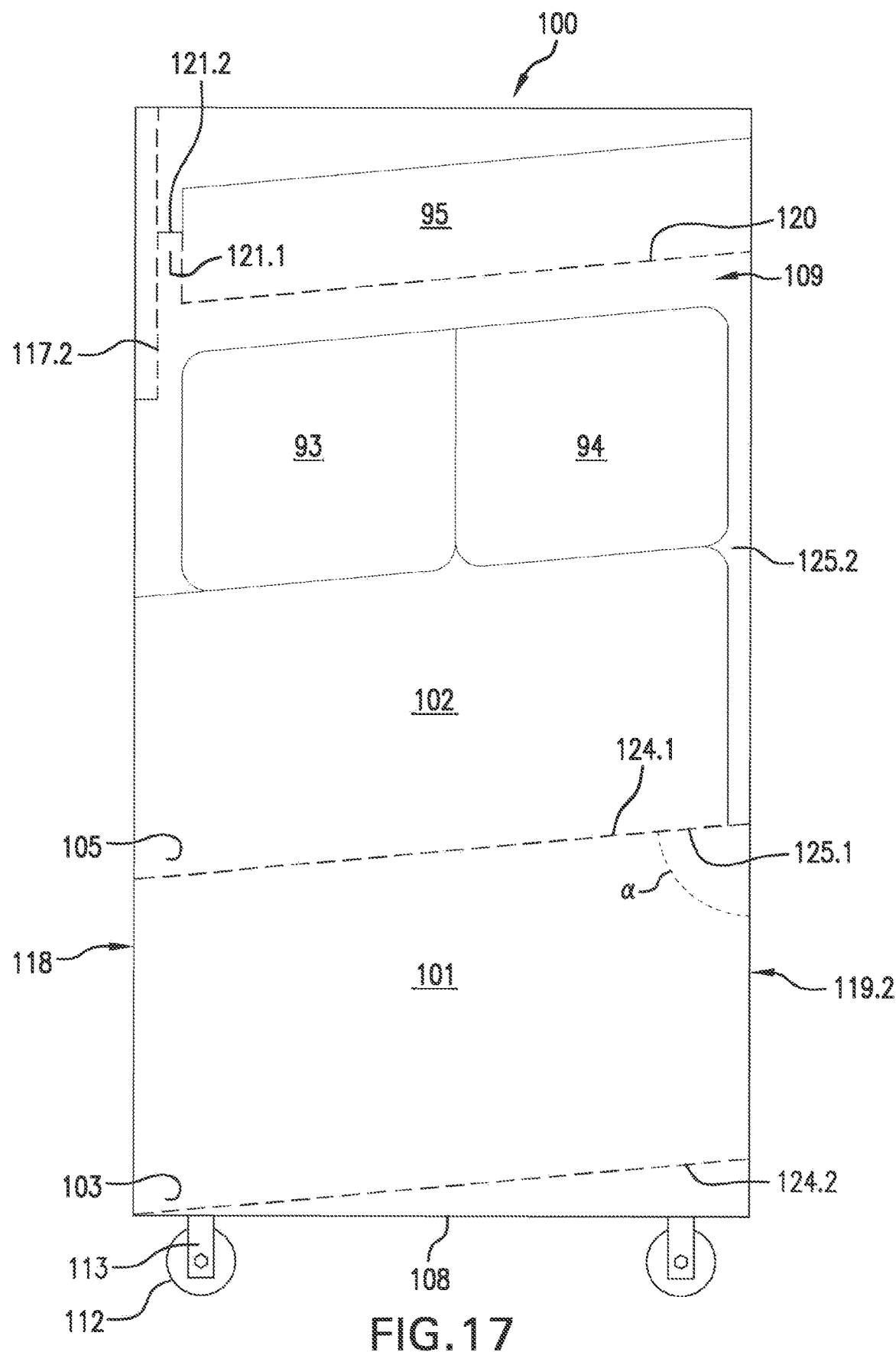
FIG. 17 is a transparent side view of another container for the balancing apparatus or system.
Figure 18:
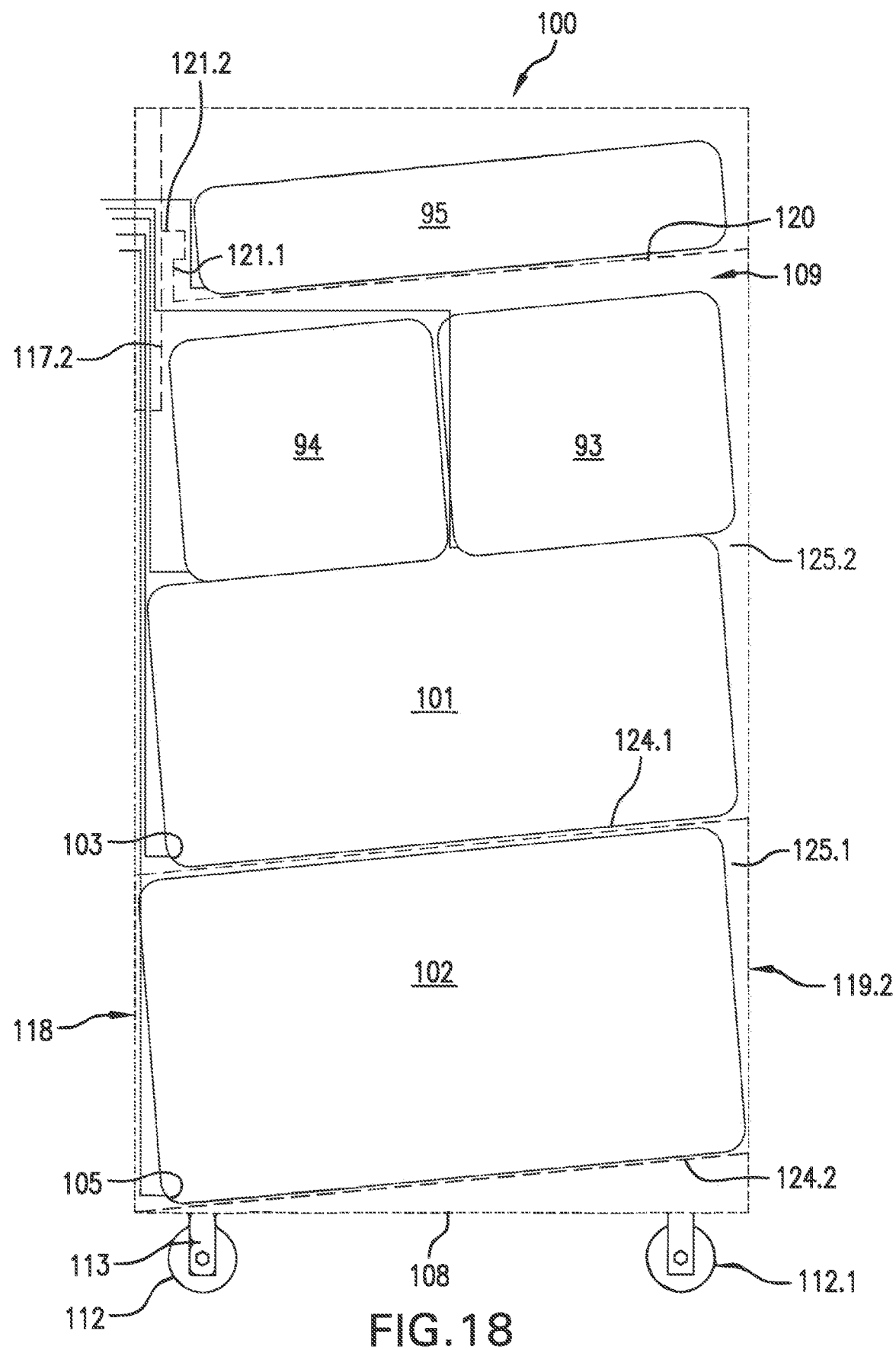
FIG. 18 is a transparent side view of another container for the balancing apparatus or system.
Figure 19:
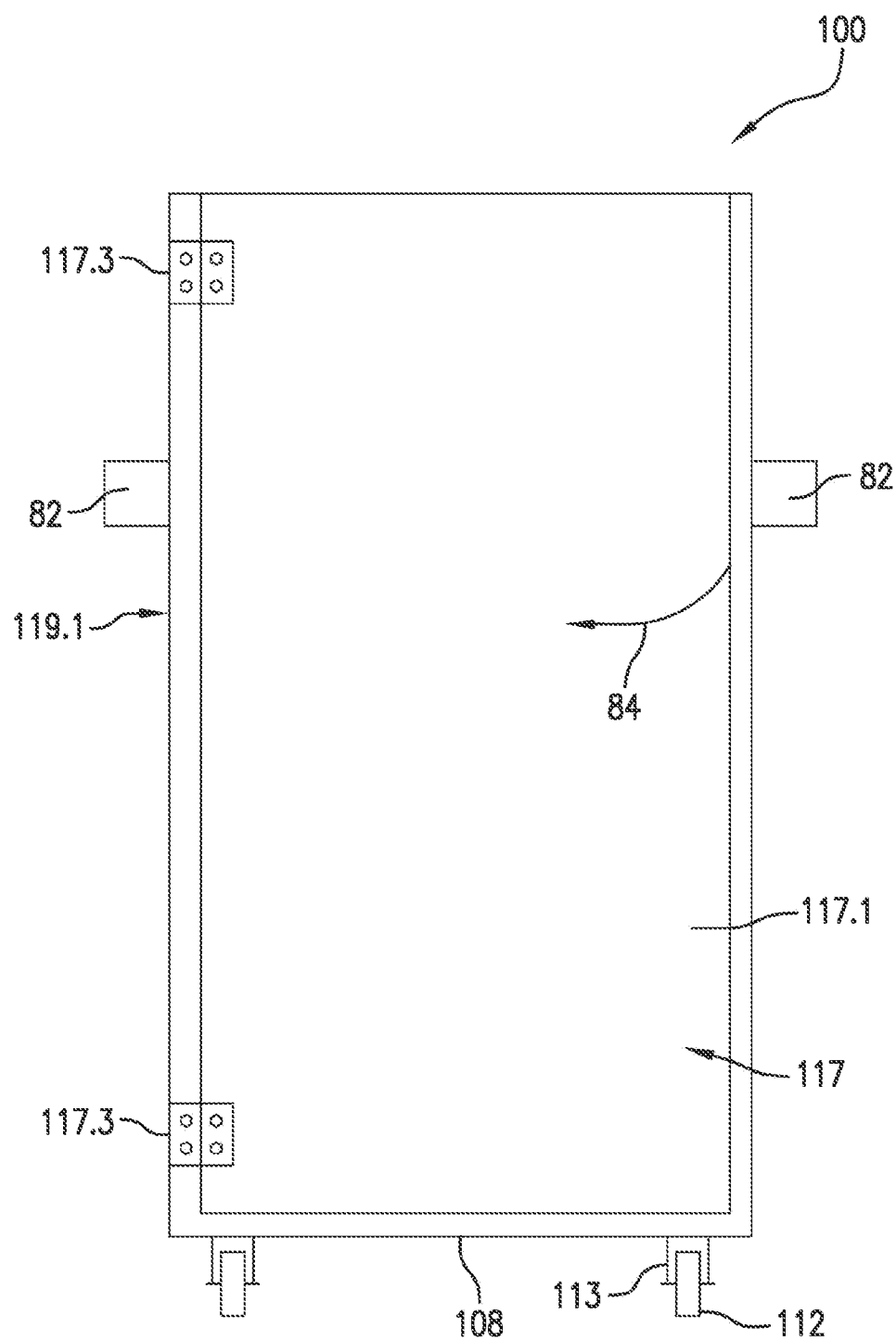
FIG. 19 is a front view of another container for the balancing apparatus or system.
Figure 20:
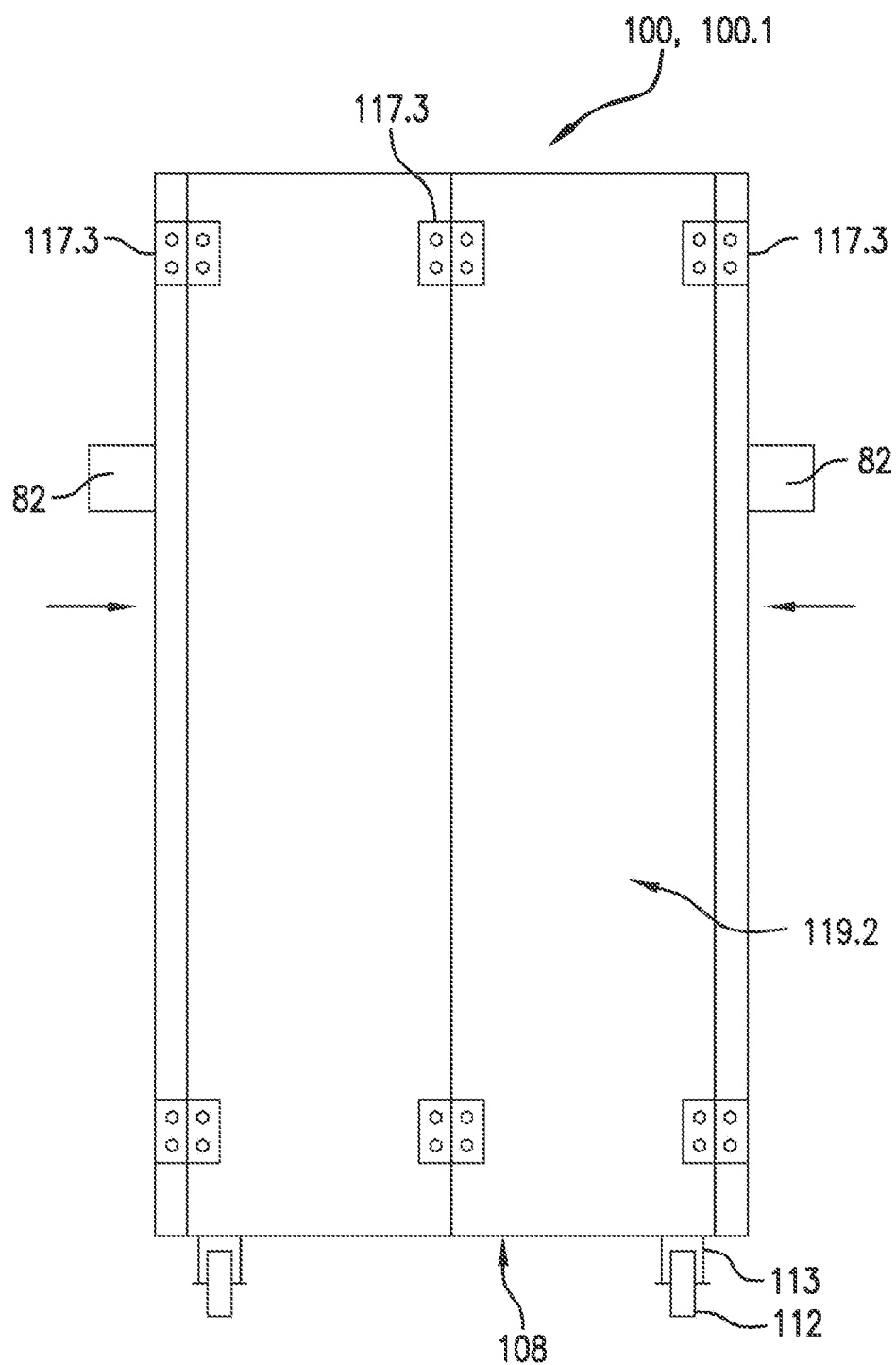
FIG. 20 is a back view of another container for the balancing apparatus or system.
Figure 21:
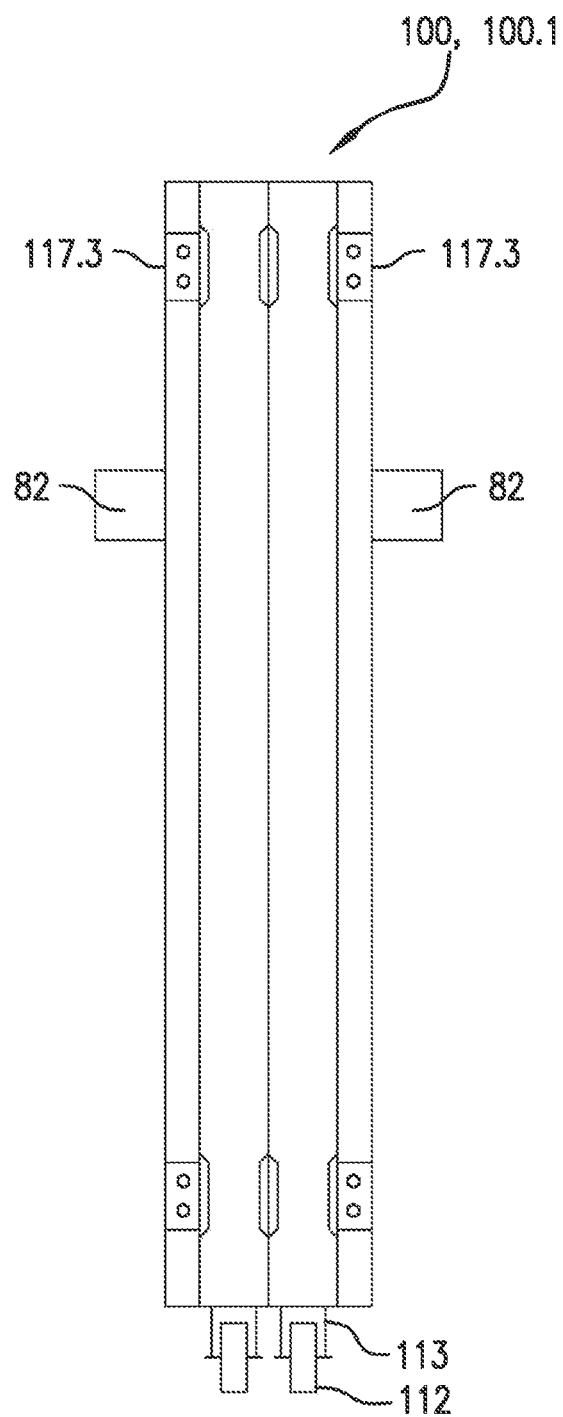
FIG. 21 shows the container according to FIG. 20 in a collapsed state.
Figure 22:
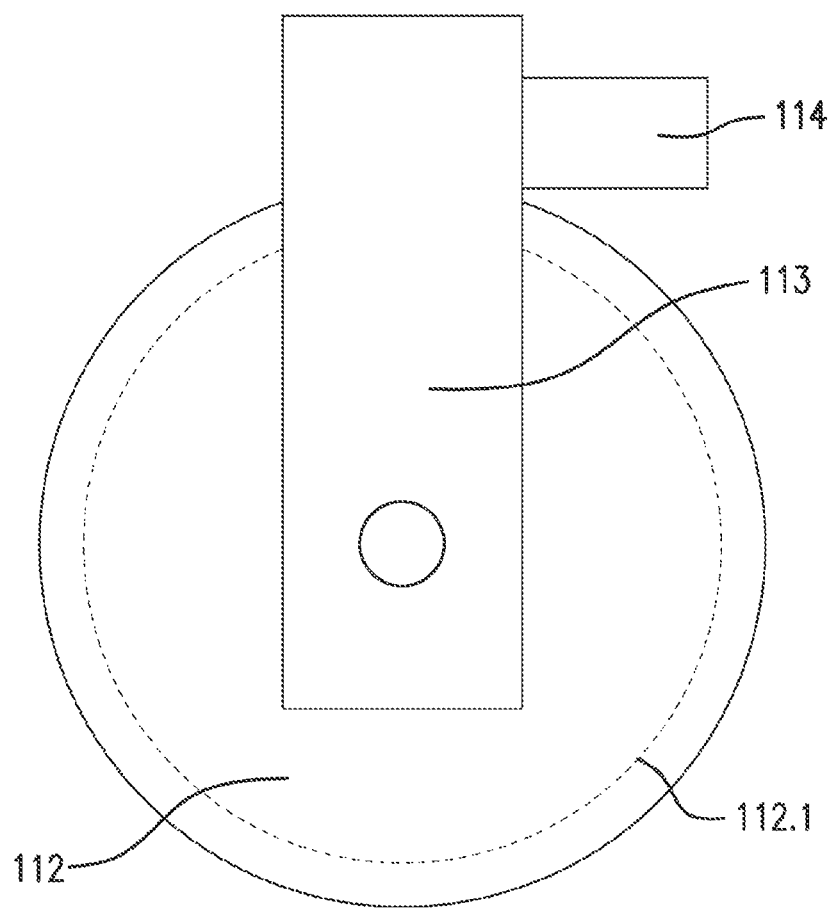
FIG. 22 shows an enlarged view of a roller of the container according to the marking XIV of FIG. 11.
Figure 23:
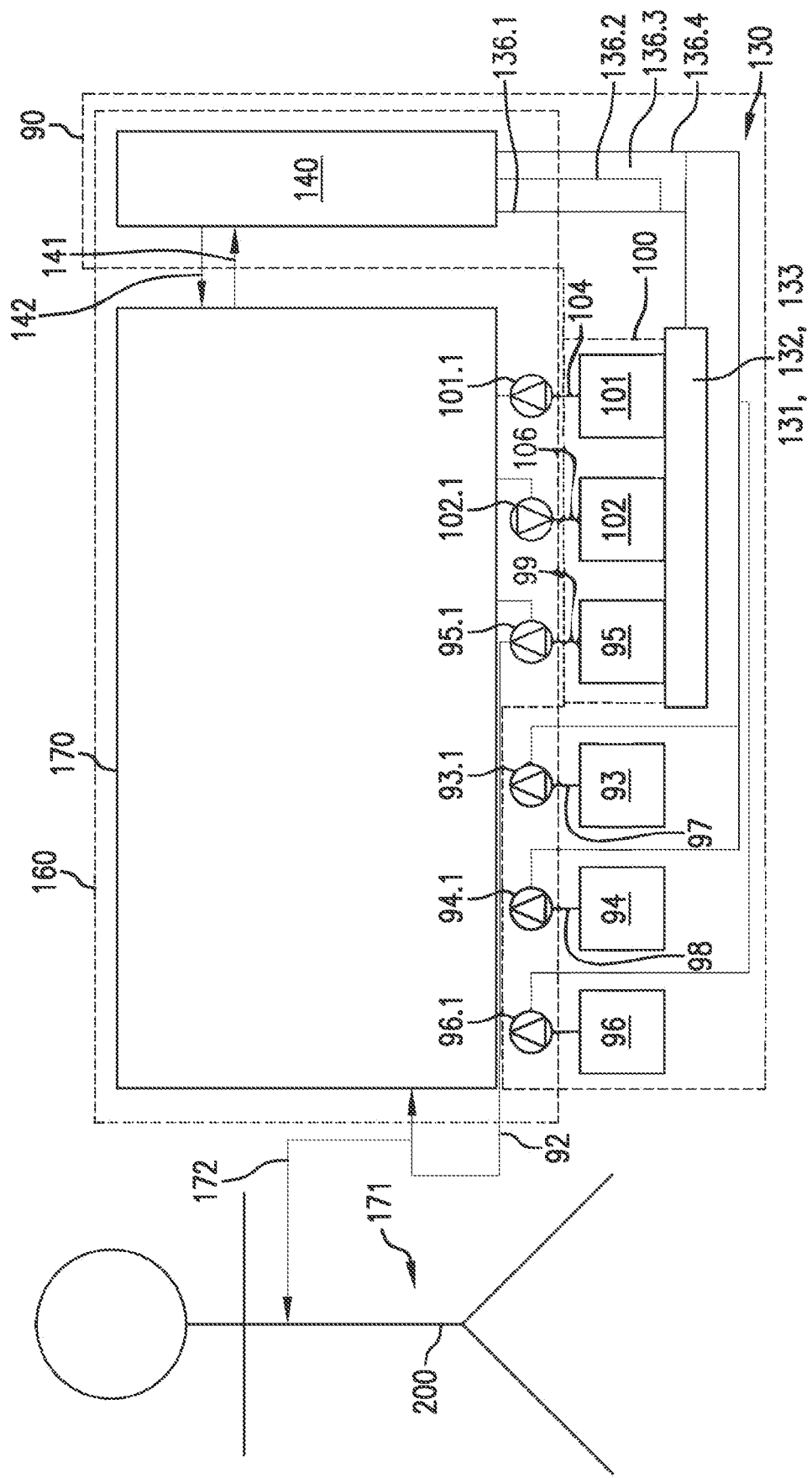
FIG. 23 is a functional scheme of a balancing apparatus or system and a dialysis apparatus or system.
Figure 24:
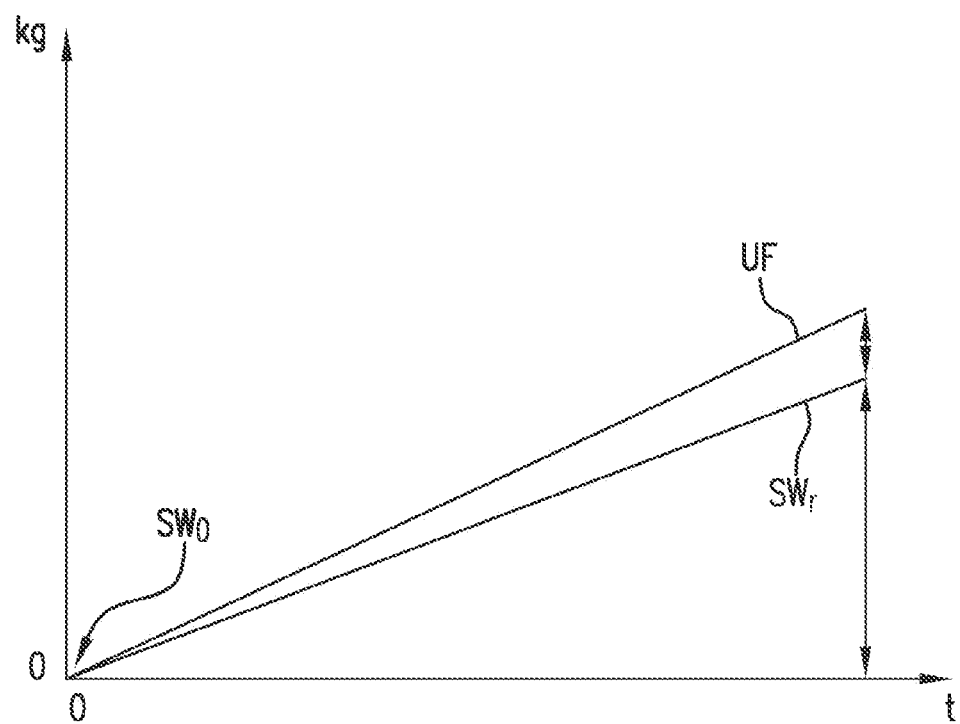
FIG. 24 shows a diagram illustrating the function of a balancing method.

Referring to FIG. 6B, the dialysis system contains a biological fluid circuit 76 with two dialyzers 64A and 64B. Each of the dialyzers 64A and 64B contains a biological fluid compartment, a dialysate compartment, and a semipermeable membrane 65A, 65B that separates the compartments. The dialyzers 64A, 64B are fluidically connected in parallel. A biological fluid such as blood from the patient is pumped through the blood compartments of the dialyzers 64A, 64B by a pump 66.

The system of FIG. 6B provides a dialysate reservoir 67 for storing regenerated dialysate. Dialysis fluid from the dialysate reservoir 67 is pumped through the dialysate compartments of the dialyzers 64A, 64B by a first dialysate pump 68. In order to bring the electrolytes and other important substances to desired concentrations, substitution fluids 69, 70 may be supplied to the dialysate via respective pumps 71, 72. After passing through the dialysate compartments of the dialyzers 64A, 64B, the dialyzing fluid with the added fluids taken from the patient are supplied to the dialysate reservoir 67 via a second dialysate pump 73.

From the dialysate reservoir 67, a flow of dialysate is provided to a dialysate regeneration unit 74. The internal set up of the dialysate regeneration unit 74 is identical to the internal set-up of the dialysate regeneration unit 29 shown in FIG. 6A. The dialysate regeneration unit 74 comprises two flow paths, an acidic flow path and an alkaline flow path that are fluidically connected in parallel. Each of the flow paths contains a detoxification unit.

Referring to FIG. 6B, a separate dialysate regeneration circuit 75 is provided for regenerating the dialysis fluid contained in the dialysate reservoir 67. The dialysate regeneration circuit 75 (tertiary circuit) is decoupled from the biological fluid cleaning circuit. The biological fluid cleaning circuit comprises the biological fluid circuit 76 (primary circuit) and the dialysate circuit (secondary circuit). By decoupling the dialysate regeneration circuit from the dialysate circuit, system parameters like flow, temperature and pH are independently adjustable to the needs of the two different processes. For example, dialysate flow during the biological fluid cleaning process may be between 150-3000 ml/minute, whereas during the regeneration process, dialysate flow may be between 250-5000 ml/minute, preferably between 1000-2000 ml/minute. It may be useful to decouple the two circuits by a dialysate reservoir, as in the dialysate regeneration unit the dialysis fluid has non-physiological pH and temperature values which would result in great damage to the patient's blood. The dialysis fluid contained in the dialysate reservoir 67 may either be cleaned in a continuous operation or in an intermittent operation.

Diagrammatic Representation of an Integrated Dialysis Apparatus or System

Referring to FIG. 1, a biological fluid circuit 3 is provided having a biological fluid inflow 15A and outflow 15B that communicates with a dialysis fluid circuit 2 via a dialyzer 1, 5, 22A, 22B. The dialysis fluid circuit in turn communicates with a dialysate regeneration unit 29, 74 and dialysate regeneration circuit 16, 75 at least in part via a reservoir 67. Heating and/or cooling apparatuses 6 or means for adjusting the pH of the subject fluid may be provided. The dialysis regeneration circuit features an acidic flow path 37 and an alkaline flow path 38 in parallel. Each of the acidic flow path 37 and an alkaline flow path 38 feature a dialyzer or detoxification unit 45, 46. Each dialyzer 1, 5, 22A, 22B features a semipermeable membrane 23A, 23B. Further, each of the acidic flow path 37 and an alkaline flow path 38 feature a regeneration pump 43, 44. An acidic solution 39 and a basic solution 41 may be added to the acidic flow path 37 and the alkaline flow path 38, respectively. One or more other fluids may be added to the dialysate or removed from the dialysate 18. Various fluid lines 97, 98 are provided as needed and as appropriate.

Figure 25:
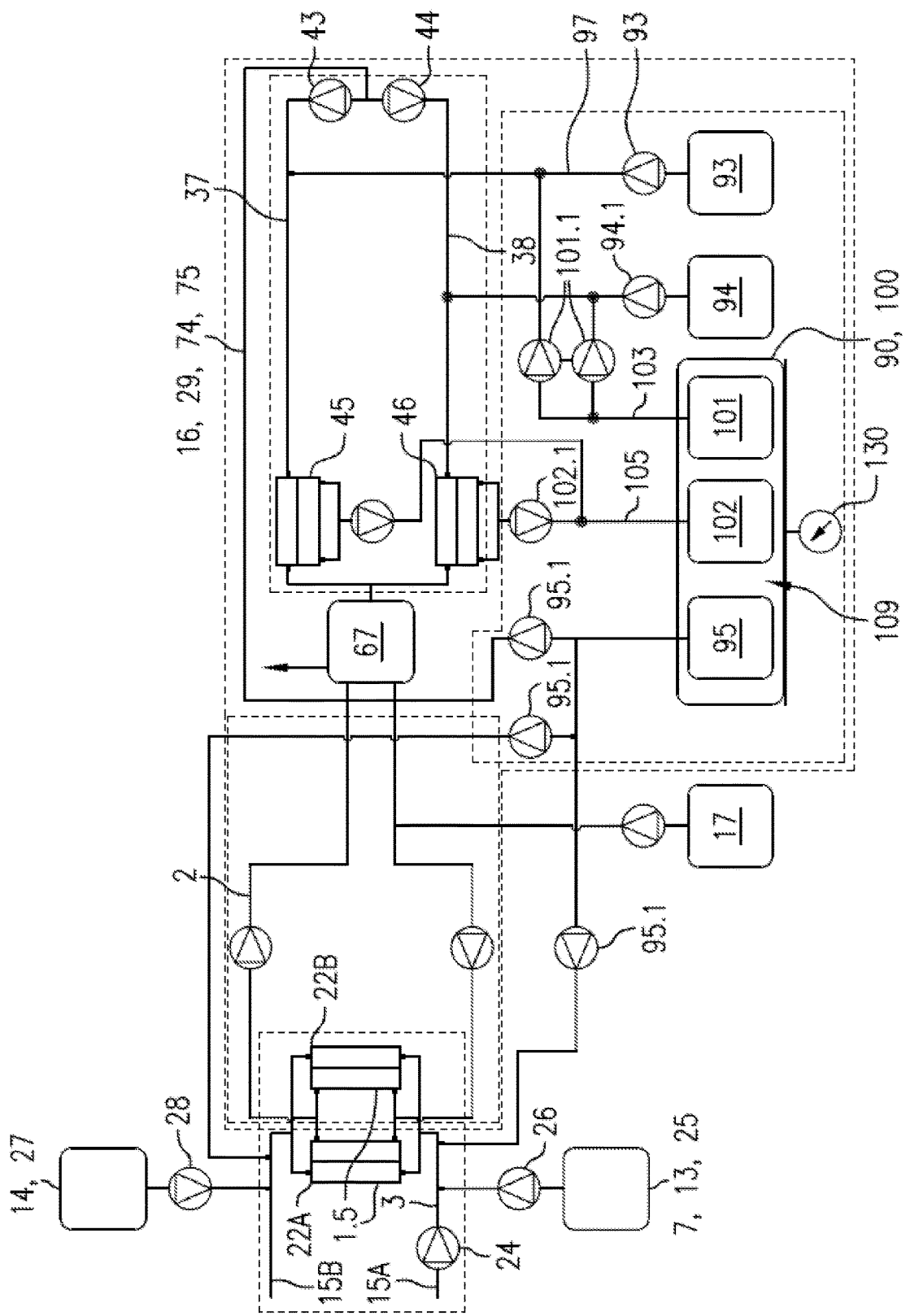
FIG. 25 provides a diagram representing a dialysis apparatus or system according as described herein.
Figure 26:
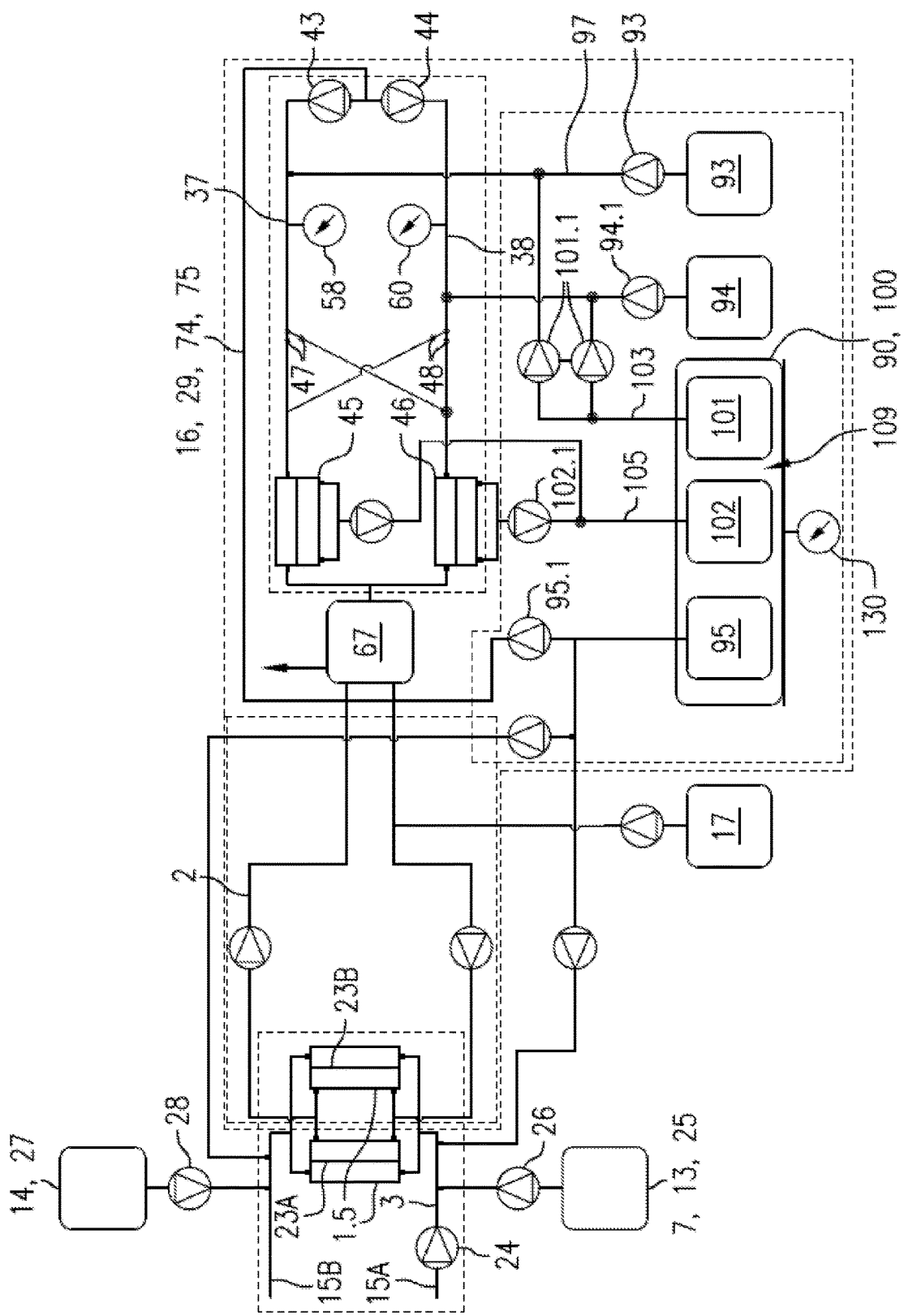
FIG. 26 provides another diagram representing a dialysis apparatus or system as described herein. The dialysis apparatus or system features a cross switch and means for measuring the fluid (e.g. pH).
Figure 27:
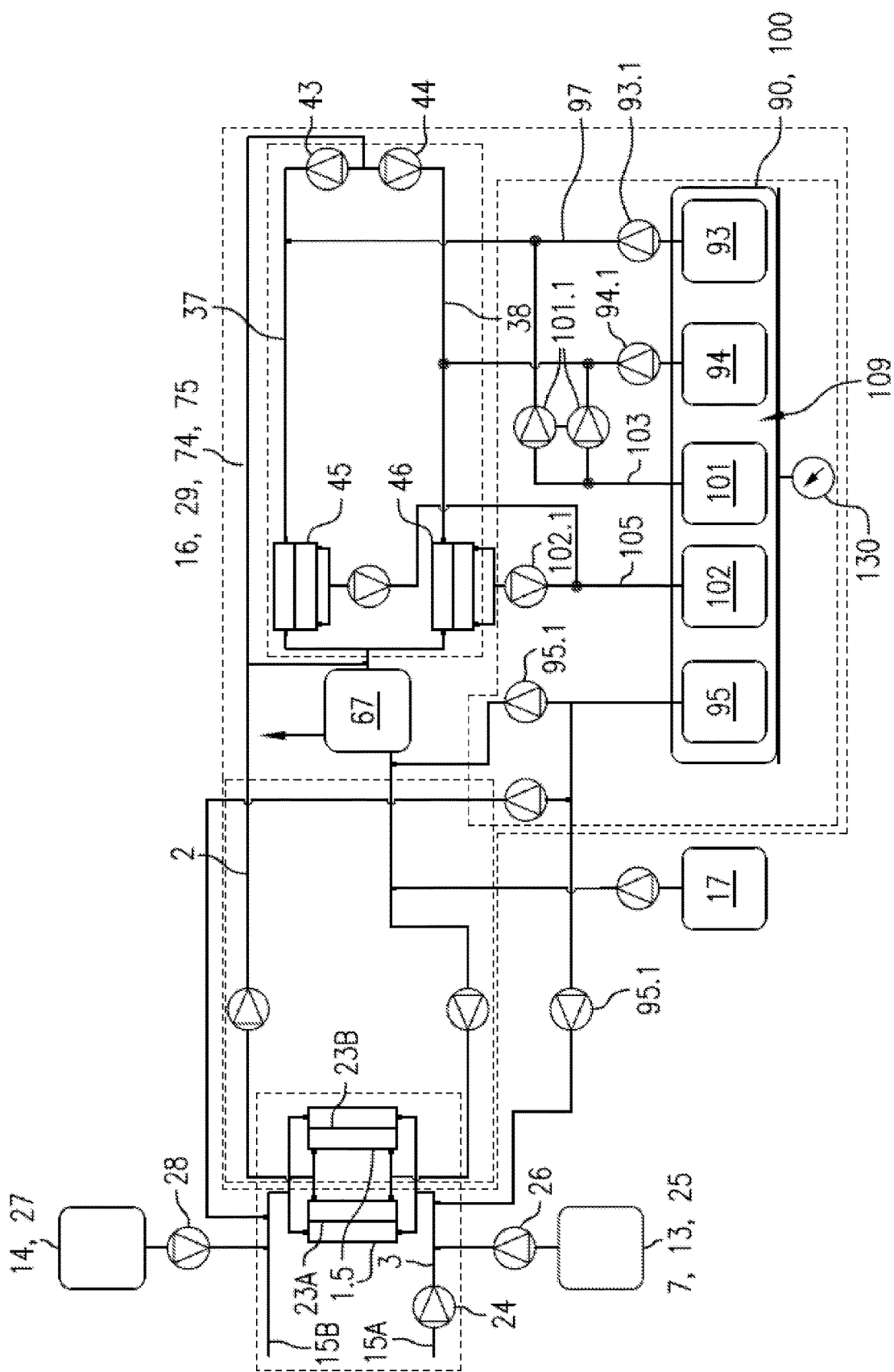
FIG. 27 provides still another diagram representing a dialysis apparatus or system as described herein.
Figure 28:
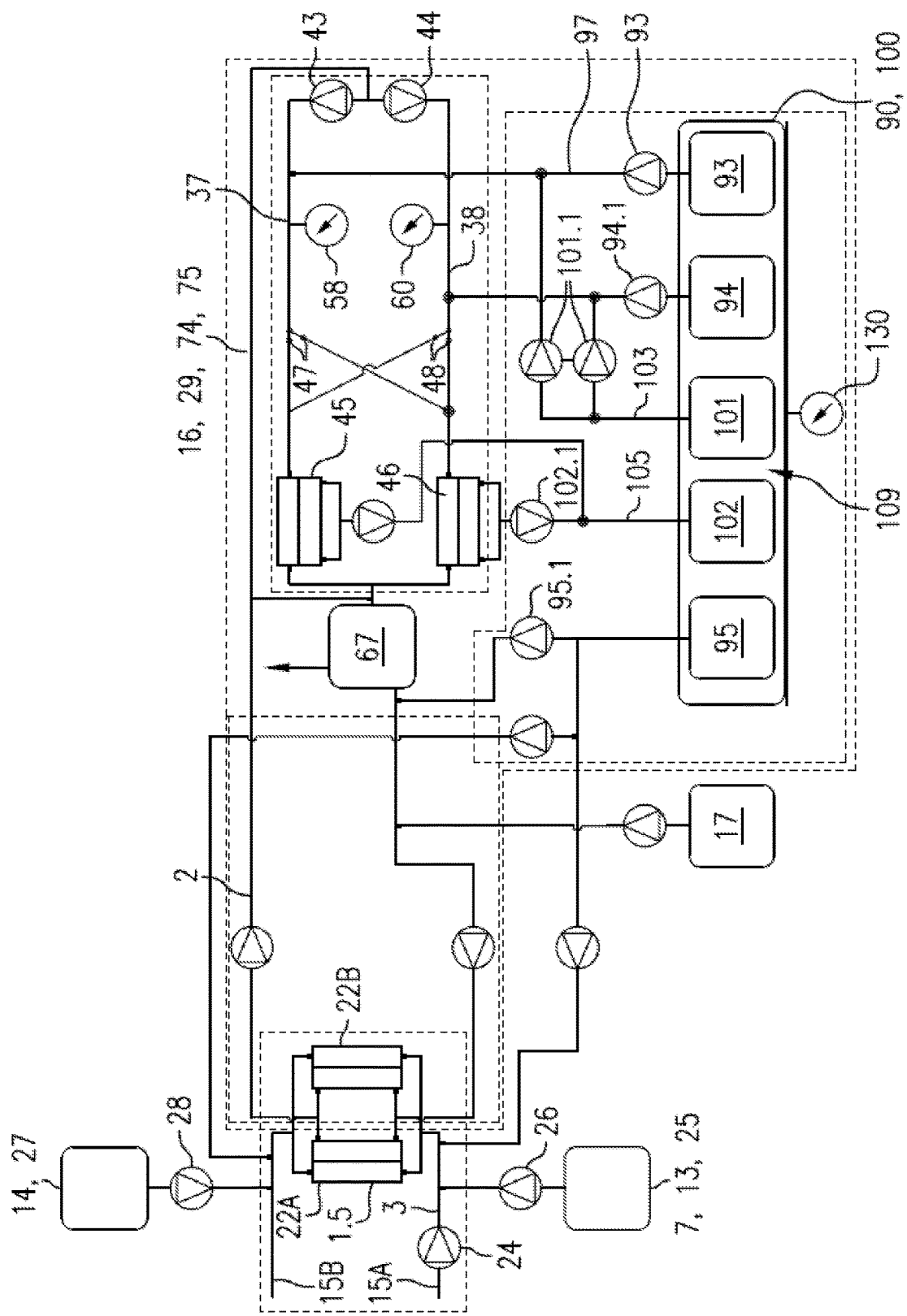
FIG. 28 provides yet another diagram representing a dialysis apparatus or system as described herein.
Figure 29:
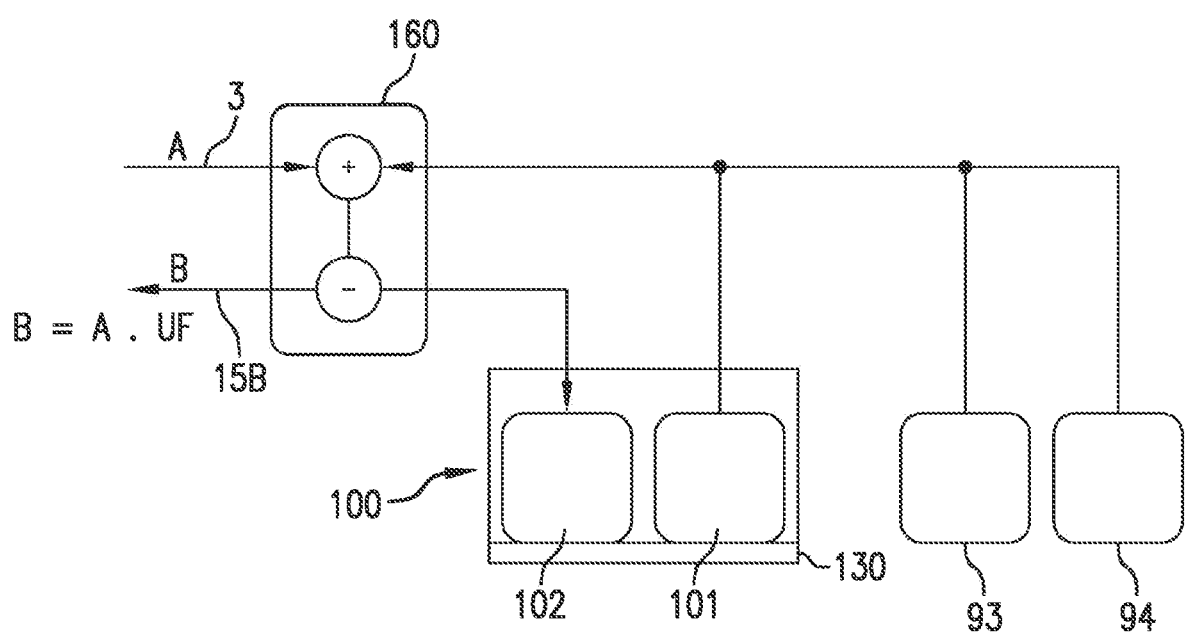
FIG. 29 provides yet one more diagram, this one a simplified version, representing a dialysis apparatus or system as described herein.

FIG. 25 provides a diagram representing a dialysis apparatus or system as described herein having three reservoirs in communication with a weighing means. FIG. 26 provides another diagram representing a dialysis apparatus or system as described herein, having three reservoirs in communication with a weighing means. The dialysis apparatus or system features a cross switch and means for measuring pH value, temperature, turbidity, speed (sound speed), concentration, density and conductivity. FIG. 27 provides still another diagram representing a dialysis apparatus or system as described herein having five reservoirs in communication with a weighing means. FIG. 28 provides yet another diagram representing a dialysis apparatus or system as described herein having five reservoirs in communication with a weighing means and a cross switch and means for measuring pH value, temperature, turbidity, speed (sound speed), concentration, density and conductivity. FIG. 29 provides yet one more diagram, this one a simplified version, representing a dialysis apparatus or system as described herein.

Referring to FIG. 25, a biological fluid circuit 3 is provided having a pump 24. A device 7, 13, 25 for adding substituent to the biological fluid circuit using a pump 26 is further provided. The biological fluid interfaces with the dialysis fluid circuit 2 in a dialyzer 1, 5, 22A, 22B and is returned to the patient via an outflow 15B, such as a venous blood line. A regeneration circuit or dialysate regeneration circuit 16, 29, 74, 75 is provided for regenerating the dialysate. The regeneration circuit 16, 29, 74, 75 is in communication with the dialysis fluid circuit 2 interfacing with a reservoir 67. The dialysis regeneration circuit features an acidic flow path 37 and an alkaline flow path 38 in parallel. Each of the acidic flow path 37 and an alkaline flow path 38 feature a dialyzer or detoxification unit 45, 46. Further, each of the acidic flow path 37 and an alkaline flow path 38 feature a regeneration pump 43, 44. In addition, a balancing apparatus or system is provided featuring a balancing device 90 or container 100 having a receiving space 109. In the receiving space 109 are three reservoirs 101, 102, 95. Outside the receiving space are two further reservoirs 93, 94. A weighing means 130 is provided for measuring the weight of the balancing device 90 or container 100 including the three reservoirs 101, 102, 95 contained in the receiving space 109 therein.

The first reservoir 101 may be in communication with the acidic flow path 37 and the alkaline flow path 38 via a fluid outlet 103 featuring a pump 101.1. The second reservoir 102 may be in communication with the regeneration circuit 16, 29 via a fluid inlet 105 featuring a pump 102.1. The further reservoir 95 may be in communication with the dialysis circuit 2 and/or the biological fluid circuit 3 via a fluid outlet featuring different pumps. Similarly, reservoirs 93 and 94 may be in communication with the regeneration circuit 16, 29, 74, 75 via various lines 97 featuring pumps 93.1 and 94.1. One or more additional fluid may be added to the dialysate 17. Further, one or more postdilution fluid 14, 27 may be added to the biological fluid outflow, e.g. venous blood line 15B, using a pump 28 is further provided.

Referring to FIG. 26, the elements are provided in the same configuration as in FIG. 25 except that a cross switch via a valve mechanism comprising switching valves 47, 48 and means for measuring pH value, temperature, turbidity, speed (sound speed), concentration, density and conductivity 58, 60 and temperature regulation units are located on the acidic flow path 37 and the alkaline flow path 38.

Referring to FIG. 27, the elements are provided in the same configuration as in FIG. 25 except that five reservoirs 101, 102, 93, 94 and 95 are provided in the receiving space 109 of the balancing device 90 or container 100. A weighing means 130 is provided for measuring the weight of the balancing device 90 or container 100 including the five reservoirs 101, 102, 93, 94 and 95 contained in the receiving space 109 therein.

Referring to FIG. 28, the elements are provided in the same configuration as in FIG. 26 except that five reservoirs 101, 102, 93, 94 and 95 are provided in the receiving space 109 of the balancing device 90 or container 100. A weighing means 130 is provided for measuring the weight of the balancing device 90 or container 100 including the five reservoirs 101, 102, 93, 94 and 95 contained in the receiving space 109 therein. As in FIG. 26, a cross switch via a valve mechanism comprising switching valves 47, 48 and means for measuring pH value, temperature, turbidity, speed (sound speed), concentration, density and conductivity 58, 60 and temperature regulation units are located on the acidic flow path 37 and the alkaline flow path 38.

Referring to FIG. 29, a diagrammatic representation is provided to clarify that a biological fluid A enters a dialysis apparatus or system 160 (comprising a dialysis fluid circuit 2 and optionally a dialysate regeneration circuit 16, 29, 74, 75) as described herein via a biological fluid circuit 3. Dialysis fluid containing a dialysate is provided in a dialysis circuit 2 that interfaces with the biological fluid A provided in the biological fluid circuit 3 only at the point of a semipermeable membrane contained in a dialyzer. Additional fluids may be provided to adjust the binding properties of an unwanted protein-binding substance to be removed and/or to replace the dialysis fluid within the dialysis apparatus or system continuously, partially or completely. One, two or more reservoirs 101, 102 may be placed in weighing communication with a weighing means 130 (such as in a balancing device 90 or container 100) to measure the weight of one or more fluid provided to adjust the binding properties of an unwanted protein-binding substance to be removed or to measure the weight of an ultrafiltrate obtained from the biological fluid during the dialysis procedure. The biological fluid B, which is returned to the biological fluid circuit in a biological fluid outflow (e.g. venous blood line 15B), is the biological fluid A, that enters a dialysis apparatus or system, less the ultrafiltrate. That is, fluids from the one, two or more reservoirs 101, 93 and 94 and from the biological fluid circuit 3 may be added to the dialysis apparatus or system. The fluid in the reservoir 102 may be removed from the dialysis apparatus or system. The biological fluid B may also leave the dialysis apparatus or system. The ultrafiltration UF or a bolus of the biological fluid may be removed or added from the dialysis circuit through the semipermeable membrane and thereby measured by the weighing means 130. The weight of the balancing device 90 or container 100 may be increased/influenced by the addition of the fluid from the one, two or more reservoirs 93 and 94 provided to adjust the binding properties of an unwanted protein-binding substance to be removed and the ultrafiltration/bolus from the biological circuit.

Balancing Apparatus or System and Method balancing apparatus, system, and method for balancing the volume or flow of fluids in a dialysis apparatus or system, suitable for dialyzing a biological fluid containing a protein-binding substance to be removed, is provided within the systems, apparatuses and methods described herein.

Balancing Apparatus or System

The balancing apparatus or system as represented generally in FIGS. 7-24 features a balancing support 91 having at least a first reservoir 101 for a first fluid that includes a usable fluid for the dialysis apparatus or system such as a dialysis fluid, and a second reservoir 102 for a second fluid that may include a waste fluid from the dialysis apparatus or system. The first reservoir 101 has at least one fluid outlet 103 for fluid communication with the dialysis apparatus or system. The second reservoir 102 may contain at least one fluid inlet 105 for fluid communication with the dialysis apparatus or system. The balancing apparatus or system further features a weighing means 130 for weighing the balancing support 91, and a controller 140 configured to receive weighing data from the weighing means 130. The balancing apparatus or system is suitable for balancing the total fluid volume within the dialysis apparatus or system. The total fluid volume may include one or more usable fluids such as a dialysis fluid, a dialysate, a waste fluid from the subject or patient undergoing the dialysis, and a concentrate suitable for adjusting the pH of or providing a substitute to the dialysis fluid or dialysate.

A deviation of balanced weight in excess of a predefined threshold may signal the controller 140 to interrupt operation of the dialysis apparatus or system. Similarly, deviation of balanced weight in excess of or below a predefined threshold may signal the controller 140 to modify operation of the dialysis apparatus or system such as, for instance, increasing or decreasing flow rate of one or more fluids within the dialysis apparatus or system. As such, the balancing apparatus or system may be used to maintain a relatively constant volume of fluids within the dialysis apparatus or system by effectively increasing or decreasing flow of one or more fluids within the dialysis apparatus or system as desired or as needed.

The balancing support 91 features a single and, at least at its bottom and side walls, fluid tight container 100 having at least one rigid point of application for the weighing means of the balancing device 90. The fluid tight container 100 has an internal fluid tight receiving space 109 for housing the first 101 and second reservoir 102 of the balancing device 90. The maximum loading capacity of the fluid tight receiving space of the container exceeds the maximum load of the first reservoir and the second reservoir jointly.

Due to the fluid tightness of the container housing at least the first reservoir 101 and the second reservoir 102, both reservoirs optionally being formed as flexible containers, substantially no fluid, neither a usable fluid such as a dialysis fluid, dialysate, or concentrate, nor a waste fluid, is lost due to leakage at any of the reservoirs or any of the fluid inlets and outlets including the fluid lines from the outlets or inlets to the dialysis apparatus or system. Therefore, balancing the volume or flow of fluids using the balancing apparatus or system described herein accounts for any liquids that may leak from any of the reservoirs. Such leaking fluids are collected by the fluid tight container and are therefore included in the balancing calculations performed by the balancing apparatus or system. A leakage in the closed dialysate circuit may be detrimental to balancing fluids. As such, the dialysis circuit may be provided in a closed fluid tight space with liquid sensors to detect any leakage.

The container 100 has a stiff structure. Such a stiff structure is provided by a suitable material used to form the container, e.g. a stiff metal. The container 100 may be formed of a frame and a sheeting to enhance stiffening. Due to its stiff structure, the container 100 may absorb higher forces without torsion of the container body. Such torsion of the container body may influence the weighing result of the weighing means. Torsion related measuring errors hence are avoided.

The stiff structure of the container is provided with a fluid tight lining 111, and the lining may be formed of a fluid tight film, a foil, or a laminate. This fluid tight lining 111 insures that the fluid tightness of the container 100 is provided even when a planking or sheeting of the stiff frame of the container is missing. The stiff structure of the container 100 may also be provided with a fluid tight coating 110 that further insures the fluid tightness of the container. The fluid tight coating 110 may be used instead of a fluid tight lining 111. The fluid tight coating 110 may be formed of any suitable material known to those of ordinary skill in the art. The stiff structure of the container 100 may be provided with both. The fluid tight coating 110 may be of a different color than the fluid tight lining 111. The coating 110 may feature antibacterial properties. Further, the container 100 may be provided with ultraviolet radiation or ozone. The interior space of the container 109 may have a loading capacity of at least 80 liters, preferably at least 100 liters and even more preferably at least 120 liters. Due to this loading capacity the container may be more easily maintained requiring less personal attention.

The container 100 is often mobile and features at least three or four rollers or wheels 112 arranged at a base part of the container 108. One of the rollers 112 is equipped with a break-member 114 for arresting the roller 112 and thereby arresting movement of the container 100. The rollers 112 and the at least one break member 114 allow the container 100 to be easily handled. Further when the break or breaks are in their breaking position, the container 100 has a stable stand, avoiding any unintentional agitation.

The weighing means 130 features load cells 131, 132, 133. Each of the load cells 131, 132, 133 may be associated with one of the rollers 112. Preferably the respective load cells 131, 132, 133 are arranged in between a roller 112 and a rigid point of application at the base part of the container 108. With the load cells 131, 132, 133 of the weighing means 130 being associated and arranged at the rollers 112, the container 100 may be an autonomous system that may deliver weighing measurements directly to the controller 140. The container 100 may feature an interface of the weighing means 130 for connecting the weighing cells/load cells 131, 132, 133 of the container 100 to the controller 140. The interface 115 may feature either one of a plug and a mating plug and connect via a cable with the controller 140 which may be housed in a different part of the balancing device 91 or may even be housed in the dialysis apparatus or system. Alternatively, the interface 115 may be adapted for wireless communication with the controller and feature a wireless communication device included in the interface.

The container 100 may further feature supporting elements 116 arranged therein for locking and guiding fluid lines (104, 106) connecting the first 101 and second reservoirs 102 with the dialysis apparatus or system. Also, the supporting elements 116 may be used for locking and guiding fluid lines (97-99) of other reservoirs, other than the first 101 and second reservoirs 102. For example, a third or fourth or more other reservoir 93, 94, 95 may be arranged in the container 100. The supporting elements 116 facilitate tensional relief in order not to influence accurate weighing by the weighing means 130, when the reservoirs located within the container 100 are connected to the dialysis apparatus or system, as any tension between the blood treatment device and the reservoirs transmitted by the fluid lines (97-99, 104, 106) may influence the result of a weighing measurement.

A stiff cover element 120 may be pivotally mounted at an end section of the container 100 opposite its base. Locking means 121.1 may be disposed on the container 100 to arrest the cover element 120 in a non-pivotal position by means of the cover element 120. The first 101 and second reservoirs 102 may be retained in the receiving space 109 of the container 100. Further any expansion of the first and second reservoirs due to gas present in any of the reservoirs may be controlled, e.g. in case these reservoirs arc formed as flexible bags. The stiff cover element 120 may be furnished with at least one aperture 123 such that the weight of the cover element 120 is reduced and passageways e.g. for fluid lines are provided. The cover element 120 thereby may even have a grit like shape when there is more than one aperture 123 provided in the cover element 120.

At least one partition 124.1, 124.2 may be disposed inside the container 100 that vertically and/or horizontally partitions the receiving space 109 of the container into separate compartments. By means of the partition 124.1, 124.2 e.g. separate compartments for the first 101 and the second reservoir 102 may be formed inside the container 100. The partition 124.1, 124.2, especially when it is formed as a more or less horizontally arranged partition, may have an inclination with respect to at least one wall of the container 100. Due to this inclination, any reservoir resting on the partition or partition element having an inclination will also have an inclination allowing for any fluid outlet located in a lower part of the container to empty the respective container completely when fluid is pumped out of the reservoir.

The container 100 may be formed as a collapsible container 100.1. As such, when the container 100, 100.1 is not in use, it may be collapsed or folded, so that its size may be reduced, and it may easily be stored consuming less space. The container 100, 100.1 may be made collapsible by providing hinge-joints that may be arranged between any wall connections of the container 100, 100.1 either on its edges or within its walls.

At least one of the first 101 or second 102 or third 93 or fourth 94 reservoirs or a further reservoir 95 may feature a gas separator operable to extract gas from the reservoir so that it holds substantially only a fluid. Pressurizing the reservoir(s) is thereby reduced or prevented.

The outlets and the inlets of the reservoirs (97, 98, 99, 103, 104, 105, 106) may be resistant to bending and kinking, so that any interruption of fluid communication from the reservoirs located within the container 100 and the apparatus or a system suitable for dialyzing a biological fluid containing a protein-binding substance to be removed is avoided.

The balancing device 90 may further feature a support housing 150 for receiving the container 100. The support housing may have two side walls (152.1, 152.2) arranged on two opposite sides of an entrance opening 151 of the support housing 150. At least one load cell (131, 132, 133) may be associated with each of the side walls (152.1, 152.2) for weighing contact with a respective one of the at least one rigid point of application of the container 100. When the container 100 is located within the support housing 150, the container 100 is substantially protected from any interaction or agitation exposed on the container 100 from the outside so that a substantially undisturbed weighing process is facilitated. The support housing 150 may have a closing door member located at a side of the entrance 151 that may be closed before the balancing system, device, and method begins operating. The door-member may occupy at least 10%, 15%, 20%, 25% or more of the area of the wall.

The load cells (131, 132, 133) may be located on a plunger-member 153. Each plunger-member 153 may be connected to the respective side wall of the container 100 and may be linearly moveable between a first 154.1 and a second position 154.2, and wherein the plunger-member 153 is arrested in all directions perpendicular to the direction of linear movement by means of locking members 155.2 at least in its second position. The plunger-member 153 may be electrical or may be part of a hydraulic system and is adapted to move the container 100 from a first position when the container is moved into the support housing 150 into a second position when the container 100 is lifted up from the ground or floor 300 of the support housing 150 so that the only contact the container 100 has is the contact with the load cells (131, 132, 133) associated with the plunger-members 153. In this second position of the container 100 when also the plunger members 153 are in their second position 154.2, their extended position, the plunger members 153 are arrested by means of the locking member 155.1 or locking members such that the plunger members 153 are shock resistant so that substantially no agitation, shocks or vibrations obscure any weighing measurements performed by the load cells (131, 132, 133).

The weighing means 130 may feature a weighing plate arranged in the support housing 150 such that the weighing plate forms a floor of the support housing 150 on which the container 100 may be located. The weighing plate may contain a plurality such as three or more load cells (131, 132, 133) that may be connected for data exchange with the controller 140. With the weighing plate located within the support housing 150, a simple weighing means 130 is provided such that the container 100 only needs to be positioned on the weighing plate in its correct position in order to provide accurate weight measurements. Normally, transverse or sheer forces and leverage do not impact the weighing of the container 100 as long as the container position is fixed.

The object of the present invention is further achieved by a container 100 for a balancing device in an extracorporeal blood treatment device which is at least at its base part 108 and side walls 119.1 fluid tight and adapted for being weighed by the weighing means 130 of the balancing device 90 and which has a receiving space 109 for receiving at least a first 101 and a second reservoir 102 of the balancing device 90, and wherein the maximum loading capacity of the fluid tight receiving space 109 of the container 100 exceeds the maximum load of the first reservoir 101 and the second reservoir 102 jointly.

Due to the fluid tightness of the container 100 which houses the at least first reservoir 101 and second reservoir 102, substantially no fluid, neither a usable fluid, for example, a dialysis fluid or a replacement fluid, nor a waste fluid may leak at any of the reservoirs or at any of the fluid inlets and outlets including the fluid lines (97, 98, 99, 103, 104, 105, 106) from the outlets or inlets to the apparatus and system suitable for dialyzing a biological fluid containing a protein-binding substance to be removed. Therefore, balancing the fluid volume and flow in the apparatus and system suitable for dialyzing a biological fluid containing a protein-binding substance to be removed using the balancing system and device described herein includes any liquids that may leak from any of the reservoirs, inlets, outlets or transport lines described herein. Such leaking fluids are collected by the fluid tight container and are thereby included in the balancing calculations performed by the system and device described herein.

Further features and advantages as well as particular embodiments of the balancing system, and device, including the container, arc outlined in the above description and arc incorporated herein by reference.

Balancing Method

The method for balancing the flow or volume of fluids, using a balancing apparatus or system as described herein, in an apparatus and system suitable for dialyzing a biological fluid containing a protein-binding substance to be removed, feature placing at least a first reservoir 101 for a first fluid that includes a usable fluid for the dialysis circuit and a second reservoir 102 for a second fluid that includes a fluid from the biological fluid circuit, such as a waste fluid or an ultrafiltrate, in a single container 100. A fluid outlet of the first reservoir 103 and a fluid inlet of the second reservoir 105 are brought into fluid communication with the dialysis apparatus or system. The container 100 having at least the first 101 and the second reservoir 102 contained therein is brought in weighing contact with load cells (131, 132, 133) of a weighing means 130 that is in data communication with a controller 140.

The methods include measuring the total weight of the container 100 including the at least first 101 and second reservoirs 102, for instance using the weighing means 130 described herein, before the dialysis apparatus or system begins operating, to define an initial system weight ($sw_0$) of the container 100. The container 100 may include at least one, for instance, a third 93 or fourth 94, additional reservoir for a further fluid such as, for instance, a concentrate of an active substance for the dialysis circuit. The methods also include controlling pumping means 101.1, 102.1 for the first reservoir fluid and the second reservoir fluid such that the initial system weight is maintained, maintained with a predefined surplus, or maintained with a predefined loss.

The methods may further feature placing at least one further reservoir, for instance, a third or fourth, additional reservoir (93, 94, 95) for a further fluid such as, for instance, a concentrate of an active substance usable in the dialysis circuit outside of the single container 100. A fluid outlet of the at least one further reservoir (e.g. 97), for instance, a third or fourth, additional reservoir may be brought into fluid communication with the dialysis apparatus or system. As such, the methods may further feature measuring any fluid, for instance, a concentrate being provided from the further reservoir (93, 94, 95) to the dialysis apparatus or system volumetrically when the extracorporeal blood treatment circuit is in operation, calculating a weight of the fluid concentrate being provided to the apparatus and system suitable for dialyzing a biological fluid containing a protein-binding substance to be removed based on its density and provided volume any time when fluid concentrate is being provided to the apparatus and system suitable for dialyzing a biological fluid containing a protein-binding substance to be removed and recalculating the initial system weight of the container 100 by adding the calculated weight of the fluid concentrate being provided to the dialysis apparatus or system to obtain a redefined initial system weight. If the density of the further fluid is not known or the further fluid is not measured volumetrically the weight loss of the further reservoir may be measured gavimetrically, and the initial system weight of the container 100 may be recalculated by adding the measured weight loss of the fluid concentrate being provided to the dialysis apparatus or system to obtain a redefined initial system weight.

While some reservoirs may be located outside of the fluid tight container that is being weighed by the weighing means, all amounts of fluids being provided into the dialysis apparatus or system are included in the balancing calculations. Hence, the present methods provide a constantly corrected system weight that is constantly compared to the weight of the container. Any waste or excess fluid obtained from the dialysis patient or subject is collected in the second (waste or filtrate) reservoir. Only fluid that is extracted from the patient (ultrafiltrate) or fluid that remains in the patient (bolus) is recognized by the balancing method. Such fluids are a surplus or a loss of the initial system weight. Thus, any possible measurement error is dramatically reduced. If an amount of 4000 ml fluid is removed from the dialysis patient or subject in 4 hours by ultrafiltration, and the measurement error is +/−1%, then a deviation of only 4 ml is possible. In 24 hours, this amounts to 24 ml. Compared to the requirements of the IEC Norm No. 60601-2-16 3 (ed. 3.0) subclause 201.12.4.4.103 for chronic dialysis, where the maximum deviation between the fluid added and the fluid withdrawn is ±400 ml per 4 hour period, the present methods provide an enormous improvement.

Operation of the dialysis apparatus or system may be interrupted when a deviation of the initial system weight in excess of a predefined threshold is detected by the controller in order to avoid any harm to a patient. Similarly, the flow of fluid, for instance a dialysate, from the first reservoir 101, and the flow of fluid, for instance, an ultrafiltrate into the second reservoir 102, may be controlled, for instance, by one or more pumps (101.1, 102.1) in order to maintain the total volume of fluid within the dialysis apparatus or system within a preferred range. Similarly, the flow of fluid, for instance an acid or base or concentrate thereof, from the third reservoir 93, and the flow of fluid, for instance, an acid or base or concentrate thereof from the fourth reservoir 94, may be controlled, for instance, by one or more pumps 94.1 in order to maintain the total volume of fluid within the dialysis apparatus or system within a preferred range. The preferred range may be, for instance, within 10%, 5%, 4%, 3%, 2%, 1% or even 0.5% or 0.2% or 0.1% of the initial operating volume before the dialysis apparatus or system begins operating.

Distinctions and Advantage over Prior Art Balancing Apparatuses and Systems

Ultrafiltrate is the fluid that is extracted from the patient during dialysis. Filtrate, as described herein, is the cumulative fluid that is pumped into the filtrate-bag by the dialysis-circulatory system. The breakdown of the filtrate can be described as follows:

$$\text{Filtrate} = \text{Permeate} + \text{Concentrate 1} + \text{Concentrate 2} + \text{Concentrate}_x + \text{Ultra-filtrate} + \text{Pre-dilution} + \text{Post-dilution}$$

Concentrate 1 may be NaOH, and Concentrate 2 may be HCl. In such a representation, Permeate+Concentrate 1+Concentrate 2+Concentrate$_x$ are introduced into the dialysis circuit. Some ultrafiltration control systems are known in the art.

Pressure Controlled Systems

UFK is the ultrafiltration coefficient of a dialyzer membrane and is assumed to be constant. However, the ultrafiltration coefficient depends upon various parameters including. hematocrit, and may vary so that the resulting ultrafiltration rate is likely to deviate from the intended one. TMP, the transmembrane pressure may be adjusted. The ultrafiltration rate UFR is the result (UFR=TMP×UFK). This principle is no longer used for modern dialysis machines.

Ultrafiltration Control Based on Differential Flow Measurement

Ultrafiltration control based on differential flow measurement relies upon accurate flow meters in the dialysate path as input to a feedback loop that controls the dialysate effluent pump. An additional ultrafiltration pump in parallel to the dialysate-out flow meter is used by some devices. This allows using low cost flow meters that are operated at equal flow. Three types of flow meters are commonly used. The electromagnetic and turbine flow meters are sensitive to volume flow while the Coriolis force flow meter is sensitive to mass only. A problem with these methods is the accuracy of the flow meters as the typical volumetric accuracy is 1%. The electromagnetic flow meter for example is used in the dialysis system Gambro Ak 200, and the Coriolis force flow meter is used in the Gambro Artis dialysis system. With these methods, the maximum dialysate flow rate in single pass open loop dialysis systems is limited by the accuracy of the flow meters.

Volumetric Ultrafiltration

Volumetric ultrafiltration relics on balancing chambers to create a temporarily closed system but without recirculation of dialysate. These balancing chamber systems are also called "flow equalizers" because they equalize the flow of fresh and spent dialysate. A balancing chamber is separated into a "fresh dialysate" and a "spent dialysate" compartment by a membrane to avoid mixing of fresh and spent dialysate. Because the volume of the system does not change, no net fluid transport takes place through the dialyser membrane. With an additional ultrafiltration pump, fluid can be removed from the dialysate circuit. Because the only connection to the environment is through the dialyzer membrane and the patient, this fluid is removed from the patient. As such, the action of the ultrafiltration pump reduces the pressure in the dialysate system creating a pressure gradient between blood and the dialysate side. This in turn causes ultrafiltration that commences until the pressure between the blood and the dialysate is again equalized. At this point precisely the same amount is ultrafiltered as previously withdrawn by the ultrafiltration pump.

This method of balancing the fluid uses a temporarily closed circuit that switches from one chamber to the other one. Therefore, the maximum dialysate flow rate depends on the accuracy of the balancing chambers. These balancing systems are not suitable for recycling the dialysate. The ultrafiltration is performed by a separate pump, and the accuracy depends upon the pump. This method is used, for example, in the Fresenius 5008® and the Nipro® Surdial X®.

Duplex Pump Technology

The duplex pump balancing system works with a double piston pump. Both chambers have exactly the same volume whereby the pistons move in contrary directions. Thus, the same volume pumped into the closed circuit is removed at the same time. The ultrafiltration is realized by a separate pump. As these devices work as a single pass device, the maximum flow rate is limited by the double piston pump. This method is used, for example, in the Nikkiso DBB®.

With an additional ultrafiltration pump, fluid can be removed from the dialysate circuit. Because the only connection to the environment is through the dialyzer membrane and the patient, fluid is removed from the patient. As such, the action of the ultrafiltration pump reduces the pressure in the dialysate system creating a pressure gradient between the blood and the dialysate circuits. This in turn causes ultrafiltration that proceeds until the pressure between the blood and the dialysate systems equilibrate.

One particular prior art system for dialysis, the MARS system by Gambro features a liver dialysis system and method. The dialysis is performed using a recirculating system to recycle the dialysis liquid. However, the dialysis circuit and the recirculating system are not separated or decoupled. The balancing apparatus or system described herein provides distinct advantages over the prior art. First, the dialysis circuit and the dialysate regeneration unit are decoupled using a reservoir as described herein. The same dialysis liquid is used, not an extra circuit (MARS) whereby the exchange is across a dialyzer. Second, the dialysis liquid in the dialysate circuit is recycled but parts of it are replaced continuously by adding fresh dialysis liquid into the circuit and withdrawing dialysis liquid and ultrafiltrate convective across a filter from the dialysis circuit. Third, the system used by MARS performs balancing in a single pass circuit across a DIA flux dialyzer. Fourth, the dialysate (for instance, albumin) recycling may be performed independently from the flow rate passing through the dialyzer thereby affording a higher flow rate in the dialysate regeneration unit. Fifth, fluid may be added and removed from the closed dialysate circuit separately, not across one membrane.

Basis of the Balancing Apparatus or System

The primary goal of the balancing apparatus or system described herein is to balance the fluids in the patient undergoing dialysis. The maximum permitted deviation of the patient's weight is preferably about ±400 grams per treatment. The maximum deviation of the patient's weight per hour is preferably ±100 grams. The basis of the balancing apparatus or system described herein is a scale for measuring weight. The dialysis methods described herein are performed using a recirculating dialysis circuit. The dialysis circuit is connected to its surroundings across a dialyzer membrane. The dialysis circuit and the dialysate regeneration circuit are decoupled or separated by a reservoir as described herein.

Fluid inlets and outlets of the dialysis circuit (e.g., permeate, concentrates, and waste) are substantially fluid tight. Piston pumps, syringe pumps, check valves, etc. may be used. However, recirculation within the dialysis circuit is performed using a recirculation pump that is not fluid tight. Nonetheless, the volume of liquid pumped into the closed circuit and the volume removed from the closed circuit must be equal. To remove fluid from a patient, more fluid must be removed from the circuit then pumped into the circuit. Because of the volume and pressure reduction in the closed dialysis circuit, fluid moves across the dialyzer membrane into the circuit.

If air is introduced into the closed dialysis circuit, the volume of liquid decreases. Since the scale is measuring the weight and does not realize the liquid volume reduction in the dialysis circuit, liquid continues to move across the dialyzer membrane into the blood. Therefore, gas must be continuously removed from the dialysis circuit in order to maintain the liquid volume constant.

As long as the volume of liquid within the closed dialysis 2 and dialysate regeneration circuit 16, 29, 74, 75 is constant, the flow rate of the dialysis liquid does not impact the fluid balancing. Only the difference between the flow rates into the closed circuit and out of the close circuit have an impact on weight deviation, i.e. ultrafiltration. In the balancing apparatus or system described herein, permeate, waste and ultrafiltrate are provided in a container 100 on a scale 130. The addition of ultrafiltrate increases the weight of the container 100. All additional liquids, for instance, the concentrates that are also added to the closed dialysis circuit are measured volumetrically or gravimetrically. The additional weight (or volume*density) also increases the weight of the container 100. The target weight of the container 100 is calculated and achieved by constant liquid removal from the closed dialysate circuit.

FIG. 29 illustrates the principles described and implemented by the dialysis apparatus or system featuring a balancing apparatus or system as a component thereof. Considering the patient undergoing dialysis, the fluid returned is equal to the fluid removed less the ultrafiltrate.

Structure and Functions of the Reservoir

The dialysate reservoir 67 described herein functions to both connect and separate the dialysate 2 and the dialysate regeneration circuit 16, 29, 74, 75 since the reservoir is placed between the two pathways. This provides the advantage that it is possible to maintain continuous flow of fluids in the dialysate 2 and the dialysate regeneration circuitries 16, 29, 74, 75. Further, it is possible to maintain distinct and different volumetric flow rates of dialysate in the dialysate 2 and the dialysate regeneration circuitries 16, 29, 74, 75. For instance, the volumetric flow in one circuit may be a multiple of that in the other circuit. These distinct volumetric flow rates in the circuits are possible by maintaining a buffer in the reservoir.

For the purpose of dialysis, the dialysate used is extracted from the reservoir 67. The volumetric flow rate for the dialysate in the dialysate circuit 2 is easily adjustable within a range of 100 ml/min-4000 ml/min and is independent of the flow rate in the dialysate regeneration circuit 16, 29, 74, 75.

The reservoir 67 is preferably made of glass (transparent, not averse to disinfection, durable, and inert), has a volume of preferably 10-3,000 ml, and has at least one opening. In some instances, it may feature two ports on the sides acting as inlets/outlets for the dialysate (from the dialysate 2 and the dialysis regeneration circuits 16, 29, 74, 75), one port at the bottom to facilitate the emptying/pump-out of the fluids within, two ports at the top (one for each sensor and to facilitate removal of air/fluids. There may be one pH-probe 11 and one temperature sensor 10 at each port. The removal of air through both of these ports can be achieved either by using separate or common valves. The ports located at the sides may also be used as outlets. The positions and angles of the inlets and the outlets for the dialysate may be optimized for consistent mixing of the dialysate (dialysate from the dialysate circuit and that from the dialysate regeneration circuit may have different pH values, temperatures and concentrations of cleansed albumin). Entrapment of air bubbles in the dialysate at the bottom-most port is avoided on account of the flows. Air may rise to the top in the form of bubbles.

pH Measurement

In dialysis machines, pH measurement may be performed in the form of conductivity or optical measurements. However, with albumin-containing dialysates, this is not possible because of the ion-buffering with albumin. Therefore, electro-chemical or optical pH probes are preferred. Redundant monitoring of the dialysate is rendered possible via dual pH-measurements. Coupling the sensors to the electronics/control system enables using a software for pH-regulation in the dialysate. pH-regulation of the dialysate facilitates $CO_2$ removal from the blood in the dialyzers. The pH-probes in the reservoir monitor the disinfection processes. pH values <3 and >9 must be possible. The temperature is measured alongside with a desired range of 10-95° C. Integration of the pH-probes within the reservoir enable negligible flow-resistance at the probes as compared to those encountered within a tube. Shielding of the pH probes with the help of isolation is provided to ensure patient safety.

Suction of Air and Fluids

Automated suction of air from within the reservoir 67 is possible during the filling process. By placing a valve between the two suction lines that switches alternatively, both the air detectors detect the presence of fluids flowing through them. Automated suction of gas from within the reservoir 67 is possible during the treatment via a control mechanism (gas, especially $CO_2$ (due to conversion of bicarbonate at a pH of 3), that is present in the acidic dialysate regeneration pathway 37). Automated suction of fluids from within the reservoir may be provided during disinfection.

Suction of fluids/air from within the reservoir 67 is possible by placing two air detectors at the top of the reservoir prevent the suction of albumin-containing dialysate during treatment. The design for the armature above the reservoir for pH/temperature probes 10, 11 and air and fluid suction may be customized. Additional suction is possible at the lower-most point in the reservoir. The presence of valves is deemed necessary to determine the different points of time at which various pathways may be rendered free of air, suctioned or filled. The valves help ensure the rinsing of a certain tube/pathway during the disinfection. The detectors may be connected to a control board, although it is possible to place a level sensor inside or outside the reservoir to keep the liquid level inside the reservoir constant.

Determining the Filling Level

Determining the filling level in the reservoir 67 is performed via sensors placed on the reservoir 67. There may be air detectors at the top of the reservoir. There may also be a capacitive/ultrasonic/float gauge.

Further Alternatives for Treatment

In the case of a single pass dialysis, it is possible to draw the fluids via the filtrate pumps. In the case of normal dialysis or respiratory dialysis, a total interchange of fluids (albumin-dialysate) between the dialysate and dialysate regeneration circuits is possible. It is possible to replace the filters in the dialysate regeneration circuit while performing a dialysis treatment via suction. A constant air chamber in the reservoir can work as a buffer and reduce pressure variations within the dialysis circuit (pressure variations can occur especially during cross switch).

Fluid Control in a Recirculation Circuit

Dialysate flow is recirculated in the dialysis apparatuses and systems described herein. Therefore the name does not correspond to the dialysate flow in non-recirculating hemodialysis procedures as there the dialysate flow is also the spent dialysate volume. The fluid volume which corresponds to the spent dialysate in the dialysis apparatuses and systems described herein are called the supply fluids which consist of permeate and concentrates.

Control of Ultrafiltration of a Patient

Five fluid circuits which must be balanced as shown in, for example, FIG. 25. The first circuit is the patient. The dialysis system should be able to withdraw fluid from the patient or to keep the fluid balance zero. 60601-2-16 3ed Subclause 201.12.4.4.103 NET FLUID REMOVAL prescribes the accuracy for 4 hours of dialysis treatment, not for 24 hour or 48 hour treatments. The dialysis apparatus and systems described herein provide that this normative requirement may also be fulfilled for a 24 hour and 48 hour dialysis treatment. This means ±400 ml for 24-48 hours and ±100 ml for one hour are the limits for deviations of the fluid balance of the patient. The patient can lose or gain fluid from or to the dialysate circuit. To be able to withdraw more fluid in the dialysate-out-path than in the dialysate-in-path of the dialyzer for ultrafiltration of the patient, the dialysate pumps are not allowed to be completely fluid-tight. The dialysate pumps are the place, where in normal dialysis machines or other systems the balancing chambers or other technical possibilities are located. The amount of ultrafiltrate to be removed can exceed 10 liters in 24 hours, but in most cases 5 liters are sufficient.

Overview of Fluid control of Dialysate and Dialysate Regeneration Circuit:

The balancing apparatus or system allows balancing the inflow of permeate and concentrates with the outflow of filtrate and ultrafiltrate. The combination of the dialysate circuit 2 and the dialysate regeneration circuit 16, 29 contains the dialysate to be recirculated and has a volume of approximately 0.2-5 liters. The applied dialysate flow (the flow through dialyzer) is normally between 0.05-4000 ml/minute, preferably 500-2000 ml/min. By comparison the normally executed continuous hemodialysis in intensive care medicine needs an average of only 33 ml/minute flow rate for the dialysate through the dialyzer. Conventional hemodialysis devices can account for a dialysate flow through the dialyzer ranging from about 100 to 1000 ml/minute. Such devices are mostly used for about 4, up to 8 hours.

The balancing methods described herein can be used for up to 24 or 48 hours with a dialysate flow rate even higher than normal dialysis machines without having a connection to a reverse osmosis unit. This is particularly helpful for patients not only on liver or kidney dialysis but also requiring or exclusively requiring lung support for oxygenation or $CO_2$ removal. The benefits of a 24-hour treatment are slower fluid extraction in case of unstable patients, improved detoxification due to emptying of compartments, and the possibility of providing lung support which has to be provided continuously.

To provide such a 24-hour treatment, a conventional dialysis procedure would require a total of 2,880 liters of permeate for a dialysate flow of 2000 ml/minute. The ultrafiltration control of a conventional dialysis device must adhere to a maximum deviation of ±400 ml during the entire duration of treatment. Therefore, for a 24 hour treatment, with a dialysate flow of 2000 ml/minute, an accuracy on the order of ±0.014% must be maintained. The currently optimal balancing systems have a deviation of 0.1%, but some dialysis machines only achieve 1%. Industry independent analyses do not exist. The norm requires an accuracy (±400 ml) of 0.33% for a dialysate flow of 120 liters in 4 hours. Such a recommendation does not yet exist for 24-48 hours dialysis procedures as used in ICU units.

The balancing method described herein, in contrast to a conventional dialysis, is performed in a closed, re-circulatory dialysis system. Such a dialysis system facilitates a continuous and effective conditioning of the dialysate and moderates the cumulative permeate intake for a 24-hour treatment to a maximum of 550 liters thereby necessitating an accuracy of just under ±0.073% for the equilibration. Dialysis machines having a dialysate flow of more than 120 liters need a direct access to a reverse osmosis unit.

The fluids needed for treatment with such a dialysis machine would be made available in an exchangeable container where the permeate is present initially, and during the treatment the filtrate is filled into it. Both fluids are separated by flexible bags. The fluids and the volume (120 l) of the container are sufficient for providing a treatment of at least 4 hours and up to 36 hours duration depending on the supply flows used. Consequently, the container 100 may be replaced for a maximum of 6 times during a 24-hour treatment. The container 100 is located on the weighing means (scales) 130 during the entire treatment. However, the accuracy of the total weight plays no role since the initial value is recorded and thereafter only the changes in the weight are determined. The fluids that are initially present in the container are directed through the circulatory dialysis pathway, put into application, partly reconditioned and subsequently brought back in the container as filtrate. The concentrate and the pre-/post-dilution fluids are placed in the container/weighing means (scales) 130 as well. Thus, a change in recorded weight implies merely the ultra-filtrate extracted from the patient.

The maximum amount of fluids that can be extracted from the patient within 4 hours is 4000 ml, and this change in weight is simply measured and provided as an output by the weighing means (scales). An accuracy of ±0.1% implies a maximum deviation of 4 ml in 4 hours. With every replacement of the container, a deviation of 4 ml is thereby probable. This in turn provides a maximum deviation of 24 ml in 24 hours with a maximum of 6 intermittent container replacements.

It is possible to administer the concentrates separately to the dialysis circuit 2. This can be done in either a volumetric or a gravimetric manner, preferably through piston pumps or syringe pumps due to high dosing accuracies of the order of 1% and the absence of any back flow of fluids. A maximum of 4.5 liters (e.g., 3.072 Liter) of concentrates may be administered to the dialysis system in 4 hours which translates into a deviation of 22.5 ml with an accuracy of ±0.5% for the dosage. The administered concentrates and the ultra-filtrate consequently increase the volume of fluids in the container by a maximum of 8500 ml in 4 hours. This corresponds to an accuracy of ±0.1% for a maximum deviation of 8.5 ml in 4 hours. In a worst-case scenario (22.5 ml of concentrate in deficit and 8.5 ml of fluids in excess on the scales), the patient would undergo an erroneous equilibration to the amount of 31 ml in 4 hours. By extending the slope of this calculation, the patient would undergo an erroneous equilibration to a maximum amount of 186 ml in 24 hours. As such, a maximum of 27 liters of concentrate would be provided to and a maximum of 24 liters of fluids would be removed from the patient during a 24-hour treatment. Since the initial output weight of the container 100 must not be recorded, a maximum of 51 liters must be equilibrated over a period of 24 hours in this procedure.

$X=UF+(Conc.)+Y$ $X$=Volume to be equilibrated $Y$=Error in the equilibration

A conventional dialysis machine, one in which the dialysate would not be re-conditioned and re-circulated and would thereby need 2,880 Liter of dialysate in a single pass procedure, would present a maximum deviation of 2.8 liters with an accuracy of ±0.1% for equilibration. This could turn fatal for the patient. Since all fluids that are given into the dialysis circuit and later removed are to be measured volumetrically and/or gravimetrically, there a redundant monitoring system is provided for the gravimetric equilibration of fluids in the container.

The filtrate is composed of the following parts: Filtrate=Permeate+Concentrate 1+Concentrate 2+Concentrate$_x$+Ultra-filtrate+Pre-dilution+Post-dilution. Concentrate 1 may be NaOH, and Concentrate 2 may be HCl. It is possible to have all fluids, with the exception of ultrafiltrate, in the container before or just at the time that the treatment begins.

Detailed Description of the Flow Paths

Dialysate Circuit Path to or from Reservoir: Going Directly to the Reservoir

Whether this occurs depends upon the dialysate flow rate, the difference between dialysate flow and dialysate regeneration flow goes directly into the reservoir 67 and then into the dialysate in flow. The opposite happens if the dialysate flow is lower than dialysate regeneration flow. Then, from the reservoir 67 a flow proceed in the direction of the dialysate regeneration circuit 16, 29, 74, 75 from the reservoir 67. This works because there is a closed dialysate 2 and dialysate regeneration circuit 16, 29, 74, 75 without changes of more than 100 ml within seconds. In the flow going to the reservoir 67, gas may develop, for example, from pressure drops. Therefore, a degassing is necessary in this circuit. By necessity, the dialysate circuit 2 and the dialysate regeneration circuit 16, 29, 74, 75 must be closed. The only open part is the semipermeable membrane 23A, 23B (see, 1, 5, 22A, 22B) separating biological fluid such as blood and dialysate.

Dialysate Circuit Path to Dialysate Regeneration Circuit: Passing into the Dialysate Regeneration Circuit For an exemplary dialysate flow of 800 ml/min, 300 ml pass, after passing through the dialyzer, directly into the reservoir and 500 ml into the dialysate regeneration circuit. Through this circuit the ultrafiltrate and the pre- or postdilution (if there is any) must be withdrawn from the blood. This is only possible with "open" pumps like gear pumps in the dialysate paths to and from the dialyzers and gear pumps within the dialysate regeneration circuit. Pumps bringing fluid into the system from outside, for instance, the permeate or the concentrate or pumping something from outside the system must be completely tight, for instance, piston pumps. In addition no air should be retained in the dialysate, dialysate regeneration circuit or the reservoir. Retaining air causes a positive fluid balance for the patient. To avoid sharp pressure increases or drops, the tubes have to have some compliance like silicon tubings, or a pressurized tank (for instance, a reservoir with a clearly defined gas volume) is used to compensate pressure variations.

Dialysate Regeneration Circuit

The inflow comes from the dialysate circuit 2, and the outflow goes to the reservoir 67. In the dialysate regeneration circuit 16, 29, 74, 75, gas ($CO_2$) mostly develops on the acidic part of the circuit 37. In the circuit, pumps like gear pumps (not tight) are necessary to allow ultrafiltration removal by the waste pumps. The next circuit is the inflow of supply (permeate and concentrate) and the outflow of filtrate to and from the dialysate regeneration circuit 16, 29, 74, 75. This circuit has a maximum capacity of 550 liters in 24 hours and a minimum flow rate of 50 liters. The fluid is provided in 60-120 liter bags of permeate in the containers and a 2-7 liter canister for each concentrate. To have a closed system, piston pumps and check valves are necessary so that no fluid of the dialysate regeneration circuit can flow into the permeate container or the concentrate canisters.

Balancing Options of a Circulatory System with Scales

The balancing apparatuses and systems described herein may feature securing all the fluids (permeate, concentrates, pre- and post-dilutions) on a single scale with the ultrafiltrate kept extra aside. It is preferable to place only the permeate (pre- and post-dilutions) and filtrate on the single scale. The filtrate is monitored through the increase in weight on the scale. The concentrate must be administered through a volumetric metering pump. The accuracy of these pumps is guaranteed on the basis of minimal volumetric flows. No strain relief is necessary for the tubes connected to the concentrates.

Pumps for Equilibration

Piston Pumps allow for equilibration. They provide the best available sealing characteristics with no back-flow/regurgitation possible. Redundant monitoring of the fluidic volumes is provided by via the piston pumps or by additional scales for the separated reservoirs or concentrates.

Strain-Relief for the Tubing Connections to Avoid Scale Changes Due to this

The tubing layout is equipped with strain reliefs. No influence of the push-pull effects of the tubes to the scales is thereby provided. Between the container and dialysis system, the tubing is provided in a layout to avoid or minimize contact with the housings/enclosures, i.e. fixed onto the dialysis system. The positions of the tubes from the fluid-bags in the container are fixed and made resistant to movements. The linkage/connection between the machine and the container is devoid of any strain. Therefore, equilibration on the scales remains unaffected.

Weighing

The possibilities for weighing the system include lift systems, platform scales, and spring/crane scales. It is preferable to use weighing units or load cells so that redundant weighing via cross checking and comparison can be performed. Redundant measurements may be made by the load cells through the system. Signal transmission in the load cells may be accomplished by a digital transmitter over an analog counterpart. Software noting compensation of displaced weight; and regulation/control via two load-cells is sufficient for the weighing process. Monitoring of the transmembrane pressure (TMP) to monitor the weighing/weight may be performed. Comparing the dialysate pressure and the blood pressure to avoid any possible back filtration may also be performed.

Container

The container described herein may feature a handle, anti-static wheels, formed of a rust-proof material, voluminous, and fluid tight. No fluids are present on the outside of the sealed container. The container must be able to accommodate a volume of at least 120 liters (fluid breakdown=permeate+concentrates+post-dilution+pre-dilution+ultra-filtrate). The tubing layouts are provided with impeded creases in the permeate tube so that suction of the permeate remains unhindered. A sealed, front-open hatch on the container is provided for improved usability. An upper hatch is provided to facilitate the placement of post- and pre-dilution fluids. The container may be thermally insulated. The permeate within the container is maintained at a cooler temperature to enhance its applicability in the heat exchanger so that these fluids are automatically balanced within the system. The container must be structurally stable enough in order to allow evenly distributed weighing, prevent any deformations due to the contained fluids and allow itself to hang freely, to avoid damage during moving. The container may position itself on a specially built platform on top of the load cells and thereby remains in a free-hanging position. Displacement of the container is rendered difficult due to the structural frame and the housings that inhibit contact, and the Container may not come against the structural frames from the inside. Absolute position sensors are provided to determine the location of the container. The Container is completely isolated from the housing. The dialysis system and the filling and emptying units are functionally connected via the container in order to ensure that the container is properly filled and emptied.

Lift Mechanism

Stabilization of the lift mechanism for the container may be provided, for instance, with support from the sides and pre-defined limits of the lifting stretch. The movement of the dialysis machine during treatment is facilitated by this stabilization. The lift mechanism guides the container by an alignment to ensure a fixed position.

Bags

Bags are provided having a volume of 60-120 liters. The bags are equipped with at least one inlet and outlet for fluids each and a separate outlet for air. The bags and the tubes therein are especially designed to provide strain relief. The bags may be evenly distributed for unfolding of the bags and fixing them in the container. Two separated bags are provided from the permeate and filtrate, respectively. This dual-bag concept in the container is designed to physically separate the two in a single container. There may be thermal insulation between the two bags or chambers in order to maintain a cooler temperature of the permeate. A tripled-layered bag with an air-cushion may be provided as the isolating layer in the middle. A safeguard against mixing up of the connectors between the container and the dialysis system may be provided by using distinct couplers and sensors.

The fluids are placed in flexible bags within the container which requires the tubes to be positioned in such a manner that the guide-clamps help prevent the tubes from being bent or forming creases and getting squeezed in between other parts and thereby ensures a continuous flow of fluids. The fluids may be placed in a common case with multiple divisions or in individual cases within the container. Reduced spatial requirements, easier handling and combined inherent processes are the advantages offered by the multiple cases option. The distinct fluids must ideally be kept separate from each other in thermal terms and at the very least, physically. The case for filtrate must offer at least one inlet for filtrate and one outlet for gas. All the other cases must present at least one outlet for the respective fluids.

While the present apparatuses, systems and methods have been described in terms of specific embodiments thereof, it will be appreciated that in view of the present disclosure, numerous variations upon the apparatuses, systems and methods are now both described and enabled to those skilled in the art, which variations may be found within the present teachings. Accordingly the apparatuses, systems and methods are to be broadly construed, and limited only by the scope and spirit of the disclosure and of the claims following.

REFERENCE NUMBERS 1 dialyzer
2 dialysis fluid circuit
3 biological fluid circuit
4 metering pumps for adding acid or base
5 dialysis, filtration or diafiltration device
6 heating and cooling apparatuses
7 device for adding substituate
8 device for adding caffeine
9 a device for irradiating the usable fluids with waves/fields
10 thermometer
11 pH meter
13 predilution fluid
14 postdilution fluid
15A aterial blood line
15B venous blood line
16 regeneration circuit
17 fluids added to the dialysate
18 fluids removed from the dialysate
19 substitution fluids
21 biological fluid circuit
22A,B dialyzers
23A,B semipermeable membrane
24 pump
25 predilution fluid
26 predilution pump
27 postdilution fluid
28 postdilution pump
29 dialysate regeneration unit
30 first dialysate pump
31 substitution fluids
32 substitution fluids
33 pump
34 pump
35 second dialysate pump
37 the "acidic flow path,"
38 the "alkaline flow path,"
39 acidic solution
40 acid pump
41 alkaline solution
42 base pump
43 regeneration pump on the acidic flow path
44 regeneration pump on the alkaline flow path
45 detoxification unit
46 detoxification unit
47 valve mechanism comprising switching valves
48 valve mechanism comprising switching valves
49 filtrate pump
50 filtrate pump
51 discharge fluid
52 discharge fluid
53 scales
54 scales
55 scales
56 scales
57 sensor
58 sensor
59 sensor
60 sensor
61 sensor
62 sensor
63 temperature regulation unit
64 temperature regulation unit
64A dialyzer
64B dialyzer
65A semipermeable membrane
65B semipermeable membrane
66 pump
67 dialysate reservoir
68 first dialysate pump
69 substitution fluid
70 substitution fluid
71 pump
72 pump
73 second dialysate pump
74 dialysate regeneration unit
75 dialysate regeneration circuit
76 biological fluid circuit
81 point of application
82 panels
83 arrow
84 arrow
90 balancing device
91 balancing support
92 fluid line
93 further reservoir
93.1 volume metering pump
94 further reservoir
94.1 volume metering pump
95 further reservoir
95.1 pumping means
96 further reservoir
96.1 pumping means (volume metering pump)
97 fluid line
98 fluid line 99 fluid line
100 container
100.1 collapsible container
101 first reservoir
101.1 pumping means
102 second reservoir
102.1 pumping means
103 fluid outlet (of first reservoir)
104 first fluid line
105 fluid inlet (of second reservoir)
106 second fluid line
108 base part (of container)
109 receiving space (of container)
110 (fluid tight) coating
111 (fluid tight) lining
112 rollers
112.1 antistatic roller kit
113 roller mountings
114 break-member (of roller)
115 interface (at container)
116 supporting elements
117 door-member
117.1 door
117.2 flap
117.3 pivot bearings
118 (access side) wall (of container)
119.1 (side-)walls (of container)
119.2 opposite side wall to access side wall
120 cover element
121.1 locking means
121.2 (counter) locking means
122 pivot bearings
123 aperture(s)
124.1 partition
124.2 partition
125.1 compartment
125.2 compartment
130 weighing means
131 load cells
132 load cells
133 load cells
136.1 line
136.2 line
136.3 line
136.4 line
137 line
140 controller
141 line
142 line
150 support housing
151 entrance opening (of support housing)
152.1 sidewall
152.2 sidewall
153 plunger members
153.1 plunger head
154.1 first position
154.2 second position
155.1 locking member
155.2 (counter) locking member
156.1 positioning sensor
156.2 positioning sensor
157 cylinders
158 rollers
160 extracorporeal blood treatment device
170 extracorporeal blood treatment circuit
171 first blood line
172 second blood line
200 patient
300 floor

We claim:

1. A method for removing an unwanted substance from a biological fluid in an apparatus or a system suitable for dialyzing a biological fluid containing a protein-binding substance to be removed, comprising:
   a) dialyzing a biological fluid against a dialysis fluid containing an adsorber for a protein-binding substance to be removed through a semipermeable membrane,
   b) adjusting the dialysis fluid so that the binding affinity of the adsorber for the protein-bound substance to be removed is lowered and the substance to be removed passes into solution, and
   c) balancing the total fluid volume in the apparatus or system suitable for dialyzing a biological fluid containing a protein-binding substance to be removed using a balancing system, wherein the balancing system comprises:
      a container having at least a first reservoir for a dialysis fluid and a second reservoir for a waste fluid,
      a weighing means for weighing the container, and
      a controller configured to receive weighing data from the weighing means, and wherein all amounts of fluids provided into the dialysis apparatus or system are included in balancing calculations;
   wherein the controller is adapted to define an initial system weight including the total weight of the container measured by the weighing means before the apparatus or system begins operating; and
   wherein the apparatus or system further comprises pumping means for the first reservoir fluid and the second reservoir fluid, which are controlled by the controller such that the initial system weight is maintained, maintained with a predefined surplus, or maintained with a predefined loss.

2. The method according to claim 1 wherein adjusting the dialysis fluid in such a way that the binding affinity of the adsorber for the protein-bound substance to be removed is lowered and the substance to be removed passes into solution comprises the step of adding an acid, adding a base, adding a dialyzable substance, by dilution, or heating.

3. The method according to claim 1 wherein the biological fluid is blood.

4. The method according to claim 1 wherein the adsorber is albumin.

5. The method according to claim 1 wherein balancing the total fluid volume in the apparatus or system suitable for dialyzing a biological fluid containing a protein-binding substance to be removed is effective to maintain a substantially constant volume of fluid within the apparatus or system within about 1% of the initial operating volume before the dialysis apparatus or system begins operating.

6. The method according to claim 1 wherein balancing the total fluid volume in the apparatus or system suitable for dialyzing a biological fluid containing a protein-binding substance to be removed is effective to maintain a substantially constant volume of fluid within the apparatus or system deviating less than 0.5 liter in a 24 hour dialysis period.

7. An apparatus or a system suitable for dialyzing a biological fluid containing a protein binding substance to be removed comprising:
   a) a biological fluid circuit (3);
   b) a dialysis fluid circuit (2);
   c) a means (4; 6; 7; 8; 9) for solubilizing the protein-binding substance to be removed;
   d) a dialysis, filtration or diafiltration device (5); and e) a balancing system or apparatus suitable for balancing the total fluid volume in the apparatus or system suitable for dialyzing a biological fluid containing a protein-binding substance to be removed, wherein the balancing system comprises:
   a container having at least a first reservoir for a dialysis fluid and a second reservoir for a waste fluid,
   a weighing means for weighing the container, and
   a controller configured to receive weighing data from the weighing means, and wherein all amounts of fluids provided into the dialysis apparatus or system are included in balancing calculations;
wherein the controller is adapted to define an initial system weight including the total weight of the container measured by the weighing means before the apparatus or system begins operating; and
wherein the apparatus or system further comprises pumping means for the first reservoir fluid and the second reservoir fluid, which are controlled by the controller such that the initial system weight is maintained, maintained with a predefined surplus, or maintained with a predefined loss.

8. A method for dialyzing a subject in need thereof comprising:
   a) passing a biological fluid from the subject through a biological fluid circuit;
   b) dialyzing the biological fluid against a dialysis fluid containing an adsorber for a protein-binding substance to be removed through a semipermeable membrane,
   c) adjusting the dialysis fluid so that the binding affinity of the adsorber for the protein-bound substance to be removed is lowered and the substance to be removed passes into solution, and
   d) balancing the total fluid volume in the apparatus or system suitable for dialyzing a biological fluid containing a protein-binding substance to be removed using a balancing system, wherein the balancing system comprises:
      a container having at least a first reservoir for a dialysis fluid and a second reservoir for a waste fluid,
      a weighing means for weighing the container, and
      a controller configured to receive weighing data from the weighing means,
and wherein all amounts of fluids provided into the dialysis apparatus or system are included in balancing calculations, wherein the controller defines an initial system weight including the total weight of the container measured by the weighing means before step a); and
wherein pumping means for the first reservoir fluid and the second reservoir fluid are controlled by the controller such that the initial system weight is maintained, maintained with a predefined surplus, or maintained with a predefined loss, and wherein the fluid volume of the subject remains substantially constant.

9. The method of claim 8 wherein the adjusting the dialysis fluid so that the binding affinity of the adsorber for the protein-bound substance comprises adding an acid, adding a base, or heating.

10. The method of claim 8 wherein the biological fluid is blood.

11. The method of claim 8 wherein the adsorber is albumin.

12. The method of claim 8 wherein balancing the total fluid volume in the apparatus or system suitable for dialyzing a biological fluid containing a protein-binding substance to be removed comprises measuring the total fluid volume within the dialysis apparatus or system.

13. The method of claim 8 wherein balancing the total fluid volume is effective to maintain a relatively constant volume of fluid within the dialysis apparatus or system.

14. The method of claim 13 wherein the relatively constant volume is within 1% of the initial operating volume before the dialysis apparatus or system begins operating.

15. The method of claim 13 wherein the relatively constant volume is a deviation of less than 0.1 liter in a 24 hour dialysis period.

16. A method for treating a disease characterized by unwanted accumulation of a protein-binding substance in a biological fluid comprising:
   a) passing a biological fluid from the subject through a biological fluid circuit;
   b) dialyzing the biological fluid against a dialysis fluid containing an adsorber for the protein-binding substance to be removed through a semipermeable membrane,
   c) adjusting the dialysis so that the binding affinity of the adsorber for the protein-bound substance to be removed is lowered and the substance to be removed passes into solution, and
   d) balancing the total fluid volume in the apparatus or system suitable for dialyzing a biological fluid containing a protein-binding substance to be removed using a balancing system, wherein the balancing system comprises:
      a container having at least a first reservoir for a dialysis fluid and a second reservoir for a waste fluid,
      a weighing means for weighing the container, and
      a controller configured to receive weighing data from the weighing means,
and wherein all amounts of fluids provided into the dialysis apparatus or system are included in balancing calculations, wherein the controller defines an initial system weight including the total weight of the container measured by the weighing means before step a); and
wherein pumping means for the first reservoir fluid and the second reservoir fluid are controlled by the controller such that the initial system weight is maintained, maintained with a predefined surplus, or maintained with a predefined loss, and wherein the fluid volume of the subject remains substantially constant.

17. The method according to claim 16 wherein the disease is a hepatic disease.

18. The method according to claim 17 wherein the disease is cirrhosis.

19. The method according to claim 17 wherein the disease is liver failure.

* * * * *